(12) United States Patent
Subbaiah et al.

(10) Patent No.: US 10,555,957 B2
(45) Date of Patent: Feb. 11, 2020

(54) METHODS AND COMPOSITIONS FOR ENRICHING DHA LEVELS IN THE BRAIN

(71) Applicant: The Board of Trustees of the University of Illinois, a body corporate and politic of the state of Illinois, Urbana, IL (US)

(72) Inventors: Papasani V. Subbaiah, Chicago, IL (US); Poorna Yalagala, Chicago, IL (US); Sugasini Dhavamani, Chicago, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days.

(21) Appl. No.: 15/976,481

(22) Filed: May 10, 2018

(65) Prior Publication Data

US 2018/0325924 A1 Nov. 15, 2018

Related U.S. Application Data

(60) Provisional application No. 62/504,326, filed on May 10, 2017.

(51) Int. Cl.
| | | |
|---|---|---|
| A61K 31/661 | (2006.01) | |
| C07F 9/10 | (2006.01) | |
| A61K 9/107 | (2006.01) | |
| A61P 25/28 | (2006.01) | |

(52) U.S. Cl.
CPC .......... *A61K 31/661* (2013.01); *A61K 9/1075* (2013.01); *A61P 25/28* (2018.01); *C07F 9/10* (2013.01)

(58) Field of Classification Search
None
See application file for complete search history.

(56) References Cited

FOREIGN PATENT DOCUMENTS

WO 2015048554 A1 4/2015

OTHER PUBLICATIONS

Abeytunga et al Journal of Lipid Research (2004), 45(7), 1221-1231.*
Singh et al., Modulation of the activity and arachidonic acid selectivity of group X secretory phospholipase A2 by sphingolipids, Journal of Lip Research, vol. 48, 683-692, 2007.
Freund-Levi et al., w-3 Fatty Acid Treatment in 174 Patients With Mild to Moderate Alzheimer Disease: OmegAD Study, Arch Neurol/ vol. 63, 1402-1410, 2006.
Thomas et al., Epidermal growth factor prevents APOE4 and amyloid-beta-induced cognitive and cerebrovascular deficits in female mice, Thomas et al. Acta Neuropathologica Communications, 4:111, 2016.
Hashimoto et al., Docosahexaenoic acid: one molecule diverse functions, Critical Reviews in Biotechnology, vol. 37, No. 5, 579-597, 2017.
Kuai et al., High-Density Lipoproteins (HDL)—Nature's Multi-Functional Nanoparticles, ACS Nano., 10(3): 3015-3041, 2016.
Quinn et al., Docosahexaenoic Acid Supplementation and Cognitive Decline in Alzheimer Disease: A Randomized Trial, Jama. 304(17): 1903-1911, 2010.
Kuda, Bioactive metabolites of docosahexaenoic acid, Biochimie 136: 12-20, 2017.
Johansson et al., Choline up-regulates BDNF and down-regulates TrkB neurotrophin receptor in rat cortical cell culture, NeuroReport, vol. 20 No. 9, 828-832, 2009.
Valenzuela et al., Supplementing female rats with DHA-lysophosphatidylcholine increases docosahexaenoic acid and acetylcholine contents in the brain and improves the memory and learning capabilities of the pups, Grasas Y Aceites, 61 (1), 16-23, 2010.
Jain et al., Possible Role of Oxidative Stress and Brain Derived Neurotrophic Factor in Triazophos Induced Cognitive Impairment in Rats, Neurochem Res, 38:2136-2147, 2013.
Bickerton et al., Preferential Uptake of Dietary Fatty Acids in Adipose Tissue and Muscle in the Postprandial Period, Diabetes, vol. 56, 2007, 168-176.
Chen et al., The Sphingosine Kinase 1/Sphingosine-1-Phosphate Pathway in Pulmonary Arterial Hypertension, American Journal of Respiratory and Critical Care Medicine vol. 190 No. 9, 2014, 1032-1043.
Bekinschtein et al., BDNF and memory processing, Neuropharmacology 76, 677-683, 2014.
Chen et al., Plasma non-esterified docosahexaenoic acid is the major pool supplying the brain, Nature, pg. 1-12.
Rao et al., n-3 Polyunsaturated fatty acid deprivation in rats decreases frontal cortex BDNF via a p38 MAPK-dependent mechanism, Molecular Psychiatry 12, 36-46, 2007.
Arendash et al., A Diet High in Omega-3 Fatty Acids Does Not Improve or Protect Cognitive performance in Alzheimer'S Transgenic Mice, Neuroscience 149, 286-302, 2007.
Redgrave et al., Quantitation of the Transfer of Surface Phospholipid of Chylomicrons to the High Density Lipoprotein raction during the Catabolism of Chylomicrons in the Rat, J. Clin. Invest., vol. 64, 162-171, 1979.
Kietbowicz et al., An LC method for the analysis of phosphatidylcholine hydrolysis products and its application to the monitoring of the acyl migration process, Talanta 94, 22— 29, 2012.
Ivanova et al., Glycerophospholipid Identification and Quantitation by Electrospray Ionization Mass Spectrometry, Methods in Enzymology, vol. 432, 21-57.

(Continued)

*Primary Examiner* — Kamal A Saeed
(74) *Attorney, Agent, or Firm* — Thomas|Horstemeyer, LLP

(57) ABSTRACT

Described herein are at least compounds and formulations that can be or contain a docosahexaenoic acid-lysophosphatidylcholine (DHA-LPC) and/or eicosapenteanoic acid-lysophosphatidylcholine (EPA-LPC). Also described herein are at least methods of making and using the compositions and formulations DHA-LPC and/or EPA-LPC.

20 Claims, 50 Drawing Sheets

(56) References Cited

OTHER PUBLICATIONS

Lemaitre-Delaunay et al., Blood compartmental metabolism of docosahexaenoic acid (DHA) in humans after ingestion of a single dose of [13C]DHA in phosphatidylcholine, Journal of Lipid Research vol. 40, 1867-1874, 1999.
Chen et al., Structural elucidation of molecular species of pacific oyster ether amino phospholipids by normal-phase liquid chromatography/negative-ion electrospray ionization and quadrupole/multiple-stage linear ion-trap mass spectrometry, Anal Chim Acta., 735: 76-89, 2012.
Kim et al., Synthesis of Structured Phosphatidylcholine Containing n-3 PUFA Residues via Acidolysis Mediated by Immobilized Phospholipase A1, J Am Oil Chem Soc, 87:1293-1299, 2010.
Mansbach, The Origin of Chylomicron Phosphatidylcholine in the Rat, The Journal of Clinical Investigation vol. 60, 111-420, 1977.
Adlercreutz et al., A Simple HPLC Method for the Simultaneous Analysis of Phosphatidylcholine and Its Partial Hydrolysis Products 1- and 2-Acyl Lysophosphatidylcholine, JAOCS, vol. 78, No. 10, 1007-1011, 2001.
Winther et al., Elucidation of Phosphatidylcholine Composition in Krill Oil Extracted from Euphausia superba, Lipids (2011) 46:25—36.
Kohan et al., Lymphatics in intestinal transport of nutrients and gastrointestinal hormones, Ann. N.Y. Acad. Sci. ISSN 0077-8923, 2010.
Tall et al., Metabolic Fate of Chylomicron Phospholipids and Apoproteins in the Rat, J. Clin. Invest., vol. 64, 977-989, 1979.
Green et al., Rat Intestine Secretes Discoid High Density Lipoprotein, The Journal of Clinical Investigation vol. 61, 528-534, 1978.
Subbaiah et al., Incorporation profiles of conjugated linoleic acid isomers in cell membranes and their positional distribution in phospholipids, Biochim Biophys Acta. 2011,1811(1): 17—24.
Bazan et al., Docosahexaenoic Acid Signalolipidomics in Nutrition: Significance in Aging, Neuroinflammation, Macular Degeneration, Alzheimer's, and Other Neurodegenerative Diseases, Annu. Rev. Nutr. 2011. 31:321—51.
Tou et al., Different sources of omega-3 polyunsaturated fatty acids affects apparent digestibility, tissue deposition, and tissue oxidative stability in growing female rats, Lipids in Health and Disease 2011, 10:179.
Levy et al., Caco-2 cells as a model for intestinal lipoprotein synthesis and secretion, The FASEB Journal, pg. 626-635, 2019.
Chen et al., Regioisomers of Phosphatidylcholine Containing DHA and Their Potential to Deliver DHA to the Brain: Role of Phospholipase Specificities, Lipids (2013) 48:675-686.
Song et al., Genetic Ablation of CD36 Does not Alter Mouse Brain Polyunsaturated Fatty Acid Concentrations, Lipids (2010) 45:291-299.
Kimura et al., Supplementation of DHA-Rich Microalgal Oil or Fish Oil During the Suckling Period in Mildly n—3 Fatty Acid-Deficient Rat Pups, Lipids (2011) 46:1101-1110.
Hirano et al., A simple and precise method for measuring HDL-cholesterol subfractions by a single precipitation allowed by homogenous HDL-cholesterol assay, Journal of Lipid Research vol. 49, 1130-1136, 2008.
Tyagi et al., Interactive actions of Bdnf methylation and cell metabolism for building neural resilience under the influence of diet, Neurobiol Dis., 73: 307-318, 2015.
Simopoulos et al., Essentiality of and Recommended Dietary Intakes for Omega-6 and Omega-3 Fatty Acids, Ann Nutr Metab, 43:127-130, 1999.
Sugasini et al., Enhanced incorporation of docosahexaenoic acid in serum, heart, and brain of rats given microemulsions of fish oil, Mol Cell Biochem, 382:203-216, 2013.
Lo Van et al., Mechanisms of DHA transport to the brain and potential therapy to neurodegenerative diseases, Biochimie 130, 163-167, 2016.
Lamaziere et al., Differential distributionofDHA-phospholipidsinratbrainafterfeeding: A lipidomicapproach, Prostaglandins, Leukotrienes and Essential Fatty Acids 84, 7-11, 2011.
Gá zquez et al., Docosahexaenoic acid supplementation during pregnancy as phospholipids did not improve the incorporation of this fatty acid into rat fetal brain compared with the triglyceride form, Nutrition Research 37, 78-86, 2017.
Colin et al., Activation of intestinal peroxisome proliferator-activated receptor-αincreases high-density lipoprotein production, European Heart Journal 34, 2566-2574, 2013.
Bemoud-Hubac et al., Specific uptake of DHA by the brain from a structured phospholipid, AceDoPC, OCL 2017, 24 (2), D205.
Sugasini et al., Dietary docosahexaenoic acid (DHA) as lysophosphatidylcholine, but not as free acid, enriches brain DHA and improves memory in adult mice, Scientific Reports 7: 11263, pg. 1-11.
Wu et al., The Salutary Effects of DHA Dietary Supplementation on Cognition, Neuroplasticity, and Membrane Homeostasis after Brain Trauma, Journal of Neurotrauma 28:2113-2122, 2011.
Calder, Omega-3 Fatty Acids and Inflammatory Processes, Nutrients, 2, 355-374, 2010.
Thies et al., Unsaturated Fatty Acids Esterified in 2-Acyl-1-Lysophosphatidylcholine Bound to Albumin Are More Efficiently Taken up by the Young Rat Brain than the Unesterified Form, Journal of Neurochemislry, pg. 1110-1116, 1992.
Arsenault et al., DHA Improves Cognition and Prevents Dysfunction of Entorhinal Cortex Neurons in 3xTg-AD Mice, PLoS ONE, vol. 6, Issue 2, Pt 1-16, 2011.
Grosso et al., Dietary n-3PUFA, fish consumptionanddepression:Asystematic reviewandmeta-analysisofobservationalstudies, Journal of Affective Disorders 205, 269-281, 2016.
Subbaiah et al., Enhanced incorporation of dietary DHA into lymph phospholipids by altering its molecular carrier, Eliochim Biophys Acta. 2016, 1861(8 Pt A): 723-729.
Youmans et al., APOE4-specific Changes in A Accumulation in a New Transgenic Mouse Model of Alzheimer Disease, Journal of Biological Chemistry vol. 287, No. 50, 41774-41786 , 2012.
Hiratsuka et al., Effect of Dietary Docosahexaenoic Acid Connecting Phospholipids on the Lipid Peroxidation of the Brain in Mice, J Nutr Sci Vitaminol, 54, 501-506, 2008.
Lim et al., Changes in Maze Behavior of Mice Occur after Sufficient Accumulation of Docosahexaenoic Acid in Brain,J. Vutr. 131: 319-324, 2001.
McNamara et al., Selective Deficits in Erythrocyte Docosahexaenoic Acid Composition in Adult Patients with Bipolar Disorder and Major Depressive Disorder, J Affect Disord., 126(1-2): 303-311, 2010.
Petursdottir et al., Effect of Dietary n-3 Polyunsaturated Fatty Acids on Brain Lipid Fatty Acid Composition, Learning Ability, and Memory of Senescence-Accelerated Mouse, Journal of Gerontology: Biological Sciences, vol. 63A, No. 11, 1153-1160, 2008.
Perez et al., DHA diet reduces AD pathology in young APPswe/PS1AE9 transgenic mice: Possible Gender Effects, J Veurosci Res., 88(5): 1026-1040, 2010.
Subbaiah et al., Role of sn-2 Acyl Group of Phosphatidylcholine in Determining the Positional Specificity of Lecithin—Cholesterol Acyltransferase, Biochemistry 33, 13259-13266, 1994.
Wang et al., Regulation of Intestinal Apolipoprotein A-I Synthesis by Dietary Phosphatidylcholine in Newborn Swine, Lipids, vol. 36, No. 7, pg. 683-687, 2001.
Legarde et al., Lysophosphatidylcholine as a Preferred Carrier Form of Docosahexaenoic Acid to the Brain, Journal of Molecular Neuroscience, vol. 16, pg. 201-204, 2001.
Plükthun et al., Acyl and Phosphoryl Migration in Lysophospholipids: Importance in Phospholipid Synthesis and Phospholipase Specificity, Biochemistry, 21, 1743-1750, 1982.
Arterburn et al., In vitro genotoxicity testing of Arasco and Dhasco oils, Food and Chemical Toxicology 38, pg. 71-976, 2000.
Bligh et al., A Rapid Method of Total Lipid Extraction and Purification, The National Research Council of Canada, vol. 37, No. 8, 911-917, 1959.

(56) References Cited

OTHER PUBLICATIONS

Subbaiah et al., Evidence for altered positional specificity of Lcat in vivo: studies with docosahexaenoic acid feeding in humans, Journal of Lipid Research vol. 45, pg. 2245-2251, 2004.
Saito et al., Dose-Response Effect of Dietary Docosahexaenoic Acid on Fatty Acid Profiles of Serum and Tissue Lipids in Rats, J. Agric. Food Chem., 46, 184-193, 1998.
Lin et al., Altered essential fatty acid metabolism and composition in rat liver, plasma, heart and brain after microalgal DHA addition to the diet, Journal of Nutritional Biochemistry 22, 758-765, 2011.
Nguyen et al., Mfsd2a is a transporter for the essential omega-3 fatty acid docosahexaenoic acid, Nature, vol. 509, pg. 503-518, 2014.
Lukiw et al., Docosahexaenoic Acid and the Aging Brain, J. Nutr. 138: 2510-2514, 2008.
Barney et al., Lipase-Catalyzed Synthesis of Lysophospholipids in a Continuous Bioreactor, Jaocs, vol. 71, No. 1, 93-96, 1994.
Yang et al., Inhibition of endothelial lipase activity by sphingomyelin in the lipoproteins, Lipids., 49(10): 987-996, 2014.
Guemez-Gamboa et al., Inactivating mutations in MFSD2A, required for omega-3 fatty acid transport in brain, cause a lethal microcephaly syndrome, Nature Genetics vol. 47, No. 7, pg. 809-815, 2015.
Tall et al., Metabolic Fate of Chylomicron Phospholipids and Apoproteins in the Rat, J Clin Invest., 64(4):977-989, 1979.
Croset et al., Characterization of plasma unsaturated lysophosphatidylcholines in human and rat, Biochem. J., 345, 31-67, 2000.
Alessandri et al., Polyunsaturated fatty acids in the central nervous system: evolution of concepts and nutritional Implications throughout life, Reprod. Nutr. Dev. 44, 509-538, 2004.
Rodrigues et al., Influence of feeding graded levels of canned sardines on the inflammatory markers and tissue fatty acid composition of Wistar rats, British Journal of Nutrition, 112, 309-319, 2014.
Chen et al., Phospholipid and fatty acid specificity of endothelial lipase: Potential role of the enzyme in the delivery of docosahexaenoic acid (DHA) to tissues, Biochimica et Biophysica Acta 1771, 1319-1328, 2007.
Yang et al., Regulation of hepatic lipase activity by sphingomyelin in plasma lipoproteins, Biochim Biophys Acta., 1851 (10): 1327-1336, 2015.
Rahman et al., The verylowdensitylipoproteinreceptorisnotnecessaryformaintaining brain polyunsaturatedfattyacidconcentrations, Prostaglandins, Leukotrienes and Essential Fatty Acids 82 141-145, 2010.
Chen et al., The low density lipoprotein receptor is not necessary for maintaining mouse brain polyunsaturated fatty acid concentrations, Journal of Lipid Research vol. 49, pg. 147-152, 2008.
Gesquiere et al., Role of Group IIa and Group V Secretory Phospholipases A2 in the Metabolism of Lipoproteins. Substrate Specificities of the Enzymes and the Regulation of Their Activities by Sphingomyelin, Biochemistry, 41, 4911-4920, 2002.
Zilversmit, The surface coat of chylomicrons: lipid chemistry, Journal of Lipid Research vol. 9, 180-187, 1968.
Sethom et al., Polyunsaturatedfattyacidsdeficitsareassociatedwithpsychoticstate and negativesymptomsinpatientswithschizophrenia, Prostaglandins, Leukotrienes and Essential Fatty Acids 83, 131-136, 2010.

Sato et al., LXR Agonist Increases the Lymph HDL Transport in Rats by Promoting Reciprocally Intestinal ABCA1 and apo A-I mRNA Levels, Lipids, 43:125-131, 2008.
Cunnane et al., Docosahexaenoic acid homeostasis, brain aging and Alzheimer'sdisease: Can we reconcile the evidence?, Prostaglandins, Leukotrienes and Essential Fatty Acids 88, pg. 61-70, 2013.
Milling et al., Collection of lymph-borne dendritic cells in the rat, Nature Protocols, vol. 1, No. 5, pg. 2263-2270, 2006.
Rossmeisl et al., Metabolic Effects of n-3 PUFA as Phospholipids Are Superior to Triglycerides in Mice Fed a High-Fat Diet: Possible Role of Endocannabinoids, PLoS One, vol. 7, Issue 6, pg. 1-13, 2012.
Neggers et al., Mental retardation is associated with plasma omega-3 fatty acid levels and the omega-3/omega-6 ratio in children, Asia Pac J Clin Nutr,18 (1): 22-28, 2009.
Smink et al., Linoleic and a-linolenic acid as precursor and inhibitor for the synthesis of long-chain polyunsaturated fatty acids in liver and brain of growing pigs, Animal, 6:2, pp. 262-270, 2012.
Chen, Lipids Based Docosahexaenoic Acid (DHA) Carriers and their Ability to Deliver DHA to the Brain: A Prospective Outline, Chen, J Bioequiv Availab, 5:2, 2013.
Kazachkov et al., Substrate Preferences of a Lysophosphatidylcholine Acyltransferase Highlight Its Role in Phospholipid Remodeling, Lipids, 43:895-902, 2008.
DeMar Jr. et al., α-Linolenic acid does not contribute appreciably to docosahexaenoic acid within brain phospholipids of adult rats fed a diet enriched in docosahexaenoic acid, Journal of Neurochemistry, 94, 1063-1076, 2005.
Nilsson, Intestinal Absorption of Lecithin and Lysolecithin by Lymph Fistula Rats, Biochim. Biophys. Acta, 152, pg. 379-390, 1968.
Zierenberg et al., Intestinal absorption of polyenephosphatidylcholine in man, Journal of Lipid Research , pg. 1136-1142, 1982.
Gao et al., Aging decreases rate of docosahexaenoic acid synthesis-secretion from circulating unesterified α-linolenic acid by rat liver, AGE 35:597-608, 2013.
Singh et al., Role of sphingomyelin and ceramide in the regulation of the activity and fatty acid specificity of group V secretory phospholipase A2, Arch Biochem Biophys., 459(2): 280-287, 2007.
Graf et al, Age dependent incorporation of 14C-DHA into rat brain and body tissues after dosing various 14C-DHA-esters, Prostaglandins, Leukotrienes and Essential Fatty Acids 83, pg. 89-96, 2010.
Brunham et al., Intestinal ABCA1 directly contributes to HDL biogenesis in vivo, The Journal of Clinical Investigation, vol. 116, No. 4, pg. 1052-1062, 2006.
Tang et al., Short term effects of different omega-3 fatty acid formulation on lipid metabolism in mice fed high or low fat let, Lipids in Health and Disease, 11:70, pg. 1-8, 2012.
Cansell et al., Marine Lipid-Based Liposomes Increase in vivo FA Bioavailability, Lipids, vol. 38, No. 5 pg. 551-559, 2003.
Lukiw et al., Docosahexaenoic Acid and the Aging Brain, American Society for Nutrition, pg. 2510-2515, 2008.
Scow et al., Incorporation of Dietary Lecithin and Lysolecithin into Lymph Chylomicrons in the Rat, The Journal of Biological Chemistry, vol. 242, No. 21, pg. 4919-4924, 1967.

\* cited by examiner

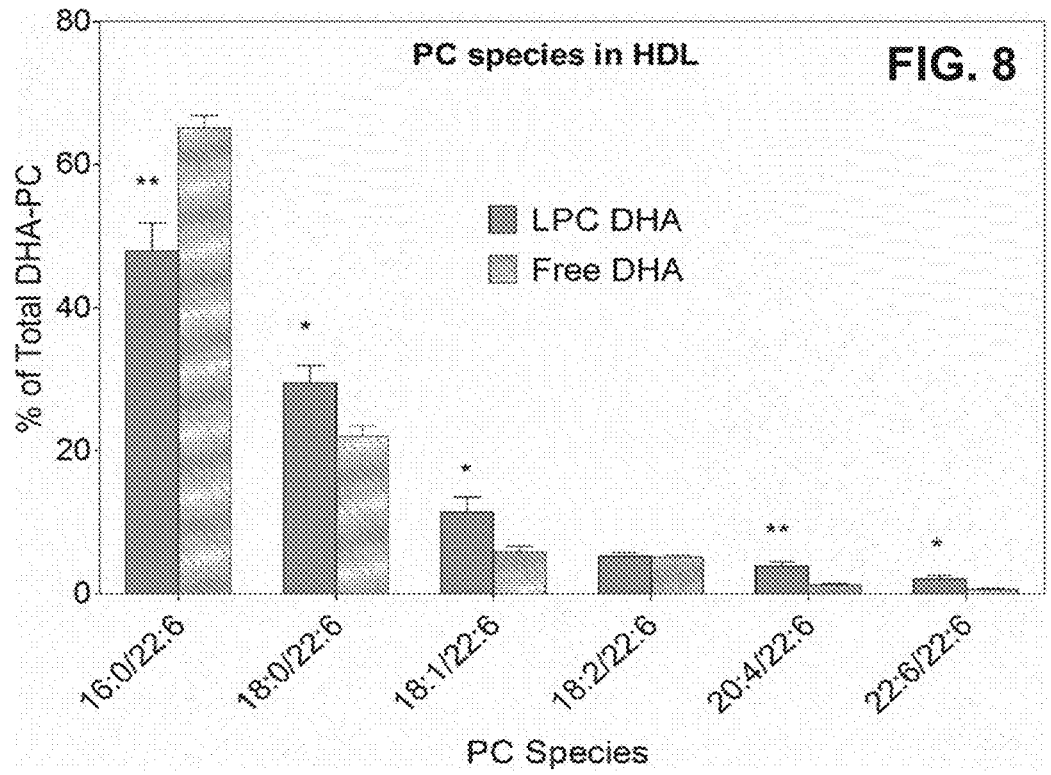
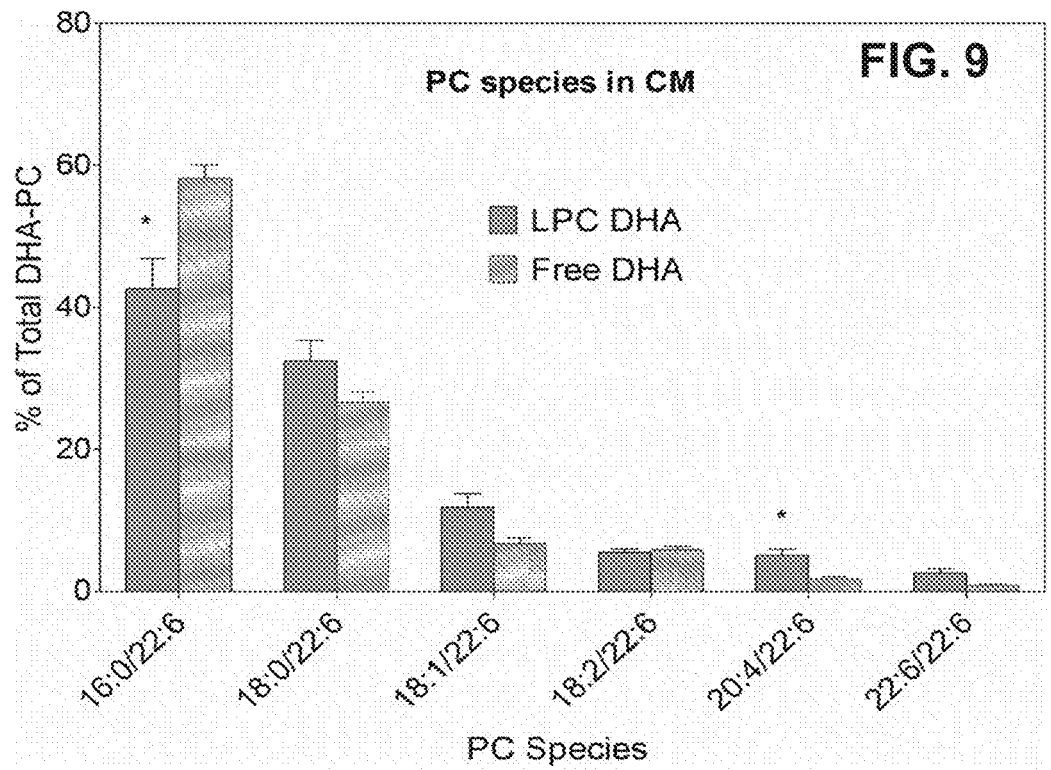

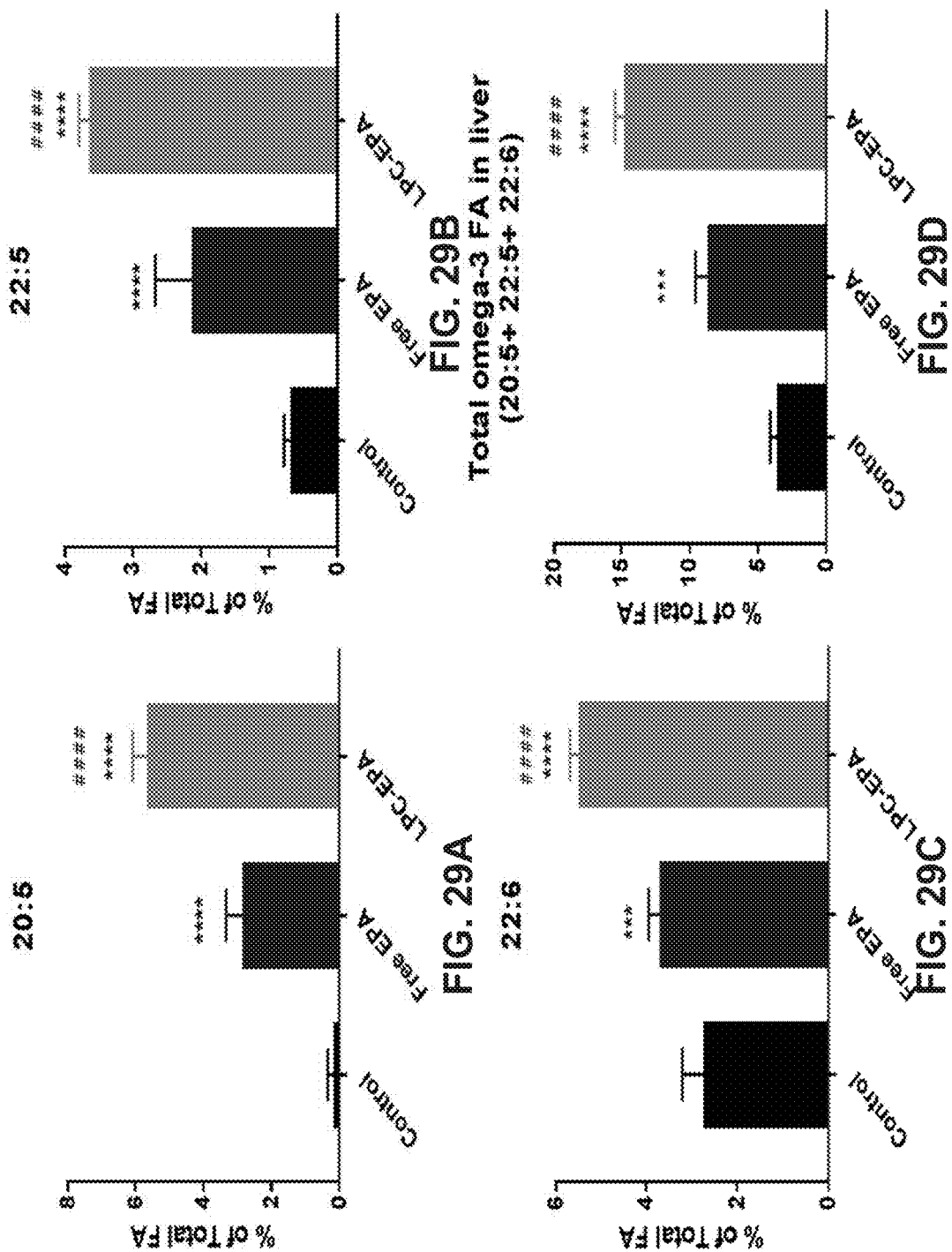

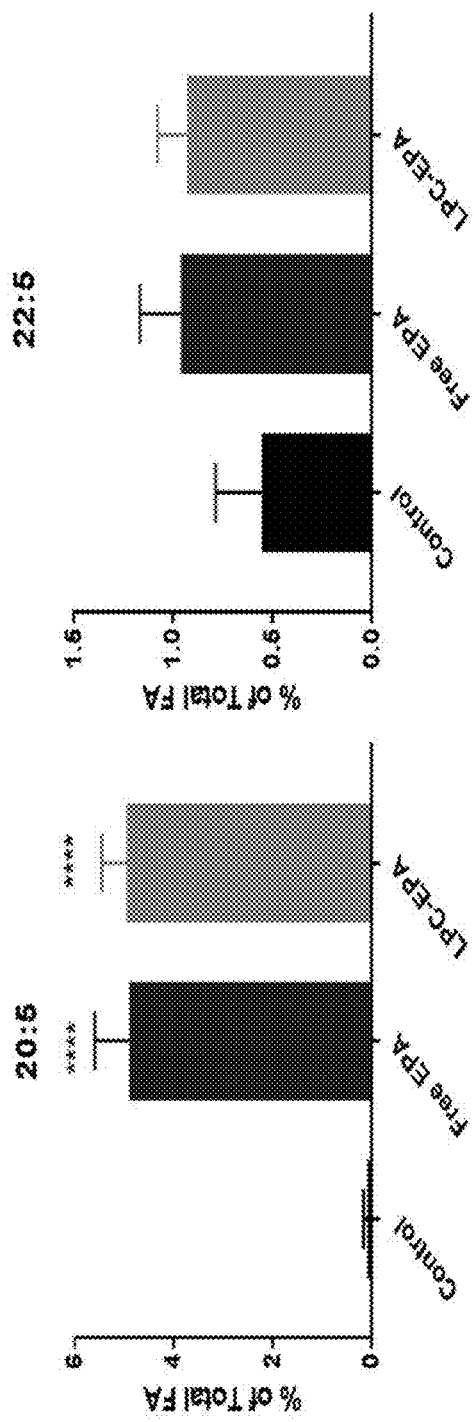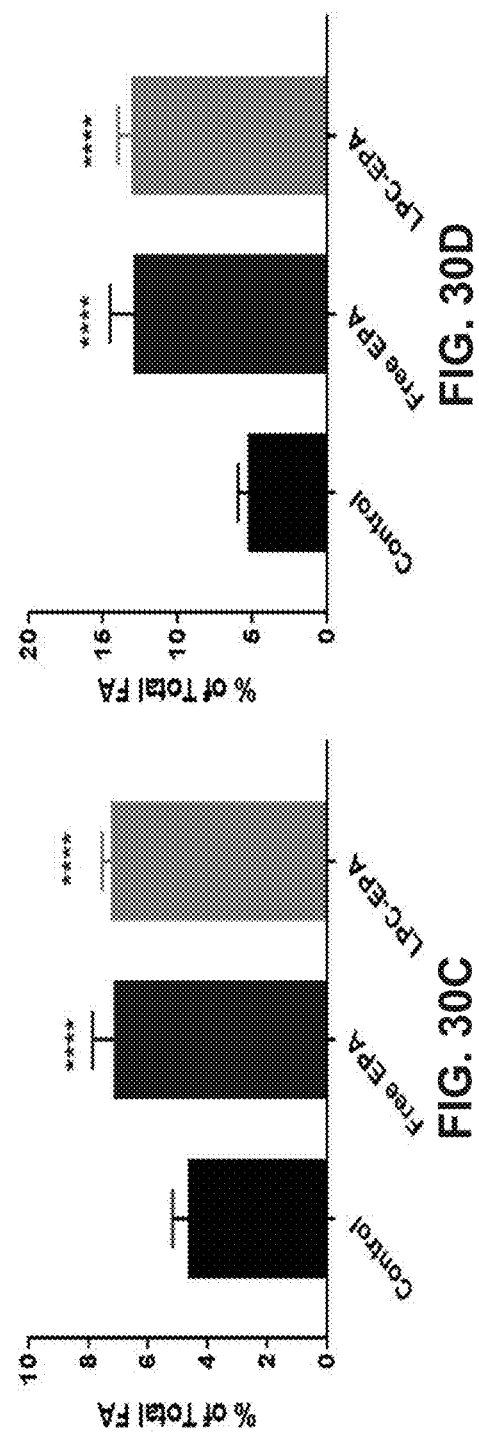

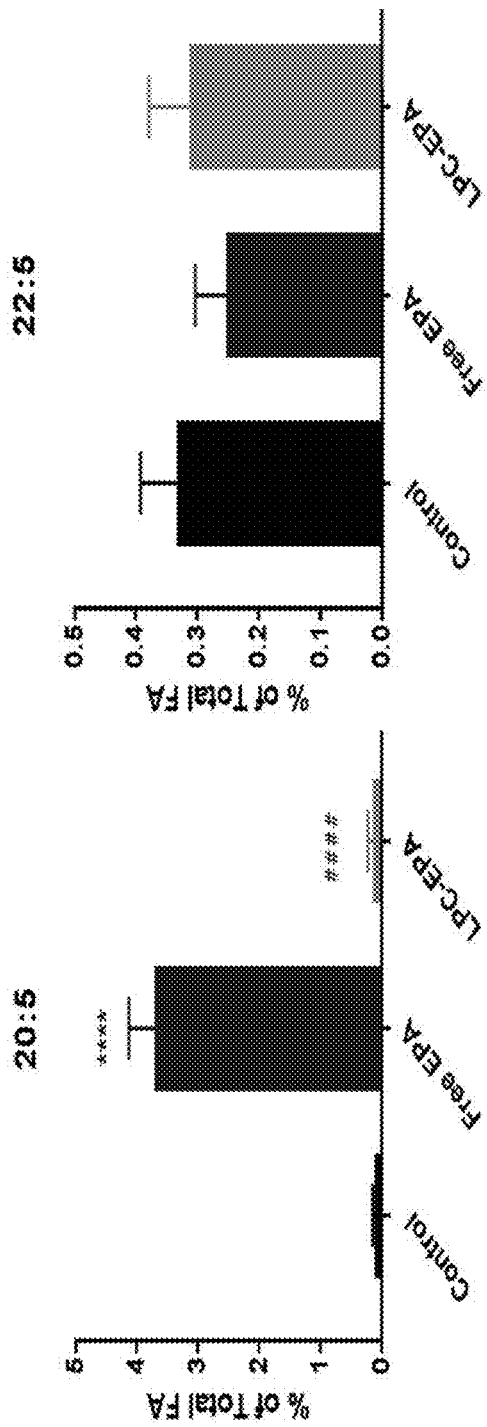
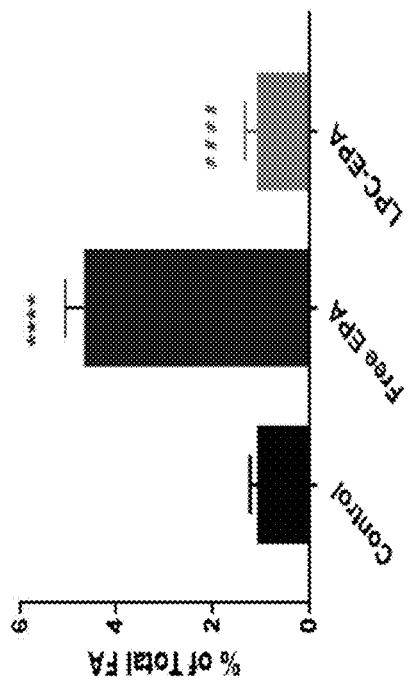
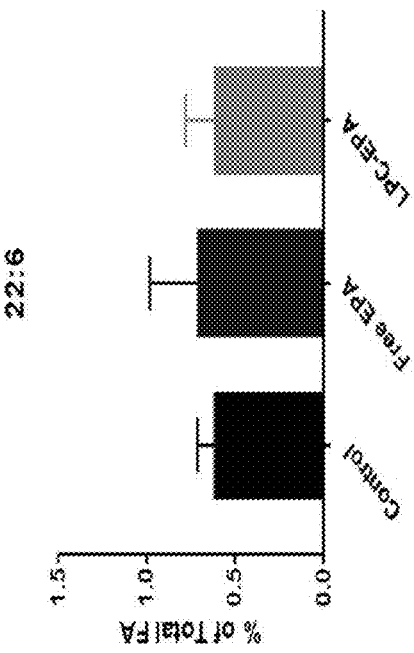
FIG. 31A, FIG. 31B, FIG. 31C, FIG. 31D
Total omega-3 FA in adipose tissue (20:5+22:5+22:6)

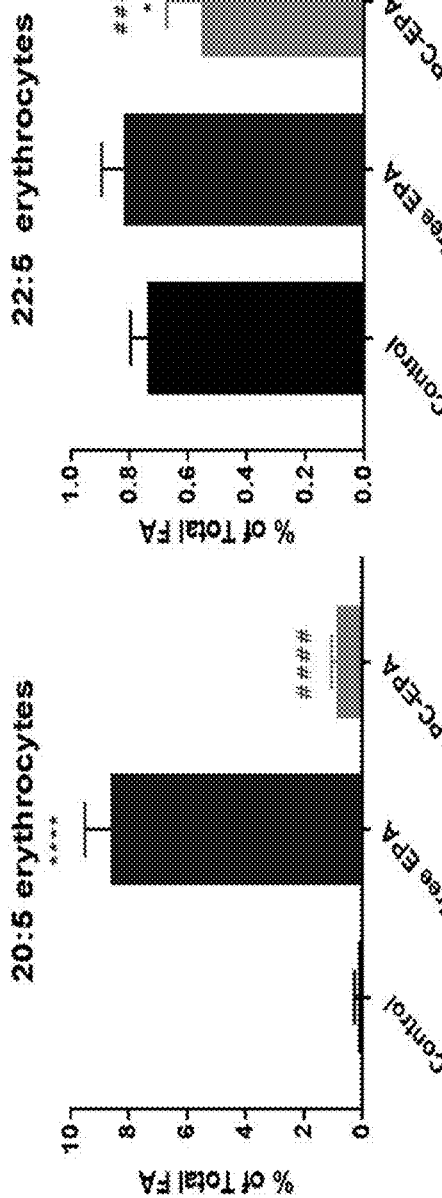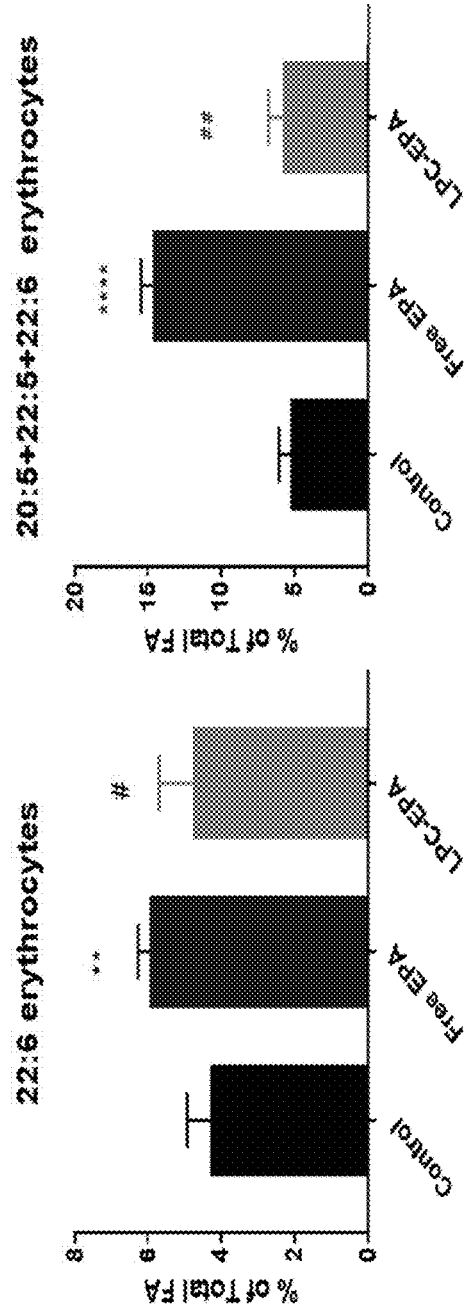

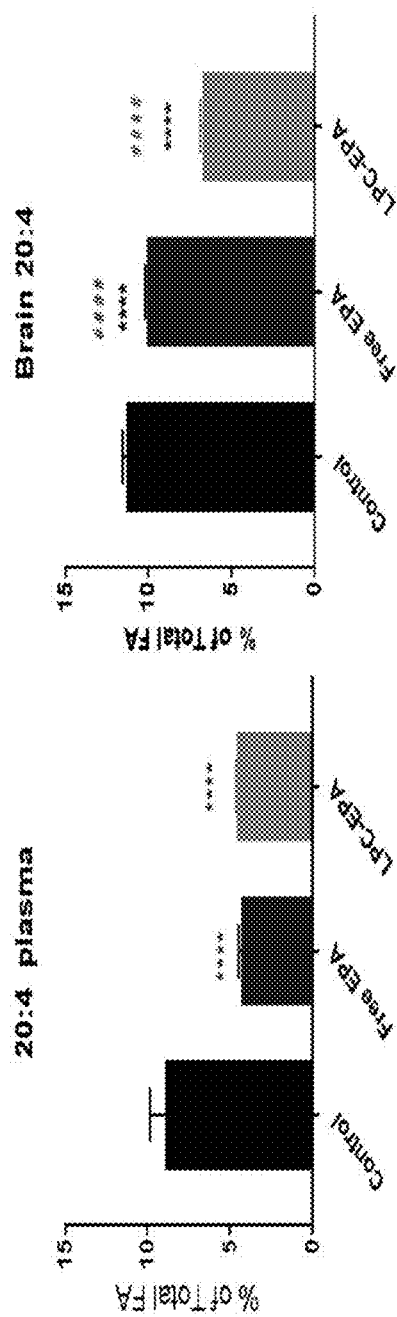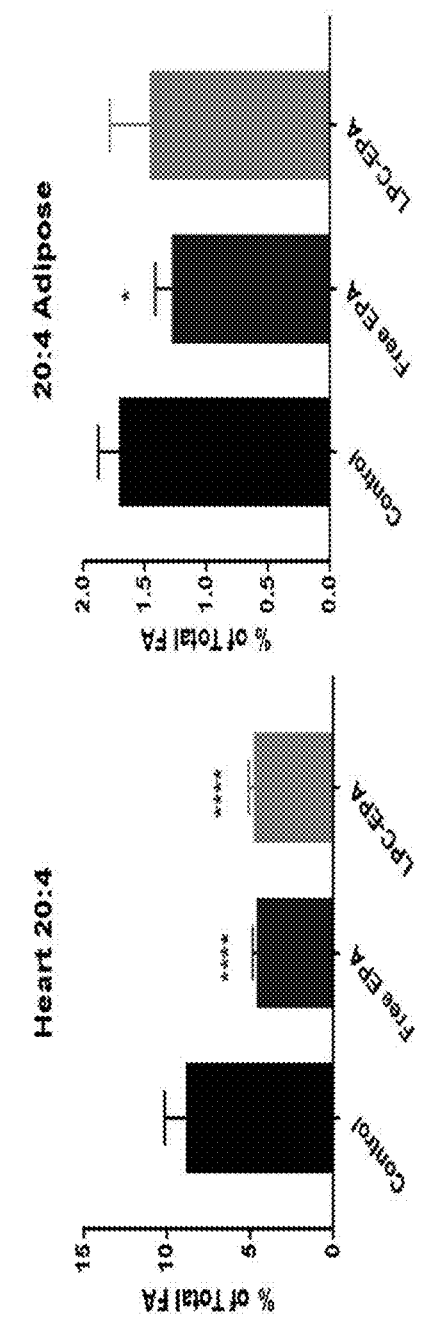
FIG. 33A
FIG. 33B
FIG. 33C
FIG. 33D

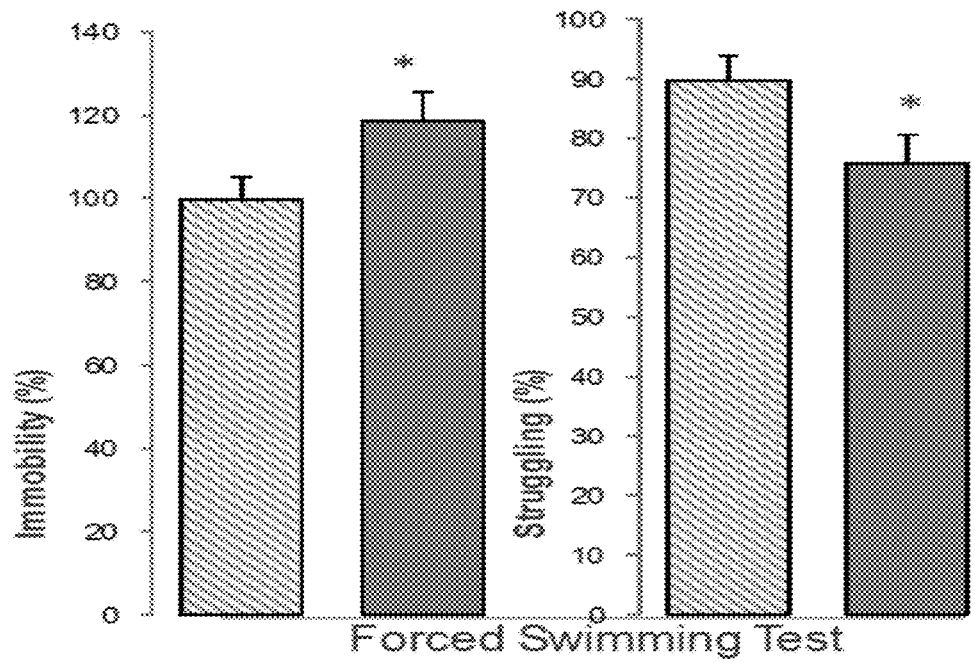
FIG. 35A  FIG. 35B
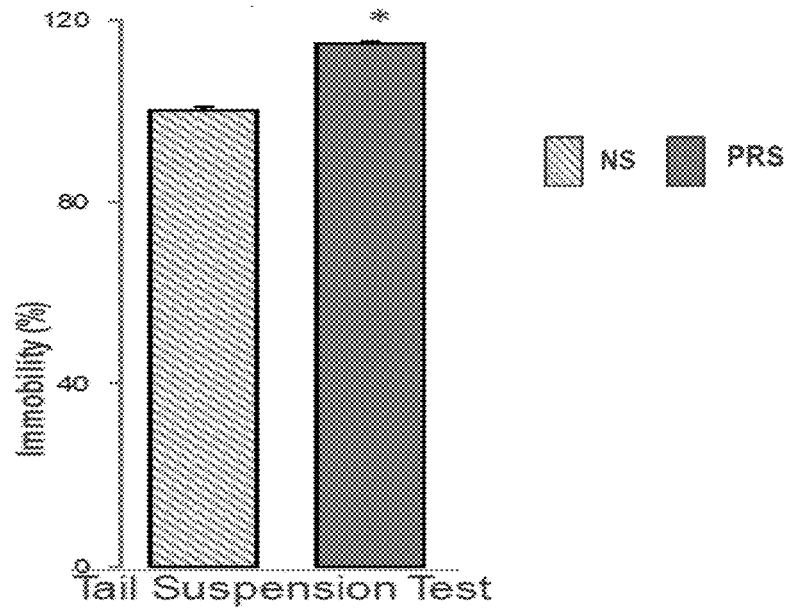
FIG. 35C

METHODS AND COMPOSITIONS FOR ENRICHING DHA LEVELS IN THE BRAIN

CROSS-REFERENCE TO RELATED APPLICATIONS

This application claims the benefit of and priority to U.S. Provisional Patent Application No. 62/504,326, filed on May 10, 2017, entitled "METHODS AND COMPOSITIONS FOR ENRICHING DHA LEVELS IN THE BRAIN," the contents of which is incorporated by reference herein in its entirety.

STATEMENT REGARDING FEDERALLY SPONSORED RESEARCH

This invention was made with government support under grant numberS HL068585 and AT008457 awarded by the National Institutes of Health. The government has certain rights in the invention.

BACKGROUND

Alzheimer's, depression and other neurological diseases and disorders are significant health problems today. As such there exists a need for additional and/or improved compositions and methods to prevent and/or treat such diseases and disorders.

SUMMARY

Described herein are DHA- or EPA-containing phospholipid compounds, formulations thereof, methods of making the compounds and formulations thereof, and uses of the compounds and formulations.

In some embodiments described herein are compounds according to Formula 1

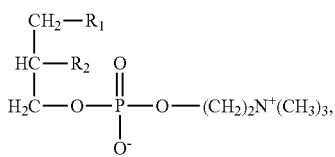

Formula 1 wherein $R_1$ can be —OH, eicosapentaenoic acid (EPA), or docosahexaenoic acid (DHA), and wherein $R_2$ can be —OH or EPA. $R_2$ can be OH. $R_1$ can be OH and $R_2$ is EPA.

In some embodiments, the formulation can include a compound according to Formula 1

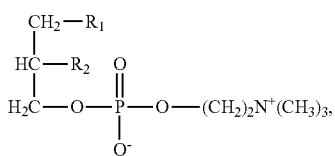

Formula 1 wherein $R_1$ can be —OH, eicosapentaenoic acid (EPA), or docosahexaenoic acid (DHA), and wherein $R_2$ can be —OH or EPA; and a carrier. In some formulations, the compound according to Formula 1 can be encapsulated by a micelle, forms a micelle, and/or can be incorporated into the membrane of a vesicle. The micelle or vesicle micelle further include a cholesterol, phosphotidylcholine, a fatty acid, or any combination thereof. The amount of the compound according to formula 1 can be an effective amount. The amount of the compound according to Formula 1 can be an amount effective to treat depression. The amount of the compound according to Formula 1 can be an amount effective to treat a neurological disease or disorder. The neurological disease or disorder can be Alzheimer's disease, Parkinson's, or a traumatic brain injury. The amount of the compound according to Formula 1 can be an amount effective to enhance the cognitive function in a subject. The amount of the compound according to Formula 1 can be an amount effective to increase the levels of DHA, EPA, or DHA and EPA in the brain of a subject. The formulation can be a dietary supplement. The formulation can be a functional food item.

Also, in some embodiments, described herein are methods that can include the step of administering an amount of a compound according to Formula 1

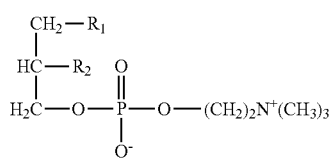

Formula 1 to a subject, wherein $R_1$ can be —OH, eicosapentaenoic acid (EPA), or docosahexaenoic acid (DHA), and wherein $R_2$ can be —OH or EPA. The subject can have or can be suspected of having a neurological disease or disorder. The neurological disease or disorder can be depression, Alzheimer's, Parkinson's, or a traumatic brain injury. The amount of the compound according to Formula 1 can be an amount effective to increase the amount of DHA, EPA, or DHA and EPA in the brain of the subject. The amount of the compound according to Formula 1 can be an amount effective to treat a neurological disease or disorder. The neurological disease or disorder can be depression, Alzheimer's, Parkinson's, or a traumatic brain injury.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 3 can demonstrate the total amount of DHA absorbed in 6 h in individual experiments. Although there were individual variations among the animals in each group, the mean values were not significantly different between the two groups. The dotted line is the mean value and the solid lines are SEM. N=8 for both groups. The total amount of DHA infused in micelle was 24 µmoles (7.88 mg) in both groups.

FIG. 8 shows a graph that can demonstrate the molecular species of DHA-containing PC in lymph HDL. The molecular species composition of PCs that contained DHA was determined by MRM, as described in Example 1 (e.g. Tables-12). The position occupied by DHA was not determined. The values shown are mean±SEM of 9 experiments for LPC-DHA, and 7 experiments for free DHA. *p<0.05, **p<0.005, Free DHA vs LPC-DHA (unpaired t test).

FIG. 9 shows a graph that can demonstrate the molecular species of DHA-containing PC in CM. The molecular species composition of PCs containing DHA was determined by MRM, as described in Example 1 (e.g. Tables 1-2). The position occupied by DHA was not determined. The values shown are mean±SEM of 9 experiments for LPC-DHA, and 7 experiments for free DHA. *p<0.05, Free DHA vs LPC-DHA (unpaired t test).

FIGS. 29A-29D show graphs that can demonstrate the omega 3 fatty acids in liver after feeding free EPA or LPC-EPA at 1 mg EPA/day for 15 days. Both free EPA and LPC-EPA increased liver omega 3 fatty acids, although LPC-EPA was more efficient. In contrast to the brain, there was significant accumulation of EPA and DPA, in addition to DHA. * Different from control; # different from free EPA.

FIGS. 30A-30D show graphs that can demonstrate the omega 3 fatty acids in heart after feeding free EPA or LPC-EPA at 1 mg EPA/day for 15 days. In the heart, free EPA and LPC-EPA were equally efficient in enriching the total omega 3 fatty acids. The accumulation of EPA was greater than in other tissues, suggesting a lower conversion to DPA and DHA. * Different from control; # different from free EPA.

FIGS. 31A-31D show graphs that can demonstrate the omega 3 fatty acids in adipose tissue after feeding free EPA or LPC-EPA at 1 mg EPA/day for 15 days. The omega 3 fatty acid content of adipose tissue was enriched more with free EPA than with LPC-EPA. There was, however, no conversion of EPA into DPA or DHA in this tissue, since all the increase was due to EPA. * Different from control; # different from free EPA.

FIGS. 32A-32D show graphs that can demonstrate the omega 3 fatty acids in erythrocytes after feeding free EPA or LPC-EPA at 1 mg EPA/day for 15 days. Only free EPA increased the omega 3 fatty acids and no conversion to DPA or DHA was observed. * Different from control; # different from free EPA.

FIGS. 33A-33F show graphs that can demonstrate arachidonic acid (20:4) in various tissues after feeding free EPA or LPC-EPA at 1 mg EPA/day for 15 days. In all tissues, the concentration of arachidonic acid was decreased after feeding either free EPA or LPC-EPA. The decrease was similar with LPC-EPA and free EPA except in the brain where LPC-EPA decreased it more. * Different from control; # different from free EPA.

FIGS. 35A-35E show graphs that can demonstrate pre-natal stress induces depression and anxiety-like behavior in adult mice. *p<0.05 vs. NS mice as determined by Student's t-test, n=10 per group. PRS=pre-natal restraint stress. NS=not stressed.

DETAILED DESCRIPTION

Figure 1:
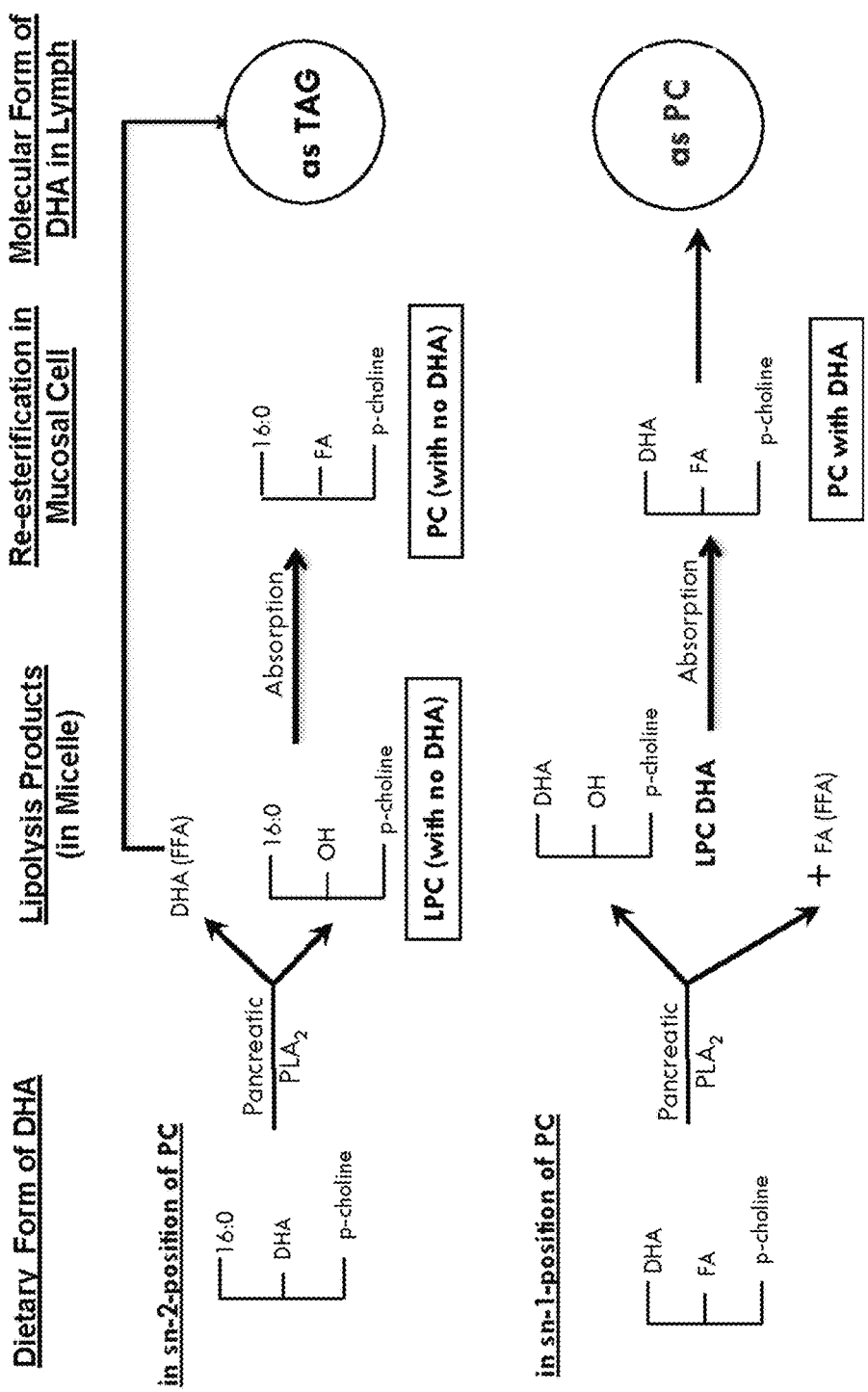
FIG. 1 shows a scheme of the absorption of TAG-DHA, sn-2 DHA PC, and sn-1 DHA PC.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

As used herein, the following abbreviations shall have the indicated meanings: DHA for docosahexaenoic acid; BBB for blood brain barrier, CM for chylomicrons; FAME for fatty acid methyl esters; LPC for lysophosphatidylcholine; MAG for monoacylglycerol; MRM for multiple reaction monitoring; PC for phosphatidylcholine; and TAG for triacylglycerol.

As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition theerivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "agent" can refer to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "control" can refer to an alternative subject or sample used in an experiment for comparison purpose and included to minimize or distinguish the effect of variables other than an independent variable.

As used herein, "dose," "unit dose," or "dosage" can refer to physically discrete units suitable for use in a subject, each unit containing a predetermined quantity of the DHA- or EPA-containing phospholipid, micelle thereof, and/or formulation thereof calculated to produce the desired response or responses in association with its administration.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "positive control" can refer to a "control" that is designed to produce the desired result, provided that all reagents are functioning properly and that the experiment is properly conducted.

As used herein, "preventative" and "prevent" can refer to hindering or stopping a disease or condition before it occurs, even if undiagnosed, or while the disease or condition is still in the sub-clinical phase.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "DHA" means (4Z,7Z,10Z,13Z,16Z,19Z)-docosa-4,7,10,13,16,19-hexaenoic acid.

As used herein, the term "phospholipid" can be abbreviated PL and can include phosphatidylcholine, phosphatidyl ethanolamine, phosphatidylserine, phosphatidyl inositol and lysophosphatidylcholine.

As used herein, the term "DHA PL" can refer to a phospholipid molecule in which a fatty acid, such as at the sn-1 or sn-2 position of the phodpholipid molecule, can be replaced with DHA.

As used herein, the term "Sn-1 DHA PL" can refer to a phoshopholipid molecule in which the fatty acid at the sn-1 position is replaced with DHA.

As used herein, the term "Sn-2 DHA PL" can refer to a phoshopholipid molecule in which the fatty acid at the sn-2 position is replaced with DHA.

As used herein, "Sn-1 DHA PC" means a phosphatidylcholine molecule in which the fatty acid at the sn-1 position is replaced with DHA.

As used herein, "DHA-LPC" means a lysophosphatidylcholine molecule wherein the fatty acid at the sn-1 or sn-2 position is replaced with DHA. In certain embodiments, the DHA is at the sn-1 position. In other embodiments, the DHA is at the sn-2 position.

As used herein, "EPA" refers to eicosapentaenoic acid (including 20:5, n-3).

As used herein, "sn-1 EPA PC" can mean a phosphatidylcholine molecule in which the fatty acid at the sn-1 position is replaced with EPA.

As used herein, "sn-2 EPA PC" can mean a phosphatidylcholine molecule in which the fatty acid at the sn-2 position is replaced with EPA.

As used herein, the term "EPA PL" can refer to a phospholipid molecule in which a fatty acid, such as at the sn-1 or sn-2 position of the phodpholipid molecule, can be replaced with EPA.

As used herein, the term "Sn-1 EPA PL" can refer to a phoshopholipid molecule in which the fatty acid at the sn-1 position is replaced with EPA.

As used herein, the term "Sn-2 EPA PL" can refer to a phoshopholipid molecule in which the fatty acid at the sn-2 position is replaced with EPA.

As used herein, "EPA-LPC" can refer to a lysophosphatidylcholine molecule wherein the fatty acid at the sn-1 or sn-2 position is replaced with EPA. In certain embodiments, the EPA is at the sn-1 position. In other embodiments, the EPA is at the sn-2 position.

As used herein, "treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, or slowing progression of one or more symptoms of the disease or disorder.

As used herein, "subject" refers to a warm blooded animal such as a mammal, preferably a human, or a human child, which is afflicted with, or has the potential to be afflicted with one or more diseases and disorders described herein. Subject as used herein also contemplates an offspring in utero where a composition according to the invention is administered to the mother and is subsequently absorbed by the offspring.

As used herein, the terms "amount effective," "effective amount" or a "therapeutically effective amount" refer to an amount of sn-2 DHA phospholipid, sn-1 DHA phospholipid, sn-1 EPA phospholipid, sn-2 EPA phospholipid, EPA-LPC, DHA-LPC or a composition or formulation containing an sn-1 DHA phospholipid, sn-1 EPA phospholipid, sn-2 EPA phospholipid, EPA-LPC, and/or DHA-LPC sufficient to achieve the stated desired result, for example, increasing levels of EPA and/or DHA in a subject's brain comprising or treating neurological diseases such as depression, Alzheimer's, Parkinson's, and traumatic brain injury. The amount of sn-1 DHA phospholipid or DHA-LPC which constitutes an "effective amount" or "therapeutically effective amount" can vary depending on the severity of the disease, the condition, weight, or age of the patient to be treated, the frequency of dosing, or the route of administration, but can be determined routinely by one of ordinary skill in the art. A clinician can titer the dosage or route of administration to obtain the optimal therapeutic effect. Typical dosages range from about 0.1 µg/kg to up to about 100 mg/kg or more, depending on the factors mentioned above. In certain embodiments, the dosage can range from 0.1 µg/kg up to about 100 mg/kg, or 1 µg/kg up to about 100 mg/kg, or 5 µg/kg up to about 100 mg/kg.

As used herein, "micelle" (plural micelles, micella, or micellae) refers to an aggregate of molecules that have assembled into an approximately spherical core/shell architecture, and are suspended in an aqueous phase. A typical micelle in aqueous solution forms an aggregate with the hydrophilic "head" regions in contact with surrounding solvent and/or in contact with the polar region of one or more surface active agent(s), sequestering the hydrophobic regions in the micelle center. Micelles are approximately spherical in shape. In certain embodiments, said surface active agent is selected from the group consisting of nonionic surface active agents, cationic surface active agents, anionic surface active agents, zwitterionic surface active agents, or combinations thereof.

As used herein, "self-micellizes" refers to the process in which micelles are formed in an aqueous medium without the introduction of energy, including agitation or shearing. In certain embodiments, the composition self-micellizes in an aqueous medium. In certain other embodiments, the aqueous medium is water.

Discussion

There are two important omega 3 fatty acids in human diets that are essential for the normal development and function of the brain among other things. These two omega 3 fatty acids are docosahexaenoic acid (DHA) and eicosapenteanoic acid (EPA). Prior preliminary studies have showed that supplementation with these omega 3 fatty acids are promising for the treatment of various diseases and disorders, including brain diseases and disorders. However, these studies have failed to translate into effective treatments. The failure of the preliminary studies and supplementation with DHA and EPA (including dietary supplementation) to translate into effective treatments can be due, inter alia, problems with the deliver and availability of DHA and EPA to and in the brain.

With that said, described herein compounds and formulations that can be or contain a docosahexaenoic acid-phospholipid (DHA-PL), such as docosahexaenoic acid-lysophosphatidylcholine (DHA-LPC) and/or an eicosapenteanoic acid-phospholipid (EPA-PL), such as eicosapenteanoic acid-lysophosphatidylcholine (EPA-LPC). In some embodiments, the DHA-PL and/or EPA-PL can be incorporated into a micelle. In some embodiments, the DHA or the EPA can be incorporated in the PL in the sn-1 or sn-2 position. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

DHA- or EPA-Containing Phospholipid Compounds, Micelles, and Formulations Thereof DHA- or EPA-Containing Phospholipid Compounds and Micelles Thereof DHA- or EPA-Containing Phospholipid Compounds Described herein are DHA- or EPA-containing phospholipid compounds. The DHA- or EPA-containing compounds can be DHA-PL, DHA-PC, DHA-LPC, EPA-PL, EPA-PC, or EPA-LPC. The DHA- or EPA-containing compounds can be PL, including without limitation, PC or LPC, that has the sn-1 or sn-2 fatty acid replaced with DHA or EPA. In some embodiments, a compound can be according to Formula 1

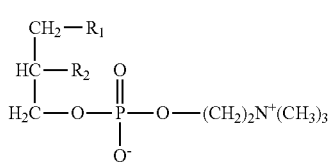

Formula 1 where $R_1$ can be —OH, EPA, or DHA, and where $R_2$ can be —OH or EPA. In some embodiments, the compound can be sn-1 DHA-LPC. In some embodiments, the compound can be sn-1 EPA-LPC. In some embodiments, the compound can be sn-2 EPA-LPC. The compound can be sn-1 DHA-PC, sn-2 DHA-PC, sn-1 EPA-PC or sn-2 EPA PC.

In some embodiments, the compound can be according to Formula 2,

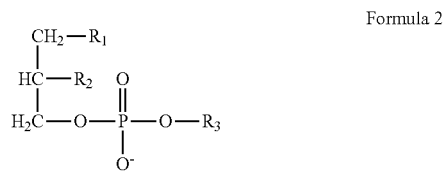

Formula 2 where $R_1$ can be —OH, EPA, or DHA, where $R_2$ can be —OH, DHA, or EPA, where $R_3$ can be choline, ethanolamine, serine, or inositol, and where at least one of $R_1$ or $R_2$ is DHA or EPA.

The sn-2 compounds described herein can be made by replacing the sn-2 fatty acid of PC or LPC with DHA or EPA. The sn-1 compounds described herein can be made by replacing the sn-2 fatty acid of PC or LPC with DHA or EPA. In some embodiments, the sn-1 compounds are formed from isomerization of its respective sn-2 counterpart. For example, sn-1 DHA-LPC can be formed from isomerizing sn-2 DHA-LPC. Suitable exemplary methodologies and techniques for making such compounds are described in the Examples herein.

Micelles

In some embodiments, the DHA- or EPA-containing phospholipid compounds described herein can be included in micelle. The micelle can be different from the carrier in a formulation described elsewhere herein. For example, the formulation can include a micelle that can include or incorporate a DHA- or EPA-containing phospholipid compound described herein and a carrier. The DHA- or EPA-containing phospholipid as described herein can be included in emulsions pre-formed prior to administration to a subject in need of such administration. Such pre-formed micelles are stable at room temperature.

The micelle can contain one or more DHA- or EPA-containing phospholipid compounds as previously described as well as additional components. Additional components can include, but are not limited to, a cholesterol, PC, a fatty acid, a monoolein, a bile acid, and any combination thereof. The amount of the cholesterol in the micelle can range from 0 to 9.99 wt % of the total micelle composition. The amount of the free fatty acid in the micelle can range from 0 to 10 wt % of the total micelle composition. In some embodiments the free fatty acid is not DHA or EPA. In some embodiments the free fatty acid can be oleic acid. The amount of the monoolein in the micelle can range from 0 to 10 wt % of the total micelle composition. In some embodiments, the bile acid can range from 0-50% of the micelle. The bile acid can be sodium taurocholate. In some embodiments, the micelle can contain, in addition to the DHA- and/or EPA-containing compounds, 2-Monoolein, free oleic acid, egg PC and sodium taurocholate.

The micelles can have an aqueous center. The aqueous center can contain the carrier or other suitable aqueous solution. The aqueous center can be water, an alcohol, or a mixture thereof. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

In certain embodiments, the DHA- or EPA-containing phospholipid compounds and/or micelle components can self-micellize in an aqueous medium. In some embodiments, the aqueous medium is water. In certain embodiments, the DHA- or EPA-containing phospholipid compounds and/or micelle components can described herein self-micellizes in an aqueous medium wherein the micelles have a diameter from about 1 µm to about 10 µm. In certain embodiments, the compositions described herein self-micellizes in an aqueous medium having an acidic pH, wherein the micelles have a diameter from about 1 µm to about 10 µm. In certain other embodiments, the compositions described herein self-micellizes in 0.1N HCL, wherein the micelles have a diameter from about 1 µm to about 10 µm. In certain embodiments, the micelles have an average diameter of about 1, 2, 3, 4, 5, 6, 7, 8, 9, or 10 µm.

The DHA- or EPA-containing phospholipid compounds can be encapsulated by the micelle and/or incorporated into the vesicle membrane. The components of that form the micelle can be formed by self-micellization or self-assembly in an aqueous solution. Suitable methods for micelle formation are described elsewhere herein as well as generally known in the art.

Formulations

The DHA- or EPA-containing phospholipid compounds and micelles thereof described herein can be included in a formulation that, in addition to the compound, can further include a suitable carrier. The carrier can be a pharmaceutically acceptable carrier. The formulation can be a pharmaceutical formulation. The compounds and/or formulations described herein can be administered to a subject. The subject can be a subject in need thereof. The subject can have or be suspected of having a neurological disease or disorder. The neurological disease or disorder can be, without limitation, depression, Alzheimer's disease, Parkinson's, or a traumatic brain injury. The subject can be in need of increased DHA and/or EPA brain levels. The compounds and formulations described herein can be used to treat a neurological disease or disorder in a subject in need thereof. The compounds and formulations described herein can be administered by a suitable route, such as but not limited to oral, infusion, and intravenous. Other suitable routes are described elsewhere herein.

Parenteral Formulations

The DHA- or EPA-containing phospholipid compounds and micelles thereof can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the DHA- or EPA-containing phospholipid compounds and micelles thereof as described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the DHA- or EPA-containing phospholipid compounds and/or micelles thereof.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the DHA- or EPA-containing phospholipid compounds and/or micelles thereof in the desired amount in the appropriate solvent or dispersion medium with one or more of the excipients listed above, as required, followed by filtered sterilization. Dispersions can be prepared by incorporating the various sterilized DHA- or EPA-containing phospholipid compounds and/or micelles thereof into a sterile vehicle which contains the basic dispersion medium and the required other ingredients from those listed above. Sterile powders for the preparation of sterile injectable solutions can be prepared by vacuum-drying and freeze-drying techniques, which yields a powder of the DHA- or EPA-containing phospholipid compounds with or without any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of the DHA- or EPA-containing phospholipid compounds and/or micelles thereof. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

The DHA- or EPA-containing phospholipid compounds and/or micelles thereof as described herein can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the DHA- or EPA-containing phospholipid compounds and/or micelles thereof can be administered as a liquid formulation, such as a solution or suspension, a semi-solid formulation, such as a lotion or ointment, or a solid formulation. In some embodiments, the DHA- or EPA-containing phospholipid compounds can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a nonionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing DHA- or EPA-containing phospholipid compounds and/or micelles thereof as described herein are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing DHA- or EPA-containing phospholipid compounds and/or micelles thereof as described herein are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing DHA- or EPA-containing phospholipid compounds and/or micelles thereof and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing DHA- or EPA-containing phospholipid compounds and/or micelles thereof, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include DHA- or EPA-containing phospholipid compounds and/or micelles thereof as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The DHA- or EPA-containing phospholipid compounds and/or micelles thereof can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing DHA- or EPA-containing phospholipid compounds and/or micelles thereof as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing DHA- or EPA-containing phospholipid compounds and/or micelles thereof as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing DHA- or EPA-containing phospholipid compounds and/or micelles thereof as described herein can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing DHA- or EPA-containing phospholipid and/or micelles thereof as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Dietary Supplements

The DHA- or EPA-containing phospholipid and/or micelles thereof as described herein can be included in a dietary supplement. The dietary supplement can be in pharmaceutical dietary supplement compositions in solid, semi-solid, or liquid dosage forms, such as, for example, tablets, chewables, suppositories, pills, capsules, powders, liquids, or suspensions, and can be provided in unit dosages suitable for a single administration. Time release preparations are also contemplated as effective dosage formulations. The compositions can include an effective amount of a selected substrate in combination with a pharmaceutically acceptable carrier and, in addition, can include other medicinal agents, pharmaceutical agents, carriers, or diluents.

In a solid composition embodiment, conventional nontoxic solid carriers suitable for dietary supplement usage can include, for example, pharmaceutical grades of mannitol, lactose, starch, magnesium stearate, sodium saccharine, talc, cellulose, glucose, sucrose and magnesium carbonate. Liquid pharmaceutically administrable dietary supplements can, for example, be prepared by dissolving or dispersing an active compound with optimal pharmaceutical adjuvants in an excipient, such as water, saline, aqueous dextrose, glycerol, or ethanol, to form a solution or suspension. For example, the dietary supplement contain minor amounts of nontoxic auxiliary substances such as wetting or emulsifying agents, pH buffering agents, for example, sodium acetate or triethanolamine oleate. Actual methods of preparing such dietary supplement dosage forms are known, or will be apparent, to those skilled in this art.

In an oral administration embodiment, fine powders or granules can contain diluting, dispersing, or surface active agents. The fine powders or granules can be presented in water or in syrup, in capsules or sachets in the dry state, or in a nonaqueous solution or suspension. Suspending agents can also be included in tablets, which can include binders and lubricants in a suspension. Flavoring, preserving, suspending, thickening, or emulsifying agents can be also included to modify the taste and texture of the composition.

The tablets and granules provided for oral administration can further be coated for ease of digestion.

Functional Foods

The DHA- or EPA-containing phospholipid, micelle thereof, or other formulation containing the DHA- or EPA-containing phospholipid or micelle thereof described herein, can be consumed as part of a healthy diet for enriching a subject's Omega-3 fatty acid levels or as a dietary treatment in addition to the oral/parenteral administration of the compositions described herein as prescribed by a health professional. The DHA- or EPA-containing phospholipid, micelle thereof, or other formulation containing the DHA- or EPA-containing phospholipid or micelle thereof described herein can be incorporated into a food item and thus that food item can be referred to herein as a "functional food".

In certain embodiments, the functional food is in the form of edible or drinkable compositions, e.g., foodstuffs such as chewable or edible bars, confectionary products (e.g., chocolate bars), cookies, juice drinks, baked or simulated baked goods (e.g., brownies), biscuits, lozenges or chewing gum. Examples of chewable or edible bars include chocolate bars or energy bars. Such functional foods can be particularly useful to people participating in sports or other forms of exercise.

In certain embodiments, the functional foods can also be in the form of, for example, butter, margarine, bread, cake, milk shakes, ice cream, yogurt and other fermented milk product.

In certain embodiments, the functional food can also be in the form of a liquid to be sprayed on meats, salads or other foods.

Other forms of the functional foods can be breakfast cereals, such as for example, grain flakes, muesli, bran, oatmeal.

When the functional food product is in a drinkable form, the compositions described herein can be added directly to the drink, such as for example plain milk, flavored milk, fermented milk products or juices. The compositions will form micelles comprising the Omega-3 fatty acid esters in the drinkable product.

When the functional food is in the form of a solid edible product, the compositions described herein can be first added to an aqueous medium, wherein the composition will form micelles as described herein. The aqueous medium comprising the micelles can subsequently be either sprayed onto the solid edible product or mixed into the ingredients when manufacturing the edible product.

Methods of Using the DHA- or EPA-Containing Phospholipid Compounds, Micelles, and Formulations Thereof The DHA- or EPA-containing phospholipid, micelle thereof, or formulation thereof described herein can be administered to a subject. The subject can be a subject in need thereof. The subject in need thereof can have a disease or disorder that would benefit from increased DHA and/or EPA levels in one or more tissues or organs. The subject in need thereof can have a disease or disorder that can benefit from increased DHA and/or EPA levels in the brain. In some embodiments the subject in need thereof has or is suspected of having a neurological disease or disorder. The neurological disease or disorder can be depression, Alzheimer's disease, Parkinson's disease, or a traumatic brain injury.

In some embodiments, the amount of the DHA- or EPA-containing phospholipid, micelle thereof, or formulation thereof described herein delivered and/or administered to the subject in need thereof can be an amount sufficient to increase DHA and/or EPA levels in a tissue. The amount can be sufficient to increase DHA and/or EPA levels in the brain. The amount can be sufficient to treat a neurological disease or disorder in the subject. The neurological disease or disorder can be depression, Alzheimer's disease, Parkinson's disease, or a traumatic brain injury.

The DHA- or EPA-containing phospholipid, micelle thereof, or formulation thereof described herein can be co-administered or be a co-therapy with another active agent or ingredient that can be included in the formulation or provided in a dosage form separate from the DHA- or EPA-containing phospholipid, micelle thereof, or formulation thereof described herein.

The effective amount of the DHA- or EPA-containing phospholipid, micelle thereof, or formulation thereof described herein can range from about 0.1 µg/kg to up to about 100 mg/kg or more, depending on the factors mentioned elsewhere herein. In certain embodiments, the effective amount can range from 0.1 µg/kg up to about 100 mg/kg, or 1 µg/kg up to about 100 mg/kg, or 5 µg/kg up to about 100 mg/kg.

Administration of the DHA- or EPA-containing phospholipid, micelle thereof, or formulation thereof described herein can be systemic or localized. The DHA- or EPA-containing phospholipid, micelle thereof, or formulation thereof described herein can be administered to the subject in need thereof one or more times per day. In embodiments, the DHA- or EPA-containing phospholipid, micelle thereof, or formulation thereof described herein can be administered once daily. In other embodiments, the DHA- or EPA-containing phospholipid, micelle thereof, or formulation thereof described herein can be administered can be administered 2, 3, 4, 5, 6, 7, 8, 9, 10, 11, 12, or more times daily. In some embodiments, when administered, an effective amount of the DHA- or EPA-containing phospholipid, micelle thereof, or formulation thereof described herein can be administered to the subject in need thereof. The DHA- or EPA-containing phospholipid, micelle thereof, or formulation thereof described herein thereof can be administered one or more times per week. In some embodiments, DHA- or EPA-containing phospholipid, micelle thereof, or formulation thereof described herein can be administered 1, 2, 3, 4, 5, 6 or 7 days per week. In some embodiments, DHA- or EPA-containing phospholipid, micelle thereof, or formulation thereof described herein can be administered 1, 2, 3, 4, 5, 6, 7, 8, 9, 10, 11, 12, or more times per month. In some embodiments, DHA- or EPA-containing phospholipid, micelle thereof, or formulation thereof described herein can be administered 1, 2, 3, 4, 5, 6, 7, 8, 9, 10, 11, 12, 13, 14, 15, 16, 17, 18, or more time per year.

In some embodiments, the DHA- or EPA-containing phospholipid, micelle thereof, or formulation thereof described herein, can be administered in a dosage form. The amount or effective amount of the DHA- or EPA-containing phospholipid, micelle thereof, or formulation thereof described herein can be divided into multiple dosage forms. For example, the effective amount can be split into two dosage forms and the one dosage forms can be administered, for example, in the morning, and the second dosage form can be administered in the evening. Although the effective amount can be given over two or more doses, in one day, the subject can receives the effective amount when the total amount administered across all the doses is considered. The dosages can range from about 0.1 µg/kg to up to about 100 mg/kg or more, depending on the factors mentioned above. In certain embodiments, the dosage can range from 0.1

µg/kg up to about 100 mg/kg, or 1 µg/kg up to about 100 mg/kg, or 5 µg/kg up to about 100 mg/kg.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction.

Docosahexaenoic acid (DHA) is an omega 3 fatty acid that is highly concentrated in the brain, and is absolutely essential for the normal development and function of the brain [1,2]. However, it is not synthesized in significant amounts from its precursors in human brain, and has to be imported from plasma through the blood-brain barrier (BBB). Unlike other tissues, the uptake of DHA does not occur through the lipoprotein receptors in the brain [3,4]. There is some controversy regarding the molecular carrier of DHA to the brain. Previous studies in animals have reported that DHA in the form of lysophosphatidylcholine (LPC) passes through the BBB about 10 times more efficiently than as free fatty acid [5,6]. On the other hand, the recent kinetic studies [7] suggested that the free DHA in plasma is the major pool supplying the brain, although it was also reported that the brain uptake of injected LPC-DHA was higher than that of free DHA. The role of LPC is supported by the recent identification of a specific transporter (Mfsd2a) in the endothelial cells of BBB that selectively transports the LPC form of DHA [8]. Furthermore, the deficiency of this transporter results in defective brain development and impaired brain function in mice [8], as well as in humans [9], showing its physiological relevance. Thus it appears reasonable that the presence of DHA in plasma phospholipids would increase the brain DHA levels more than other molecular forms, and therefore the absorption of dietary DHA in the phospholipid form would be beneficial.

There are two major natural sources of dietary DHA, namely fish oil, in which it is present in the form of triacylglycerol (TAG), and krill oil, in which about 35% of DHA is in the phospholipid form (at the sn-2 position of PC) and the rest in TAG form. DHA-rich micro algal oil, which is used in some infant formulae also contains DHA in TAG form [10]. DHA from the sn-2 position of PC is released as free fatty acid (FFA) during digestion because of the specificity of pancreatic phospholipase $A_2$, whereas DHA from TAG is released by the action of gastric and pancreatic lipases, either as MAG or as free fatty acid depending upon the position occupied by DHA in TAG. Consequently, in both cases the DHA is absorbed as FFA (or as MAG) and is then re-esterified to TAG in the intestinal mucosa before being transported in the chylomicrons to various tissues (FIG. 1). These dietary forms of DHA are therefore less likely to enrich brain DHA, since the phospholipid form appears to cross the BBB (after conversion to lyso phospholipid) much more rapidly than other forms [5-8]. Previous studies showed that while the dietary DHA enriches most of the tissues, the brain levels are relatively unaffected by the amount of dietary DHA when fed as fish oil [11], ethyl ester concentrate [12], or algal oil [13]. It has also been reported that the liver can directly secrete LPC into the plasma [14], but the amount of LPC-DHA contributed by this pathway is unknown. Therefore absorption of DHA in the phospholipid form would be beneficial for its eventual uptake by the brain. We postulate that if the dietary DHA is present in the sn-1 position of PC, it would survive the hydrolysis by pancreatic $PLA_2$ during digestion, and would be absorbed as LPC and then converted to PC by the intestinal mucosal cells before entering the lymph (FIG. 1). The presence of DHA in plasma PC should increase its eventual uptake by the brain. Furthermore the PC generated in the intestine can be incorporated into HDL either directly by assembly in the mucosal cells [15] or due to a transfer of surface components from the chylomicrons during lipolysis by the lipoprotein lipase [16]. The PC from HDL can be hydrolyzed to LPC containing DHA either by the action(s) of endothelial lipase [17,18], hepatic lipase [19], or LCAT [20,21] and thus has a greater potential to cross the BBB. As a first step in testing these hypotheses we investigated the intestinal absorption of two molecular forms of DHA incorporated into micelle by rats with lymph duct cannulation. One type of micelle contained free DHA, representing the DHA released by the pancreatic enzymes from either DHA-TG or sn-2 DHA PC, while the second type of micelle contained LPC-DHA which would be the product of hydrolysis of sn-1 DHA PC by the pancreatic phospholipase $A_2$. The appearance of DHA in TAG and PC of chylomicrons and HDL of lymph was determined following the absorption of the two types of micelle in anesthetized rats. The results show that the incorporation of DHA into lymph PC can be increased about 5-fold, and its incorporation into HDL increased 2-fold by providing the DHA in LPC compared to free DHA.

Abbreviations for Example 1

BBB Blood brain barrier
CM Chylomicrons
FAME Fatty acid methyl esters
LPC Lysophosphatidylcholine
MAG Monoacylglycerol
MRM Multiple reaction monitoring
PC Phosphatidylcholine
TAG Triacylglycerol Materials and Methods.

Materials.

All free fatty acids (17:0, 18:1, 22:3, 22:6) as well as monoolein were purchased from Nu-Chek Prep Inc (Elysian, Minn.). Egg PC, 16:0 LPC, and 16:0-22:6 PC were obtained from Avanti Polar Lipids (Alabaster, Ala.). Taurocholate, and Mucor lipase (Lipozyme) were purchased from Sigma Chemical (St. Louis, Mo.). Solid phase extraction cartridges (Supelclean LC-$NH_2$, 1 ml) were obtained from Supelco (Bellefonte, Pa.).

LPC-DHA was prepared by the hydrolysis of 16:0-22:6 PC by immobilized Mucor lipase (Lipozyme) by a modification of the published procedure [22]. Briefly, 100 mg of Lipozyme was added to 50 mg of 16:0-22:6 PC dissolved in 1 ml of 95:5 (v/v) ethanol: water. The reaction mixture was incubated at 37° C. for 72 h under nitrogen with shaking. The reaction mixture was dried under nitrogen and extracted with 4 ml of ethanol: water: hexane (2:1:1, by vol) mixture to remove the free fatty acid. The lower layer was concentrated under nitrogen and extracted by Bligh and Dyer procedure [23]. The final sample contained 95% LPC, the rest being unhydrolyzed PC, as determined by lipid phosphorus estimation after TLC separation. Although this enzyme produces sn-2 22:6 LPC, this isomer is unstable, and is non-enzymatically isomerized to sn-1-22:6 LPC [24,25]. The isomer composition of LPC-DHA was not analyzed, but previous studies showed that at equilibrium, the ratio of sn-1 isomer to sn-2 isomer is about 9:1 [24,26].

Micelle Preparation.

Two types of micelle, one containing the DHA as free fatty acid, and the other containing the DHA as LPC, were prepared by sonication. The components of the micelle are listed in Table 1. All components except taurocholate were added as chloroform solutions to a glass tube and the solvent was evaporated under nitrogen. Then 10 ml of sodium taurocholate solution (12 mM, in PBS, pH 7.4) was added to the tube and the lipids dispersed by vortexing for 1 min. The mixture was then sonicated in a Sonics Vibro Cell sonicator at 40% setting for four 30 sec pulses at 1 min intervals, while the tube was immersed in ice. The resulting micelle were optically clear, and were used immediately for infusion into rats.

TABLE 1

Composition of the infused micelle.

| Compound | Micelle 1 (Free DHA) | Micelle 2 (LPC-DHA) |
|---|---|---|
| 2-Monoolein (mM) | 2.5 | 2.5 |
| Free Oleic acid (mM) | 5.1 | 7.5 |
| Free DHA (mM) | 2.4 | 0 |
| 16:0 LPC (mM) | 2.4 | 0 |
| 22:6 LPC (mM) | 0 | 2.4 |
| Egg PC (mM) | 0.6 | 0.6 |
| Sod. Taurocholate (mM) | 12 | 12 |

Lymph Duct Cannulation and Separation of Lipoproteins.

Male Sprague-Dawley rats (340-480 g) were obtained from Harlan Laboratories (Indianapolis, Ind.). All protocols were approved by the University of Illinois at Chicago animal care and use committee and were in compliance with the relevant guidelines of the National Research Council for the Care and Use of Laboratory Animals in Research.

Thoracic lymph duct cannulation was carried out as described [27] with slight modifications. The rats were fasted overnight before the procedure. Under analgesics and isoflurane anesthesia, the abdomen was opened, the dorsal parietal peritoneum was incised, and the aorta was dissected free from the surrounding muscle and thoracic duct. The duct was cannulated (3-5 mm) with a heparin (500 units/ml) and saline-rinsed, pre-cut catheter (16 gauge, BD Angio-cath). Following insertion, the catheter was connected to 'U" shaped secured Silastic Laboratory tubing to prevent displacement or dislodgement. Micelle (10 ml) were infused at a rate of 3 ml/h into the duodenum (Harvard pump) through a second catheter positioned into the duodenum, followed by the infusion of 10 ml PBS, at 3 ml/h. The abdomen was closed and the lymph was collected for 6 h, in 30 min fractions into tubes containing 1.0 ml of PBS, while the animal was under anesthesia. The body temperature of the animal was maintained at 37° C. with the help of a heating pad.

The volume of each lymph fraction was made up to 2.0 ml with PBS, containing 1 mM EDTA (final). The density of lymph fraction was raised to 1.063 g/ml by the addition of KBr and centrifuged at 100,000×g for 4 h at 4° C. in the TLA 100.3 rotor of the Beckman TL-100 ultracentrifuge. One ml of the bottom layer was aspirated to a new tube (HDL) and the remaining 1.0 ml was taken as the chylomicrons (CM).

Extraction and Analysis of Lipids. The total lipids of HDL and CM were extracted by the Bligh and Dyer method [23] after spiking the samples with 25 µg each of 15:0-15:0-15:0 TAG and 17:0-17:0 PC. The lipid extract was applied to an aminopropyl silica cartridge (100 mg) in 1 ml of chloroform under gravity, and the cartridge was washed with chloroform (2×1.0 ml) to elute the TAG and cholesteryl esters. Since we found in initial experiments very little DHA in the cholesteryl esters, we did not separate the TAG and cholesteryl esters before analysis. The PC was then eluted with 2.0 ml of chloroform: methanol (3:2, v/v)). The eluates were evaporated under $N_2$ and methylated by heating under nitrogen at 90° C. for 1 h with $BF_3$-methanol containing 25 µg 22:3 free fatty acid and 250 µg butylated hydroxytoluene. The fatty acid methyl esters (FAME) were extracted twice with 2 ml of hexane after adding 1.0 ml water, and the hexane extracts were evaporated under nitrogen, re-dissolved in 30 µl of hexane, and 1 µl was injected into GC/MS.

The analysis of FAME was carried out by GC/MS using Shimadzu QP2010SE, equipped with a Supelco Omegawax column (30 m×0.25 mm×0.25µ film thickness). The temperature program was as follows: 165° C. for 1 min, raised to 210° C. at the rate of 6.5° C./min, followed by raising to 240° C. at the rate of 3.5° C./min, and maintaining at 240° C. for 10 min. The total analysis time was 26.5 min. The injection temperature was 250° C., ion source temperature 230° C. and the interface temperature was 250° C. Total ion current in the range of 50-400 m/z was used to quantify the FAME, using 17:0 as the internal standard for the FAME derived from PC, and 15:0 for the FAME derived from TAG. The identification of individual FAME was done by comparison of retention times with the standard mixture (PUFA2, Sigma) as well as by the characteristic fragment ions (m/z 74 for saturated, m/z 55 for monounsaturated, m/z 67 for diunsaturated, and m/z 79 for polyunsaturated).

LC/MS Analysis of Molecular Species PC and TAG.

LC/MS analysis of molecular species of TAG and PC was performed on an ABSciex 6500 QTRAP mass spectrometer coupled with Agilent 2600 UPLC system. Mobile phase A consisted of chloroform/methanol/water, 80/19.5/0.5 (by vol) and mobile phase B consisted of chloroform/methanol/water 60/34.5/5.5 (by vol). Both A and B were supplemented with 0.1% of formic acid and 0.1% ammonium hydroxide. Each sample was dissolved in 100 µL of mobile phase A containing 50 ng each of 15:0-15:0-15:0 TAG and 17:0-17:0 PC as internal standards, and 10 µl was injected on to a normal phase silica column (Supelco Ascentis Si 3 µM, 100×2.1 mM). The lipids were separated by a gradient elution of solvent A and solvent B at the flow rate of 0.35 ml/min. The gradient program was: 0-5 min with 100% solvent A; 5-30 min with solvent A decreasing linearly from 100% to 0% and 30-35 min 100% B. The column temperature was maintained at 25° C. The spray voltage of the MS was 4.5 kV, and the source temperature was set at 450° C. Mass spectroscopy was performed in positive ionization mode for the quantification of PC species using multiple reaction monitoring (MRM) with transitions from molecular ion to the fragment of choline head group (m/z 184) (Tables 1-2).

TABLE 2

MRM values used for analysis of TAG and PC species that contain 22:6. The internal standards (IS) were used for the estimation of relative concentrations.

|  | Q1 (m/z) | Q3 (m/z) |
|---|---|---|
| TAG Species |  |  |
| TAG 15:0/15:0/15:0 (IS) | 782.7 | 523.5 |
| TAG 22:6/16:0/18:0 | 924.8 | 579.6 |
| TAG 22:6/16:0/18:1 | 922.7 | 577.5 |
| TAG 22:6/16:0/18:2 | 920.7 | 575.5 |
| TAG 22:6/18:0/18:0 | 952.8 | 607.6 |
| TAG 22:6/18:0/18:1 | 950.8 | 605.6 |
| TAG 22:6/18:1/18:1 | 948.8 | 603.6 |
| TAG 22:6/18:1/18:2 | 946.8 | 601.6 |
| TAG 22:6/18:2/18:2 | 944.8 | 599.6 |
| TAG 22:6/22:6/16:0 | 968.7 | 623.5 |
| TAG 22:6/22:6/18:0 | 996.8 | 651.6 |
| TAG 22:6/22:6/18:1 | 994.8 | 649.6 |
| TAG 22:6/22:6/18:2 | 992.7 | 647.5 |
| TAG 22:6/22:6/22:6 | 1040.8 | 695.6 |
| PC Species |  |  |
| PC 16:0-22:6 | 806.6 | 184.4 |
| PC 18:0-22:6 | 834.6 | 184.4 |
| PC 18:1-22:6 | 832.6 | 184.4 |
| PC 18:2-22:6 | 830.6 | 184.4 |
| PC 20:4-22:6 | 854.6 | 184.4 |
| PC 22:6-22:6 | 878.6 | 184.4 |
| PC 17:0-17:0 (IS) | 762.6 | 184.4 |

The TAG species containing DHA were quantified by positive MRM with transition from ammonia adducts of the molecular ions to their neutral loss fragments of ammoniated DHA. The identification of the molecular species was confirmed by the fatty acid products under negative ionization mode. However the positional distribution of fatty acids in TAG or PC was not determined. Quantitation of individual molecular species PC and TAG was performed from the relative intensities of the various species and the corresponding internal standards (17:0-17:0 PC and 15:0-15:0-15:0 TAG respectively). The data processing was performed with Analyst 1.6.2 (ABSciex, USA). The DHA content of individual TAG species was corrected for the number of DHA molecules present in each species.

Statistical Analysis.

The data are expressed as mean±SEM. Statistical significance of differences between the results of LPC-DHA and free DHA were determined by Student's t-test (unpaired) in Microsoft Excel program.

Results.

Comparison of Secretion of Free DHA and LPC-DHA into Lymph.

Figure 2:
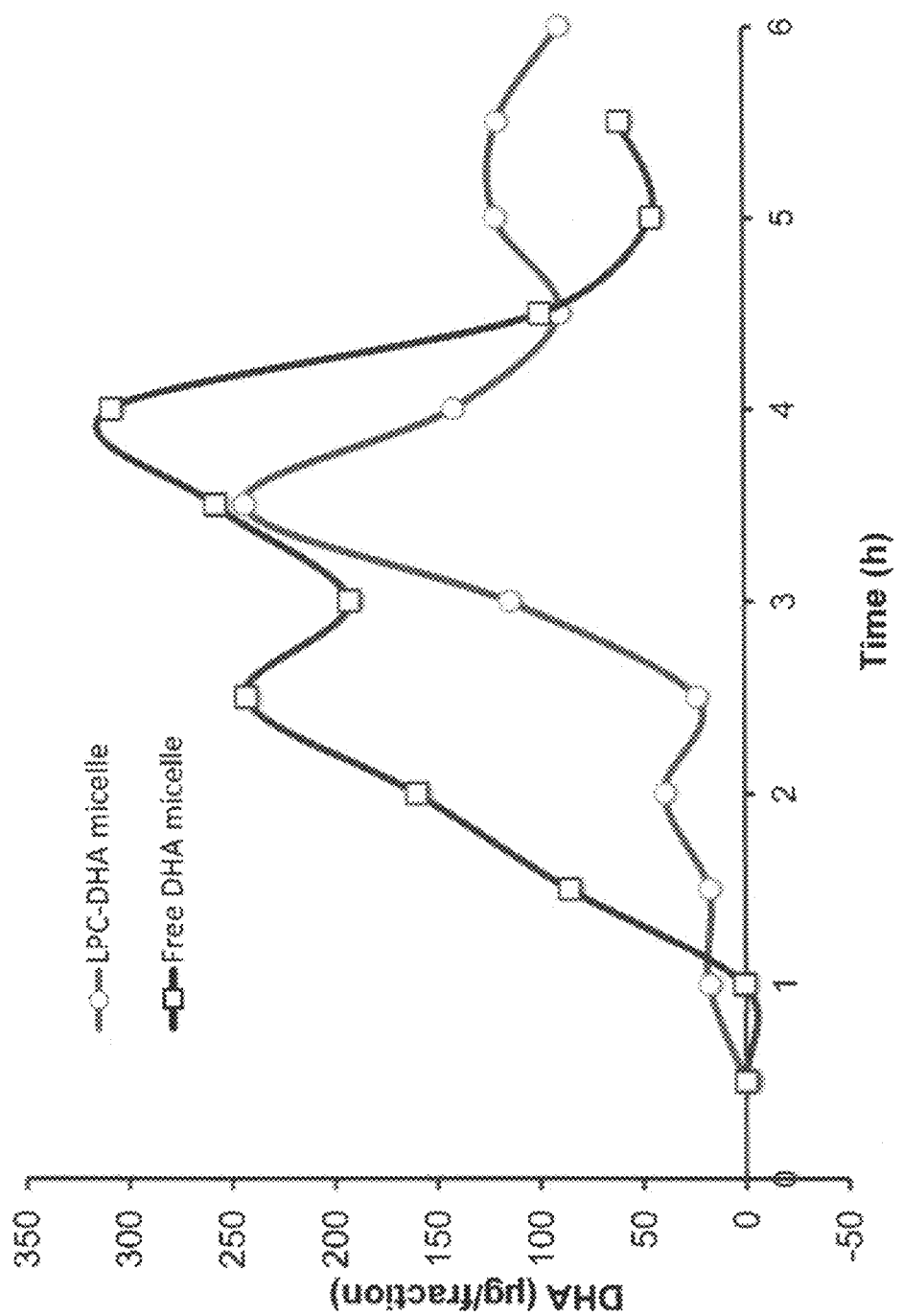
FIG. 2 shows a graph that can demonstrate the time course of absorption of DHA from the two types of DHA micelle. Micellar solutions in which DHA was present either as free fatty acid or as LPC were infused into the duodenum of rats and the lymph was collected in 30 min fractions for 6 h. The total amount of DHA in each fraction was determined by GC/MS as described in the text. Results from two representative experiments are shown. The flow rate of lymph varied from 0.5 ml to 1.0 ml/h. The peak of absorption was between 3 h and 4 h in all cases.
Figure 3:
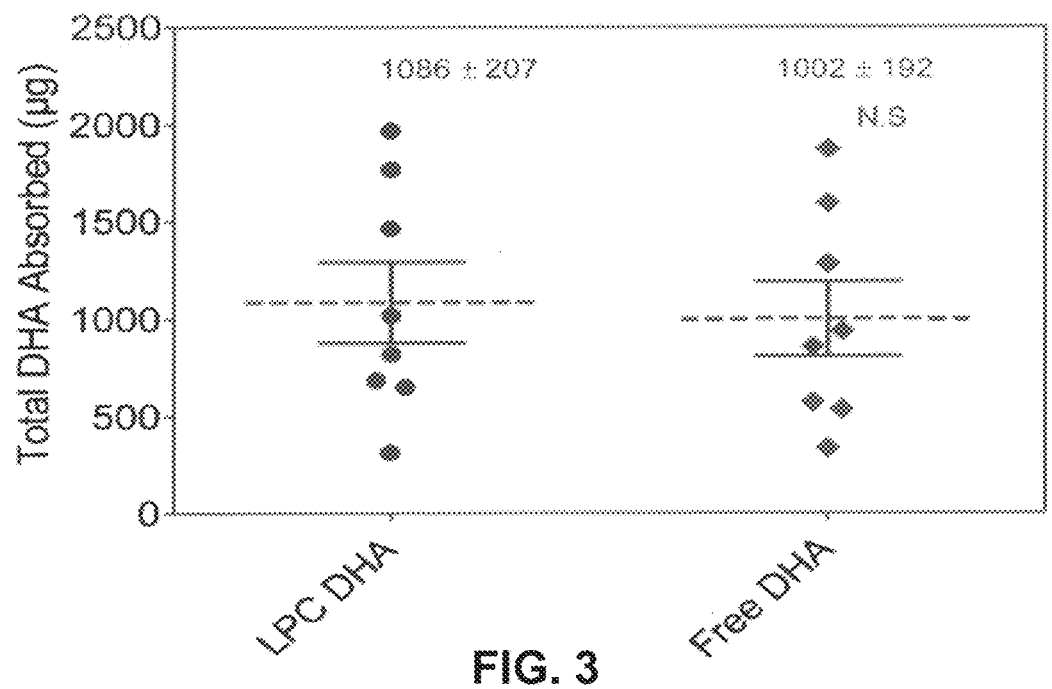
FIG. 3 shows a graph of the total DHA absorbed from free DHA micelle vs. LPC DHA micelle.
Figure 4:
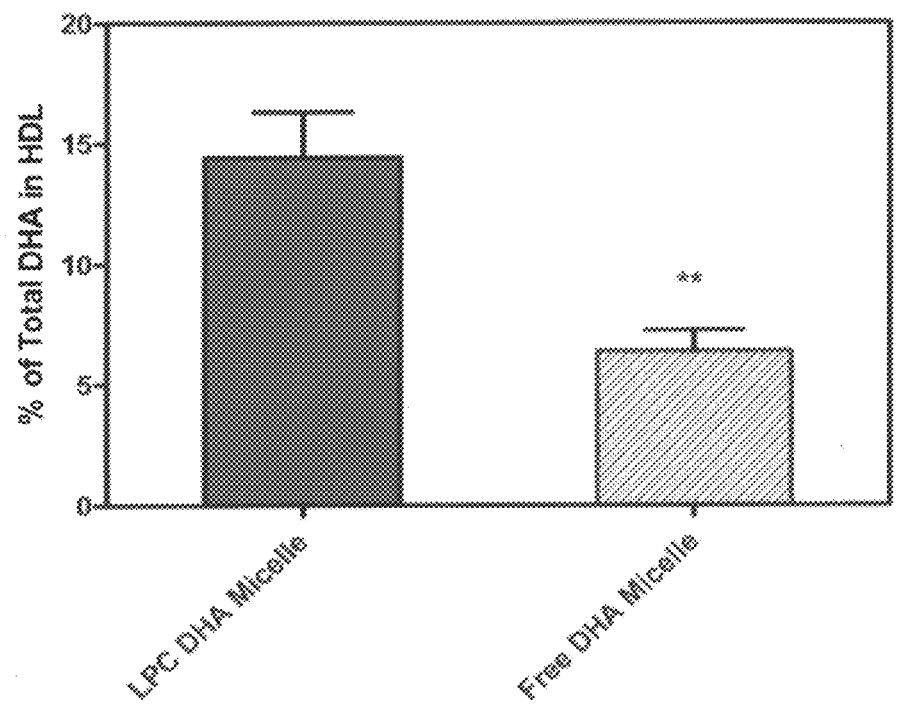
FIG. 4 shows a graph that can demonstrate the percent of total DHA recovered in HDL fraction of the lymph. HDL and CM from each lymph fraction were separated by centrifugation at a density of 1.063 g/ml, and their fatty acid composition was determined by GC/MS, as described in Section 2.4. The values shown are percentage of total DHA recovered in HDL from all the fractions, and are mean±SEM of 9 experiments for LPC-DHA and 7 experiments for free DHA. **p<0.01, free DHA vs LPC-DHA (unpaired t test).

The total amount of DHA in each fraction was determined by GC/MS as described in the text. Results from two representative experiments are shown. The flow rate of lymph varied from 0.5 ml to 1.0 ml/h. The peak of absorption was between 3 h and 4 h in all cases. The flow rates of lymph varied from 0.5-1.0 ml/h in individual rats, and the peak of DHA absorption was 3-4 h in both groups. FIG. 2 shows a graph that can demonstrate the time course of absorption of DHA from the two types of DHA micelle. Micellar solutions in which DHA was present either as free fatty acid or as LPC were infused into the duodenum of rats and the lymph was collected in 30 min fractions for 6 h. Except for the molecular form of DHA, the concentrations of various micellar components (monoacylglycerol, free fatty acid, LPC, PC, bile salt) were exactly the same in the two micellar preparations (Table 1). The free DHA micelle represent the products generated in the intestinal lumen during the digestion of sn-2 DHA PC (or DHA-TAG), whereas the LPC-DHA micelle represent the products generated during the digestion of sn-1 DHA PC, since the pancreatic phospholipase A is specific for the sn-2 ester linkage. The total amount of DHA appearing in the lymph over the 6 h period did not differ significantly between the two types of micelle, although there were wide variations among individual animals (FIGS. 3-4). In some experiments with LPC-DHA, we analyzed the intestinal contents after the 6 h lymph collection, and found only LPC-DHA without substantial amount of free DHA, indicating no hydrolysis of LPC in the lumen.

Incorporation of DHA into HDL and Chylomicron (CM) Fractions.

The individual lymph fractions were fractionated into HDL and CM subfractions by centrifugation at 1.063 g/ml, the total lipids were extracted, and the amount of DHA recovered in the two fractions was determined by GC/MS.

Incorporation of DHA into PC and TAG.

Figure 5:
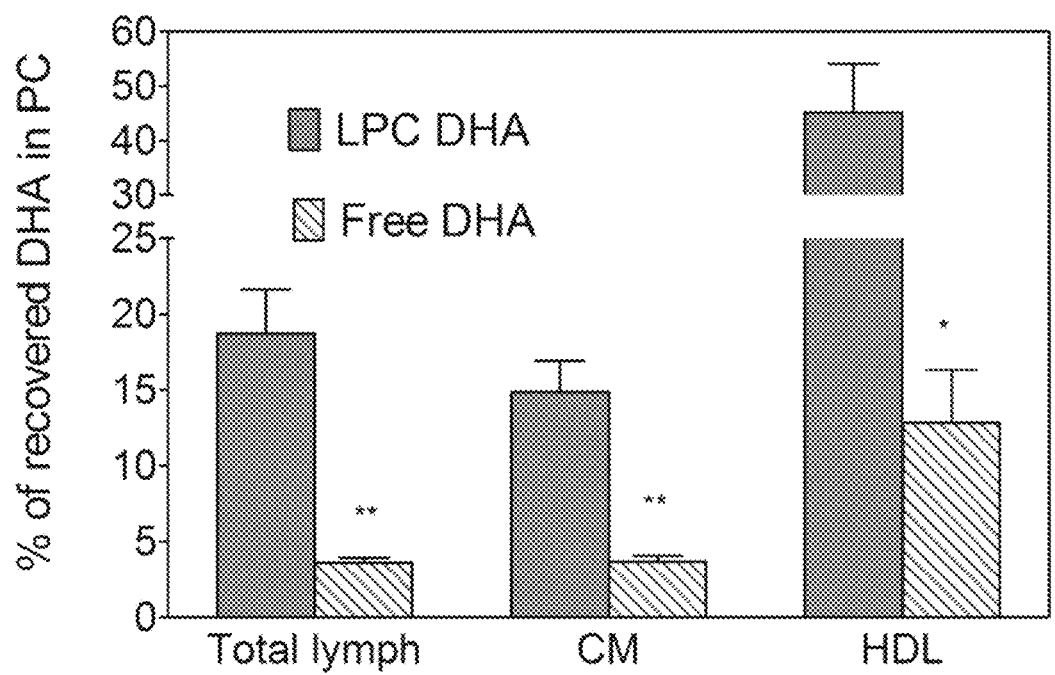
FIG. 5 shows a graph that can demonstrate the percent of absorbed DHA recovered in PC. The PC and TAG from the lipids of total lymph, HDL, and CM were separated on aminopropyl columns, and the fatty acid composition was determined by GC/MS. The percent of DHA recovered in PC was calculated from this data. The PC fraction contained a small amount of DHA as PE (<10%), since these two lipids were not separated in this procedure. All the remaining DHA was in TAG. The results shown are mean±SEM. (n=10 total lymph for LPC-DHA, n=8 for total lymph for free DHA, n=5 each HDL and CM for both micelle). * P<0.05; ** p<0.005 free DHA vs LPC-DHA (unpaired t test).

FIG. 5 shows the percent of total DHA recovered in the phospholipids of whole lymph, and the HDL and chylomicron subfractions. The rest of the DHA was present in the neutral lipids (TAG and cholesteryl esters). The LC/MS analyses showed that small amounts of DHA were incorporated into PE with both the micelle preparations (<10% of DHA in PC), but this was included in the PC in the present studies because PC and PE were not well separated under the conditions used. A significant amount of free DHA was not observed in the lymph after infusion of either free DHA or LPC-DHA. The percent of whole lymph DHA appearing in PC was 5 times higher when micellar DHA was present as LPC (18.72±2.88, mean±SEM), compared to its presence as free fatty acid (3.66±0.32, mean±SEM). The difference between the two micellar forms is more pronounced in HDL compared to chylomicrons. Thus in HDL, about 45% of DHA was present in PC after the absorption of LPC-DHA micelle, compared to only about 13% with free DHA micelle. In the chylomicrons, the majority of DHA was recovered in TAG with both preparations of DHA, although the percent recovered as PC was still higher with LPC-DHA micelle (14.8%) compared to free DHA micelle (3.7%). These results thus show that providing the dietary DHA in the form of LPC results in its increased incorporation into phospholipids of lymph, especially in the HDL fraction. However, the majority of LPC absorbed appears to be hydrolyzed inside the mucosal cells and the resulting free DHA incorporated predominantly into TAG.

Molecular Species of TAG Formed from the Two Types of Micellar DHA.

Figure 6:
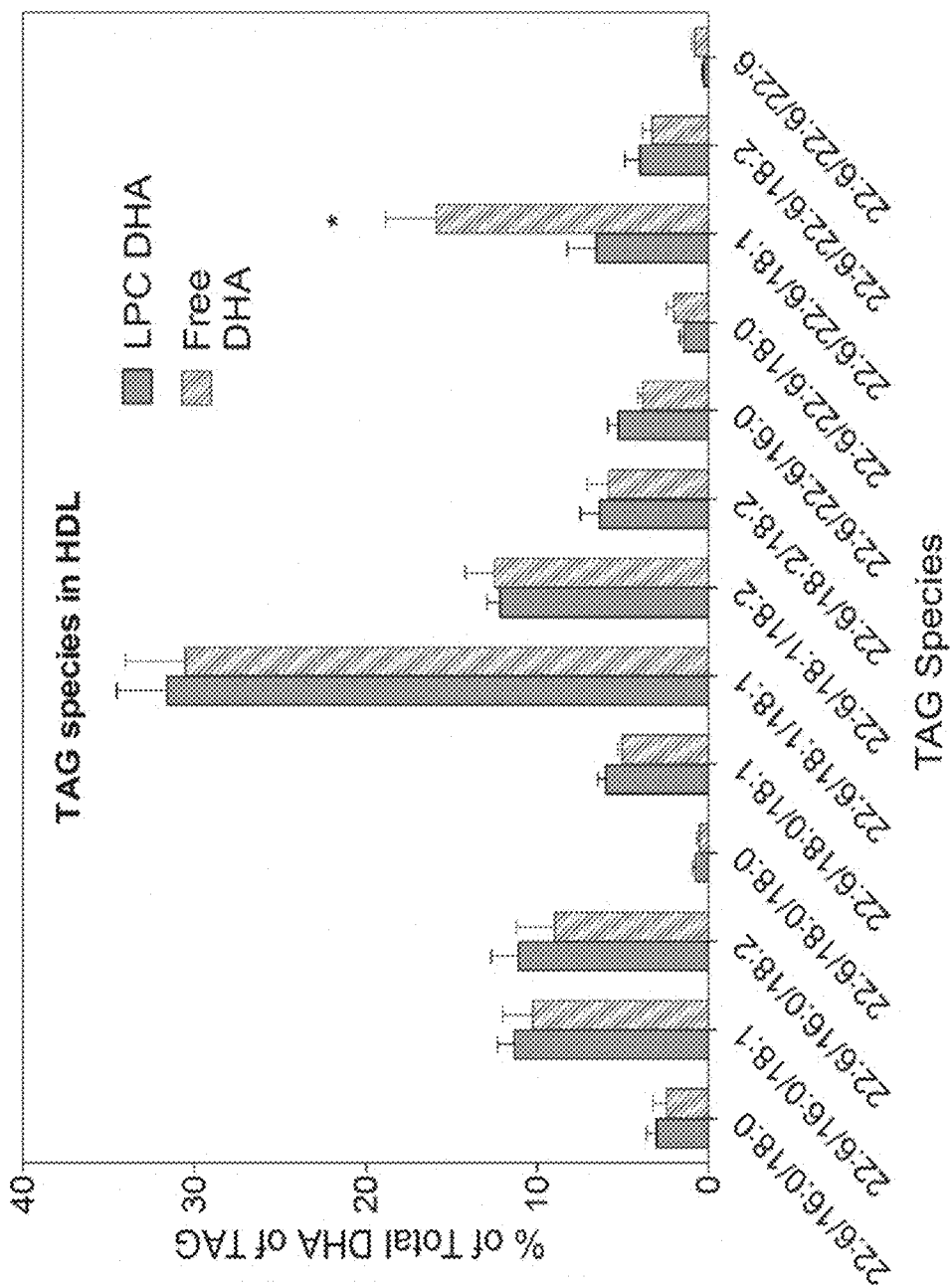
FIG. 6 shows a graph that can demonstrate the molecular species of TAG containing DHA in HDL. The molecular species composition of DHA-containing TAG species was determined by MRM in LC/MS as described in the text (and supplementary data, Table 1). The nomenclature of the species is based on the fatty acid composition, but the position of the fatty acids on the glycerol backbone has not been determined. The values shown are mean±SEM of 9 experiments for LPC-DHA and 7 experiments for free DHA. *p<05, free DHA vs LPC-DHA (unpaired t test).
Figure 7:
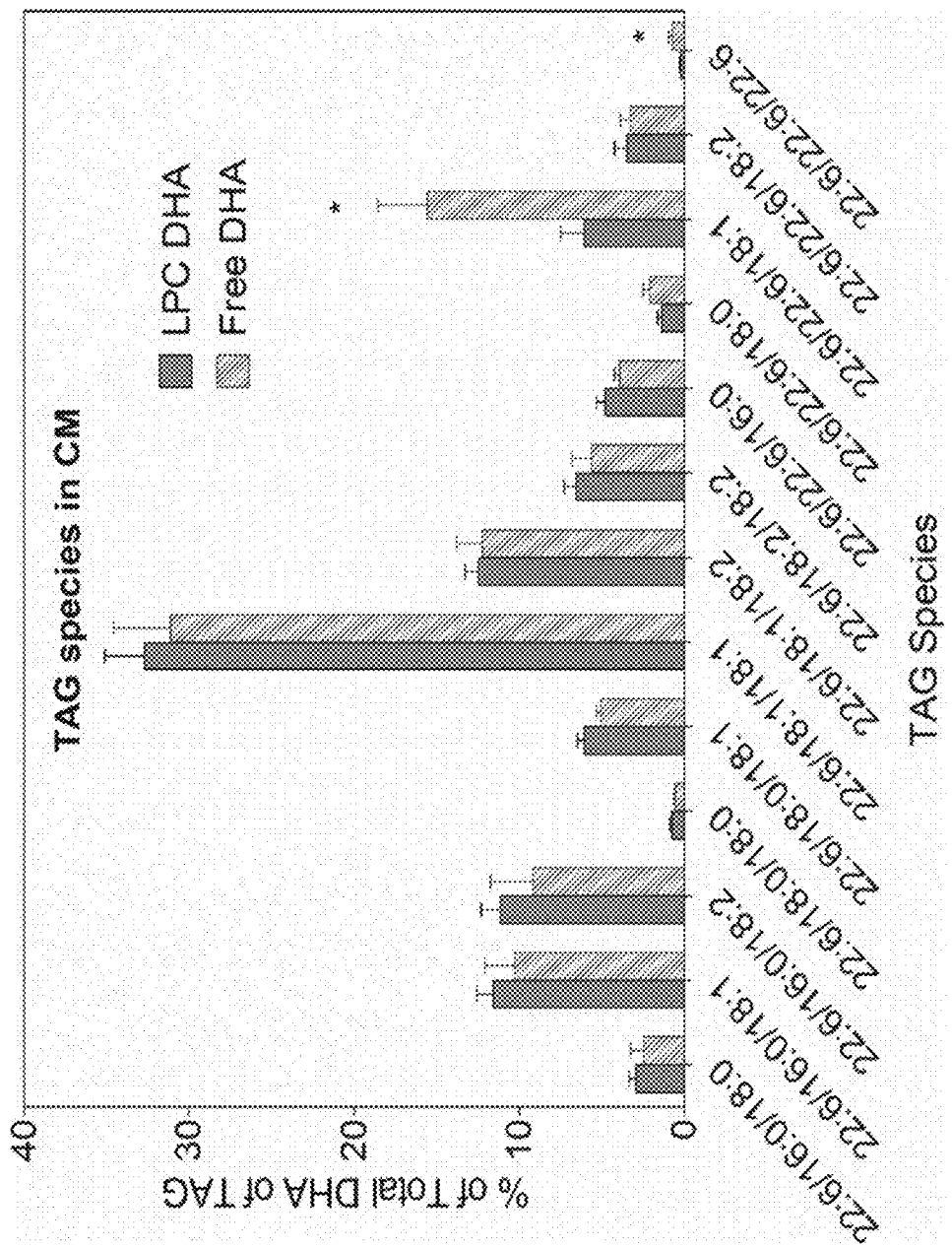
FIG. 7 shows a graph that can demonstrate the molecular species of TAG containing DHA in lymph CM. The molecular species composition was determined by MRM in LC/MS as described in Example 1 (e.g. Tables 1-2). The values shown are mean±SEM of 9 experiments for LPC-DHA and 7 experiments for free DHA. *p<0.05, free DHA vs LPC-DHA (unpaired t test).

The molecular species of TAG containing DHA were analyzed by LC/MS/MS to determine whether the DHA derived from the two micellar forms of DHA is metabolized differently in the mucosal cells. As shown in FIGS. 6-7, 13 molecular species of TAG that contained DHA were identified by LC/MS in the HDL and chylomicron subfractions of the lymph. The results shown are the percentages of TAG-DHA in individual TAG species (taking into account the number of DHA molecules per molecule of TAG). Since 2-monoolein was present as the backbone in both types of micelle, it is not surprising that the predominant DHA-containing TAGs in both HDL and CM also contained 18:1. The most abundant DHA-TAG species was 22:6/18:1/18:1 in HDL as well as in CM with both types of the micelle. Statistically, the percentage of 22:6/22:6/18:1 species was significantly higher after the absorption of free DHA, compared to LPC-DHA in both HDL and CM (FIGS. 6-7). This suggests the esterification of monoolein with two molecules of free DHA when excess free DHA is available inside the mucosal cell. In addition, the TAG species containing DHA at all 3 positions was also significantly higher after free DHA absorption, compared to LPC-DHA absorption, reflecting the presence of higher concentration of free DHA inside the cells.

Molecular Species of PC Formed from the Two Types of Micellar DHA.

The most abundant DHA-PC was 16:0/22:6, followed by 18:0/22:6 and 18:1/22:6 in both HDL and chylomicron fractions of the lymph after absorption of either type of micelle (FIGS. 8-9). The percentage of 16:0/22:6 PC was significantly lower following the absorption of LPC-DHA, compared to free DHA absorption, in both HDL and CM. All other species containing 22:6 were increased significantly at the expense of 16:0/22:6, especially in HDL (FIG. 8). In CM, only the increase in 20:4/22:6 PC was statistically significant, although most DHA-PC species showed an increase following LPC-DHA absorption compared to free DHA absorption.

Discussion

Evidence from both biochemical [5,6] and genetic [8,9] studies supports the role of LPC-DHA as a preferred carrier of DHA through the BBB. Although the recent kinetic studies by Chen et al [7] challenged this paradigm, these studies also showed that the uptake of a bolus injected LPC-DHA is greater than that of injected free DHA. Therefore the presence of DHA in plasma phospholipids appears to be beneficial for its brain accrual. The main goal of the present study is to determine whether the amount of dietary DHA absorbed and secreted as phospholipid into the lymph lipoproteins can be increased by feeding sn-1 DHA PC, instead of the naturally occurring sn-2 DHA PC (as present in krill oil) or DHA-TAG (as present in fish oil and krill oil). We used the absorption of LPC-DHA from micelle as substitute for the digestion and absorption of sn-1 DHA PC, and the absorption of free DHA from micelle as substitute for the digestion and absorption of sn-2 DHA PC, based on the expected products of hydrolysis of the two isomers of PC by the pancreatic phospholipase $A_2$. The free DHA also serves as a substitute for the free DHA released from DHA-TAG digestion by the pancreatic lipase. Both the micelle also contained 2-monoolein and free oleic acid to represent the hydrolytic products of dietary TAG. The results presented here show that while the total amount of DHA delivered into lymph is comparable for the two types of DHA micelle, the percentage of DHA incorporated into lymph phospholipids is about 5-fold higher after the absorption of LPC-DHA. Furthermore, the DHA recovered in HDL fraction of the lymph was increased by at least 2-fold. Even though the absorption studies were performed in anesthetized rats in which the rate of absorption can be lower than in the conscious animals, the relative distribution of DHA between TAG and PC in lymph would be expected to be the same as in the conscious animals. While we have not determined the position occupied by DHA in the lymph PC, LPC-DHA could be generated from either sn-1 DHA PC or sn-2 DHA PC in the plasma compartment. Thus, the various $PLA_1$ activities like those of endothelial lipase [17,18], hepatic lipase [19], or LCAT [20,21] could generate LPC-DHA from sn-2 DHA PC, whereas the secretory phospholipases $A_{2\ [28,29]}$ could generate LPC-DHA from sn-1 DHA PC. The relative importance of various phospholipase activities of plasma in the generation of LPC-DHA in plasma is not yet known.

Several factors could account for the observation that the majority of DHA is incorporated into CM TAG rather than PC, even when the DHA was provided as LPC-DHA. First and foremost, the amount of phospholipid that can be incorporated into CM is limited, since the CM particle contains only a monolayer of phospholipid which constitutes about 4% of the total lipid, and of this only about 80% is PC [30]. In addition, the dietary PC is diluted with significant amount of biliary PC, which gives rise to saturated LPC during digestion, and thus competes with LPC-DHA for the reacylation and incorporation into CM in the mucosal cell. This further reduces the maximum amount of dietary phospholipid that can be incorporated into CM PC. Scow et al [31] reported that at least 60% of PC in the CM is derived from endogenous sources even after feeding large excess of PC in the diet. Therefore, when LPC-DHA is absorbed, only a fraction of this LPC can be expected to be acylated to PC and incorporated into CM. The remaining LPC-DHA is hydrolyzed by the mucosal lysophospholipase and the resulting free DHA is incorporated into TAG. The extensive degradation of the absorbed LPC has also been reported for 16:0 LPC [31,32], which is naturally formed from the hydrolysis of biliary PC in the intestinal lumen. The percentage of DHA recovered in lymph PC after LPC-DHA infusion in our studies (18%) is lower than the recovery of 16:0 after infusion of 16:0 LPC (25-30%) [32], possibly due to the substrate specificity of the mucosal LPC acyltransferase. Although the specificity of this enzyme towards the polyunsaturated LPCs has not been reported, it is likely that it prefers the more abundant 16:0 LPC which is released from the hydrolysis of biliary PC, based on the results with the human LPCAT3 expressed in yeast [33]. It is also possible that the LPC-DHA employed here contained significant amount of sn-2 DHA isomer, although previous studies showed that at equilibrium, 90% of LPC is sn-1 isomer [24,34]. The sn-2 isomer can be preferentially hydrolyzed in the lumen or mucosal cells, releasing free DHA. Further studies are needed to determine the relative incorporation rates sn-1 and sn-2 isomers of LPC-DHA into lymph phospholipids.

In contrast to CM, the HDL particles secreted by the intestine contain relatively more PC and less TAG per particle. A small but significant amount of absorbed LPC-DHA can be diverted to HDL PC synthesis, thus increasing the amount of DHA secreted via HDL into lymph. In fact previous studies in humans showed that the newly absorbed PC is preferably associated with HDL [35]. We found that there is a >2-fold increase in amount of DHA recovered in lymph HDL after LPC-DHA absorption, compared to free DHA absorption, and about of half of the DHA in lymph HDL was associated with PC. It has been reported that the intestinal HDL is also directly secreted into the plasma, rather than into the lymph [36], in which case the actual amount of DHA incorporated into HDL phospholipids can be much higher than reported here, because we only analyzed the HDL in the lymph. HDL PC is the preferred substrate for all enzymes displaying phospholipase activity in the plasma [18-20,28,29], and therefore the presence of DHA PC in HDL would be beneficial for the generation of LPC-DHA in the plasma compartment and for its potential uptake by the brain through the Mfsd2a [8] pathway. The amount of HDL secreted by the intestine can be increased significantly by LXR agonists which stimulate the transcription of ABCA1 [37]. It would be therefore of interest to study whether the incorporation of DHA into HDL PC can be increased by pretreatment of the animals with an LXR agonist. It is also necessary to perform long term feeding studies with sn-1 DHA PC or DHA LPC to determine whether they will enrich brain DHA more efficiently than either DHA TAG or sn-2 DHA PC commonly employed at present.

SUMMARY

This Example can show that the delivery of DHA in into lymph phospholipids can be increased by 5-fold, and its incorporation into HDL increased by 2-fold, if the DHA is present in the sn-1 position of dietary phospholipids or in LPC, compared to its presence in the sn-2 position of PC or in TAG. The increased concentration of DHA in the plasma phospholipids can be beneficial for its transport into the brain through the Mfsd2a transporter pathway [8].

REFERENCES FOR EXAMPLE 1

1. Alessandri J M, Guesnet P, Vancassel S FAU—Astorg P, Astorg P F, Denis I F, Langelier B F, Aid S FAU—Poumes-Ballihaut C, Poumes-Ballihaut C F, Champeil-Potokar G F, Lavialle M. Polyunsaturated fatty acids in the central nervous system: evolution of concepts and nutritional implications throughout life. Reprod. Nutr Dev. 2004; 44:509-538.
2. Lukiw W J, Bazan N G. Docosahexaenoic acid and the aging brain. J. Nutr. 2008; 138:2510-2514.
3. Chen C T, M A DWL, Kim J H, Mount H T J, Bazinet R P. The low density lipoprotein receptor is not necessary for maintaining mouse brain polyunsaturated fatty acid concentrations. J. Lipid Res. 2008; 49:147-152.
4. Rahman T, Taha A Y, Jun Song B, Orr S K, Liu Z, Chen C T, Bazinet R P. The very low density lipoprotein receptor is not necessary for maintaining brain polyunsaturated fatty acid concentrations. Prostaglandins, Leukotrienes and Essential Fatty Acids. 2010; 82:141-145.
5. Thies F, Pillon C, Moliere P, Lagarde M, Lecerf J. Preferential incorporation of sn-2 lysoPC DHA over unesterified DHA in the young rat brain. Amer. J. Physiol-Regul. Integr. C. 1994; 36:R1273-R1279.
6. Lagarde M, Bernoud N, Brossard N, Lemaitre-Delaunay D, Thies F, Croset M, Lecerf J. Lysophosphatidylcholine as a preferred carrier form of docosahexaenoic acid to the brain. J. Mol. Neurosci. 2001; 16:201-204.
7. Chen C T, Kitson A P, Hopperton K E, Domenichiello A F, Trépanier M O, Lin L E, Ermini L, Post M, Thies F, Bazinet R P. Plasma non-esterified docosahexaenoic acid is the major pool supplying the brain. Sci Rep. 2015; 5:15791.
8. Nguyen L N, Ma D, Shui G, Wong P, Cazenave-Gassiot A, Zhang X, Wenk M R, Goh E L K, Silver D L. Mfsd2a is a transporter for the essential omega-3 fatty acid docosahexaenoic acid. Nature. 2014; 509:503-506.
9. Guemez-Gamboa A, Nguyen L N, Yang H, Zaki M S, Kara M, Ben-Omran T, Akizu N, Rosti R O, Rosti B, Scott E, Schroth J, Copeland B, Vaux K K, Cazenave-Gassiot A, Quek D Q Y, Wong B H, Tan B C, Wenk M R, Gunel M, Gabriel S, Chi N C, Silver D L, Gleeson J G. Inactivating mutations in MFSD2A, required for omega-3 fatty acid transport in brain, cause a lethal microcephaly syndrome. Nat Genet. 2015; 47:809-813.
10. Arterburn L M, Boswell K D, Lawlor T, Cifone M A, Murli H, Kyle D J. In vitro genotoxicity testing of ARASCO-® and DHASCO-® oils. Food Chem. Toxicol. 2000; 38:971-976.
11. Martins S V, Lopes P A, Ramos C, Miguueis S, Alfaia C M, Pinto R M A, Rolo E A, Bispo P, Batista I, Bandarra N M, Prates J A M. Influence of feeding graded levels of canned sardines on the inflammatory markers and tissue fatty acid composition of Wistar rats. British Journal of Nutrition. 2014; 112:309-319.
12. Saito M, Ueno M, Kubo K, Yamaguchi M. Dose-Response Effect of Dietary Docosahexaenoic Acid on Fatty Acid Profiles of Serum and Tissue Lipids in Rats. J. Agr. Food Chem. 1998; 46:184-193.
13. Lin Y H, Shah S, Salem N. Altered essential fatty acid metabolism and composition in rat liver, plasma, heart and brain after microalgal DHA addition to the diet. J. Nutr. Biochem. 2011; 22:758-765.
14. Sekas G, Patton G M, Lincoln E C, Robins S J. Origin of plasma lysophosphatidylcholine: evidence for direct hepatic secretion in the rat. J Lab Clin Med. 1985; 105:190-194.
15. Wang H, Du J, Lu S, Yao Y, Hunter F, Black D D. Regulation of intestinal apolipoprotein A-I synthesis by dietary phosphatidylcholine in newborn swine. Lipids. 2001; 36:683-687.
16. Tall A R, Green P H R, Glickman R M, Riley J W. Metabolic Fate of Chylomicron Phospholipids and Apoproteins in the Rat. J. Clin. Invest. 1979; 64:977-989.
17. Chen S, Subbaiah P V. Phospholipid and fatty acid specificity of endothelial lipase: Potential role of the enzyme in the delivery of docosahexaenoic acid (DHA) to tissues. Biochim. Biophys. Acta. 2007; 1771:1319-1328.
18. Yang P, Belikova N A, Billheimer J, Rader D J, Hill J S, Subbaiah P V. Inhibition of endothelial lipase activity by sphingomyelin in the lipoproteins. Lipids. 2014; 49:987-996.
19. Yang P, Subbaiah P V. Regulation of hepatic lipase activity by sphingomyelin in plasma lipoproteins. Biochim Biophys Acta. 2015; 1851:1327-1336.
20. Subbaiah P V, Liu M, Paltauf F. Role of sn-2 acyl group of phosphatidyl choline in determining the positional specificity of lecithin-cholesterol acyltransfersae. Biochemistry. 1994; 33:13259-13266.
21. Subbaiah P V, Sowa J M, Davidson M H. Evidence for altered positional specificity of LCAT in vivo: studies with docosahexaenoic acid feeding in humans. J. Lipid Res. 2004; 45:2245-2251.
22. Sarney D, Fregapane G, Vulfson E. Lipase-catalyzed synthesis of lysophospholipids in a continuous bioreactor. J Am Oil Chem Soc. 1994; 71:93-96.
23. Bligh E G, Dyer W J. A rapid method of total lipid extraction and purification. Can. J. Biochem. Physiol. 1959; 37:911-917.
24. Plueckthun A, Dennis E A. Acyl and phosphoryl migration in lysophospholipids: importance in phospholipid synthesis and phospholipase specificity. Biochemistry. 1982; 21:1743-1750.
25. Croset M, Brossard N, Polette A, Lagarde M. Characterization of plasma unsaturated lysophosphatidylcholines in human and rat. Biochem. J. 2000; 345:61-67.
26. Chen J, Tang H, Sysol J R, Moreno-Vinasco L, Shioura K M, Chen T, Gorshkova I, Wang L, Huang L S, Usatyuk P V, Sammani S, Zhou G, Raj J U, Garcia J G, Berdyshev E, Yuan J X, Natarajan V, Machado R F. The sphingosine kinase 1/sphingosine-1-phosphate pathway in pulmonary arterial hypertension. Am J Respir Crit Care Med. 2014; 190:1032-1043.
27. Milling S W, Jenkins C, MacPherson G. Collection of lymph-borne dendritic cells in the rat. Nat. Protoc. 2006; 1:2263-2270.

28. Singh D K, Subbaiah P V. Modulation of the activity and arachidonic acid selectivity of group X secretory phospholipase $A_2$ by sphingolipids. J. Lipid Res. 2007; 48:683-692.
29. Singh D K, Gesquiere L R, Subbaiah P V. Role of sphingomyelin and ceramide in the regulation of the activity and fatty acid specificity of group V secretory phospholipase $A_2$. Arch. Biochem. Biophys. 2007; 459: 280-287.
30. Zilversmit D B. The surface coat of chylomicrons: lipid chemistry. J. Lipid Res. 1968; 9:180-186.
31. Scow R O, Stein Y, Stein O. Incorporation of Dietary Lecithin and Lysolecithin into Lymph Chylomicrons in the Rat. J. Biol. Chem. 1967; 242:4919-4924.
32. Nilsson A. Intestinal absorption of lecithin and lysolecithin by lymph fistula rats. Biochim Biophys Acta. 1968; 152:379-390.
33. Kazachkov M, Chen Q, Wang L, Zou J. Substrate preferences of a lysophosphatidylcholine acyltransferase highlight its role in phospholipid remodeling. 2008; 43:895-902.
34. Kielbowicz G, Smuga D, Gladkowski W, Chojnacka A, Wawrzenczyk C. An LC method for the analysis of phosphatidylcholine hydrolysis products and its application to the monitoring of the acyl migration process. Talanta. 2012; 94:22-29.
35. Zierenberg O, Grundy S M. Intestinal absorption of polyenephosphatidylcholine in man. J. Lipid Res. 1982; 23:1136-1142.
36. Brunham L R, Kruit J K, Iqbal J, Fievet C, Timmins J M, Pape T D, Coburn B A, Bissada N, Staels B, Groen A K, Hussain M M, Parks J S, Kuipers F, Hayden M R. Intestinal ABCA1 directly contributes to HDL biogenesis in vivo. J. Clin. Invest. 2006; 116:1052-1062.
37. Sato M, Kawata Y, Erami K, Ikeda I, Imaizumi K. LXR Agonist Increases the Lymph HDL Transport in Rats by Promoting Reciprocally Intestinal ABCA1 and apo A-I mRNA Levels, Lipids. 2008; 43:125-131.

Example 2

Introduction

Figure 10:
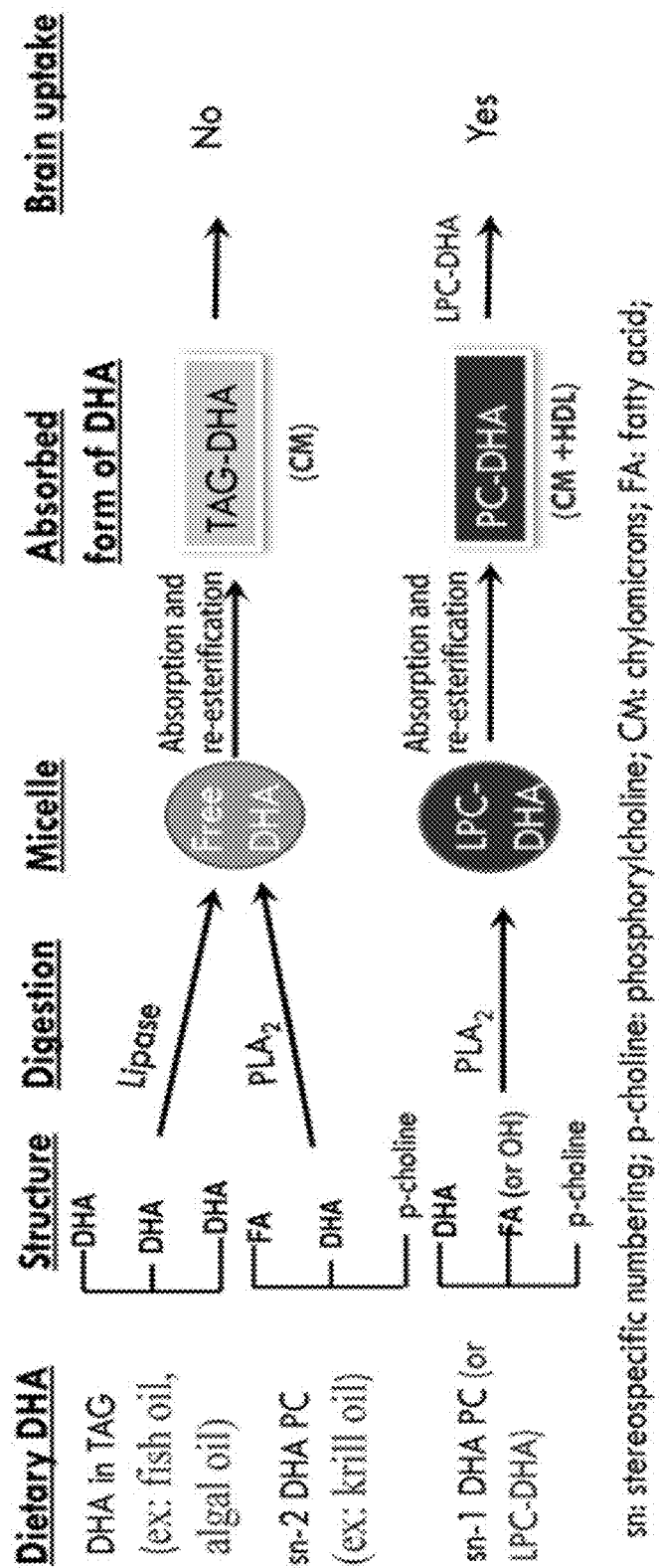
FIG. 10 shows a schematic that can show that when dietary DHA is present in TAG (ex: fish oil) or in sn-2 position of PC (ex: krill oil), it is released as free fatty acid and absorbed as TAG in the chylomicrons. On the other hand, if DHA is provided in sn-1 position of PC, or as LPC, it will be absorbed as PC in chylomicrons and HDL. The PC-DHA is more likely to be transported into brain after direct conversion to LPC, compared to TAG-DHA, since the brain preferentially takes up DHA as LPC.
Figure 11A:
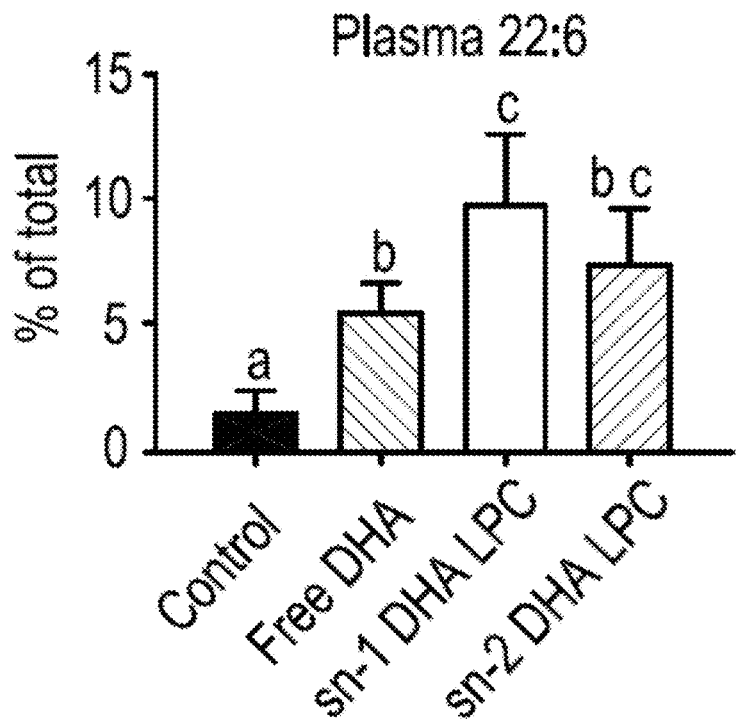
FIGS. 11A-11D show graphs that can demonstrate the effect of molecular carrier of dietary DHA on plasma levels (% of total fatty acid) of 22:6 (FIG. 11A), and 20:4 (FIG. 11B), 22:6/20:4 ratio (FIG. 11C), and on LPC-DHA (µg/ml) (FIG. 11D). Results shown are mean±SD (n=8). Bars in each panel not sharing a common superscript are significantly different from each other (p<0.05, one way ANOVA, and post-hoc Tukey test).
Figure 11B:
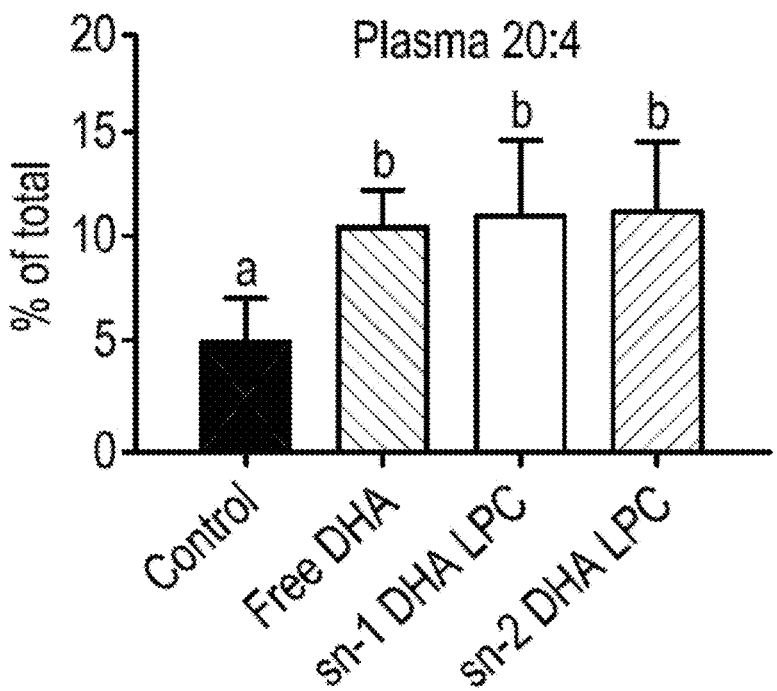
Figure 11C:
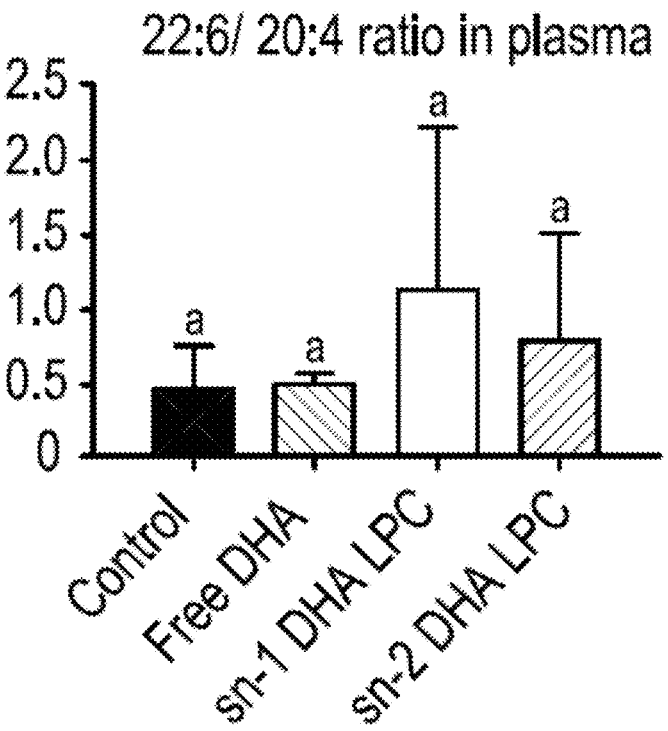
Figure 11D:
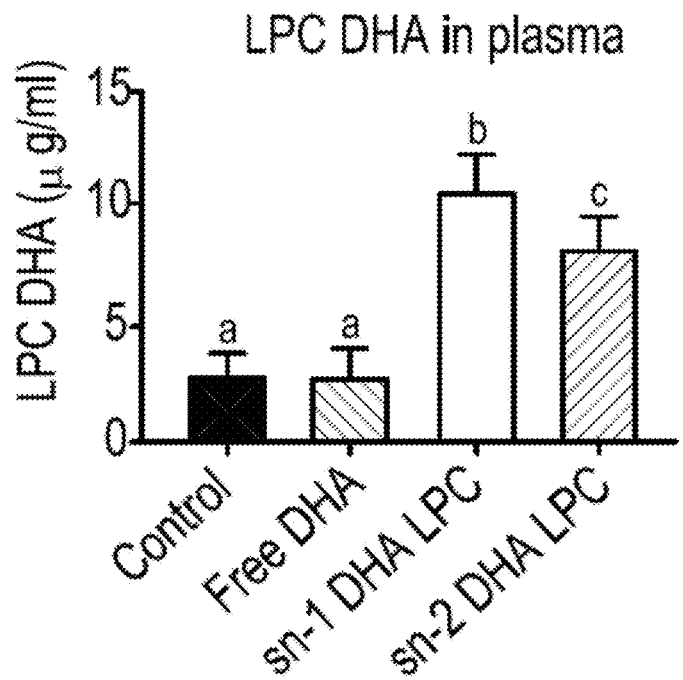
Figure 12A:
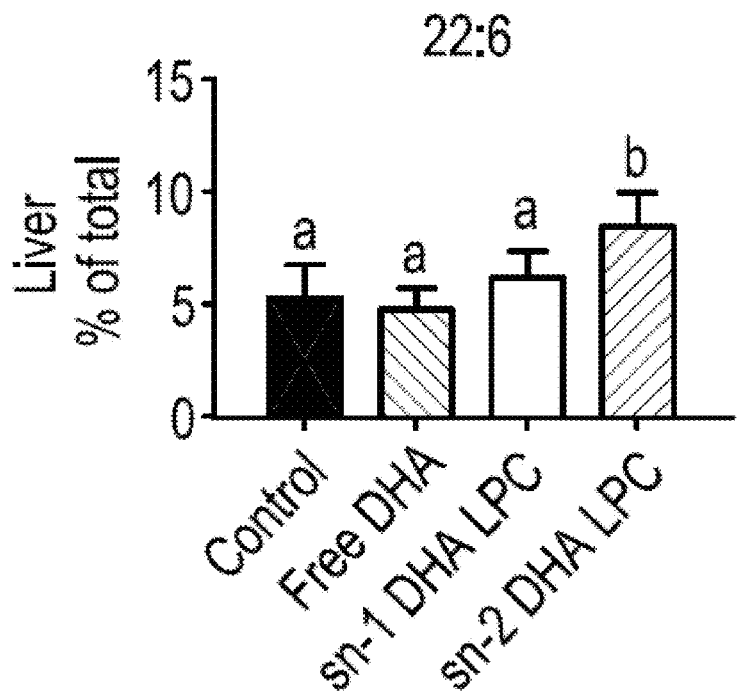
FIGS. 12A-12I shows graphs that can demonstrate the effect of molecular carrier of dietary DHA on the percentages of 22:6, 20:4, and on 22:6/20:4 ratio in liver (FIGS. 12A-12C), heart (FIGS. 12D-12F) and adipose (FIGS. 12G-12I) tissue. The values shown are mean±SD (n=8). Bars in each panel without common superscripts are significantly different from each other (p<0.05, one way ANOVA, followed by post-hoc Tukey test).
Figure 12B:
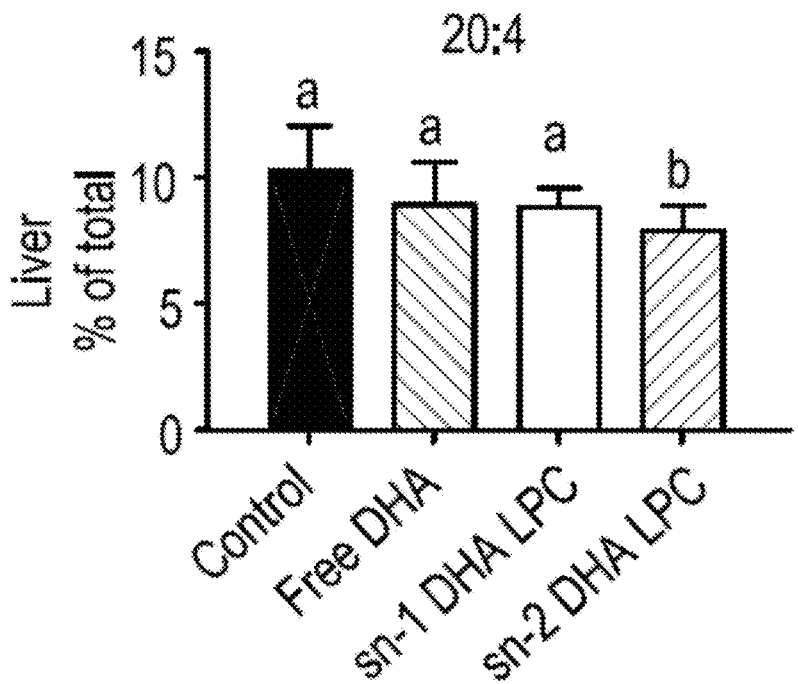
Figure 12C:
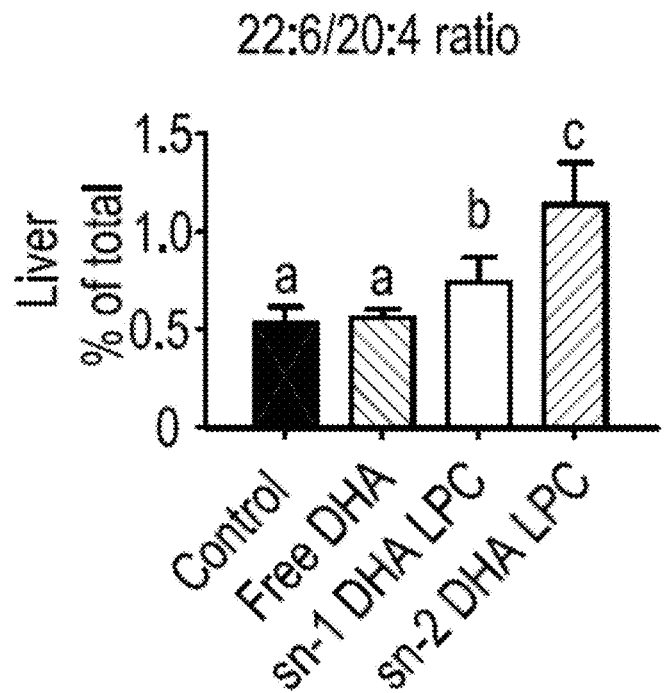
Figure 12D:
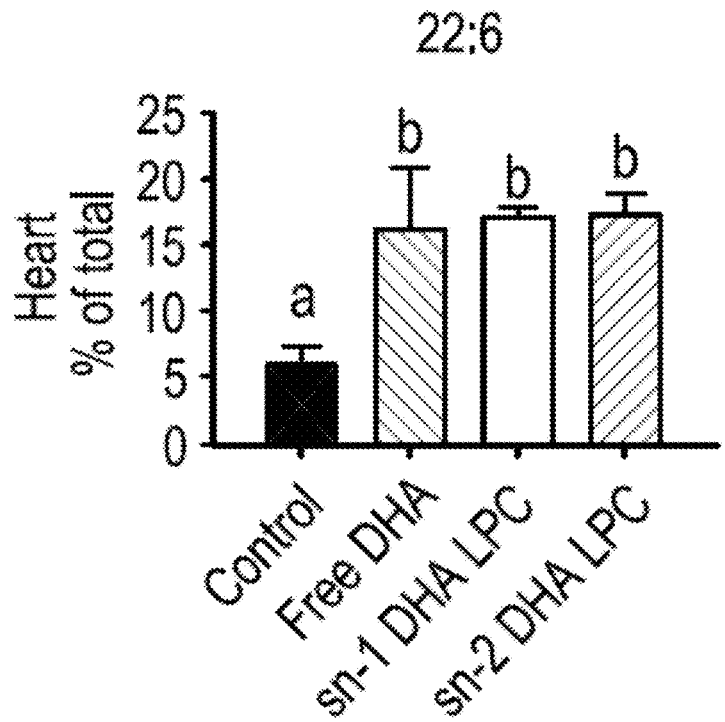
Figure 12E:
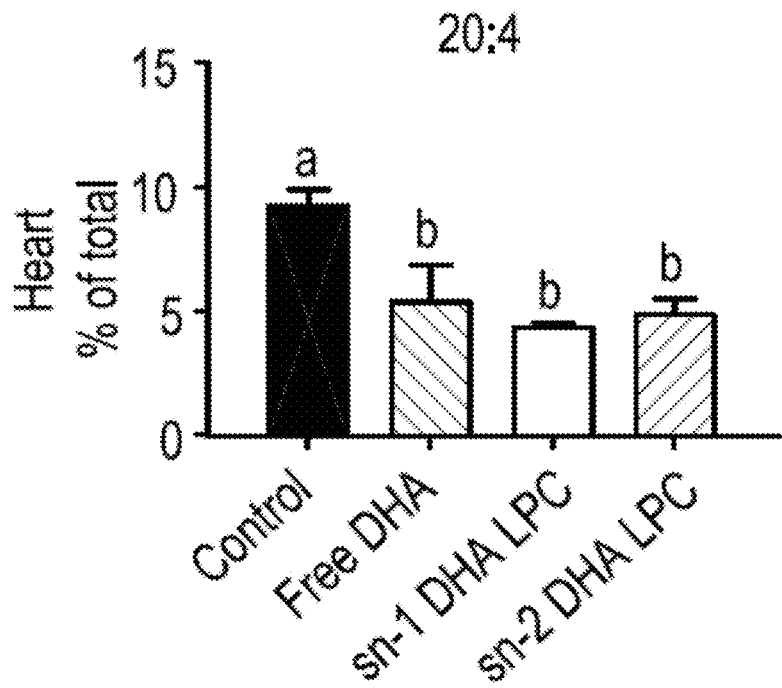
Figure 12F:
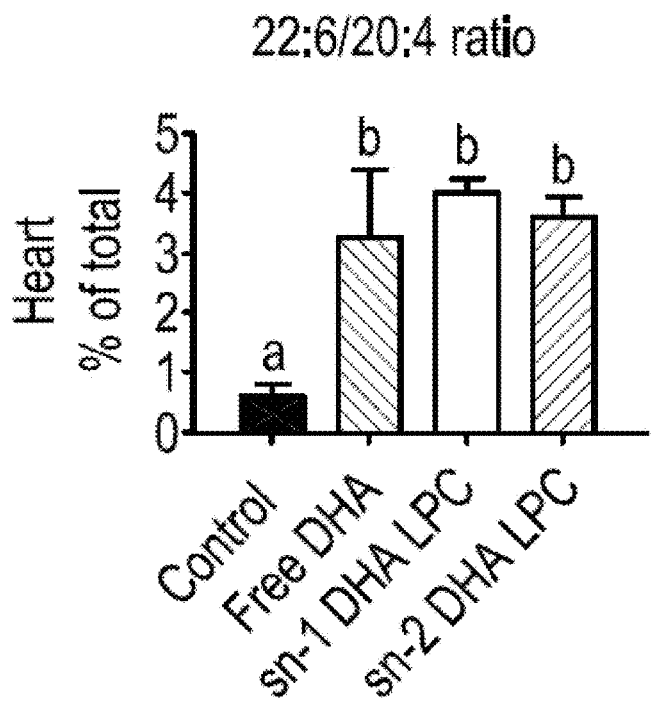
Figure 12G:
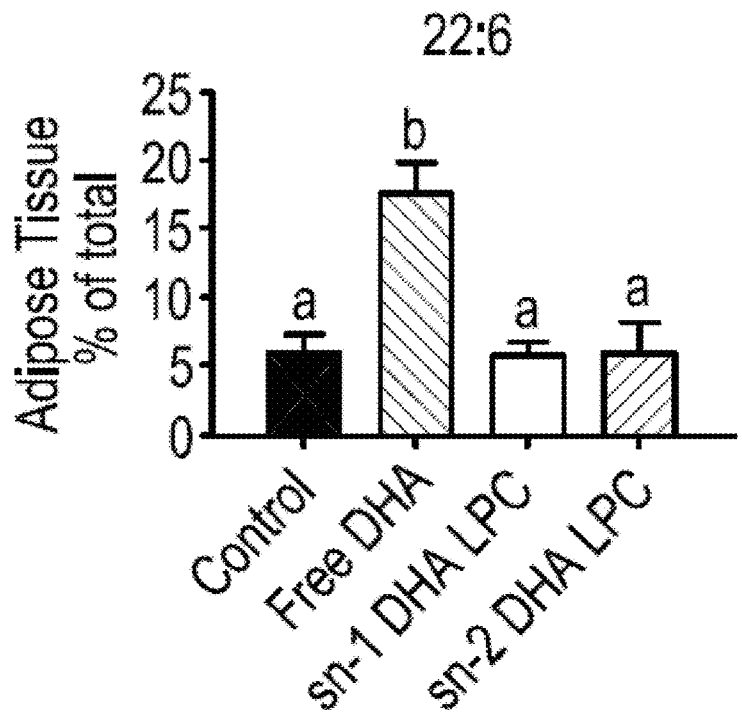
Figure 12H:
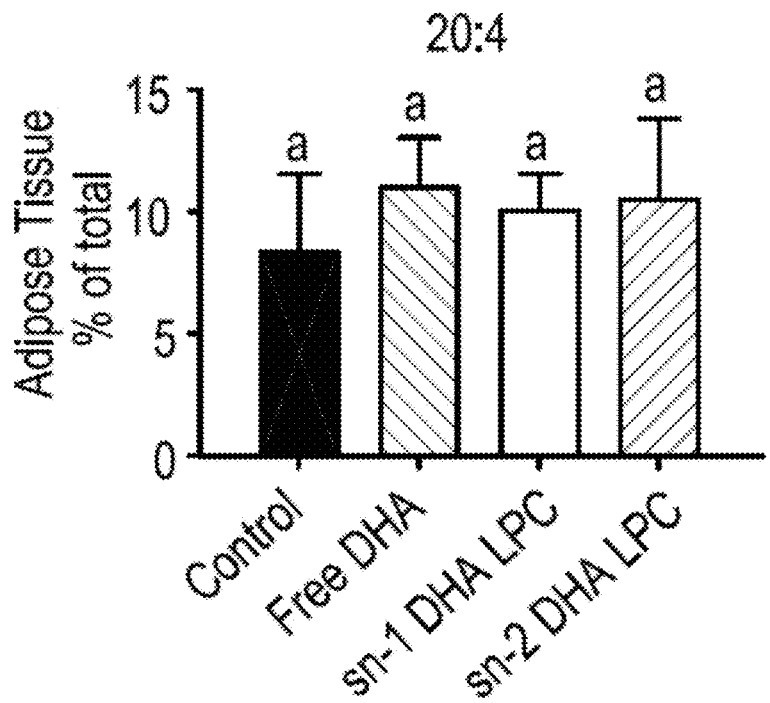
Figure 12I:
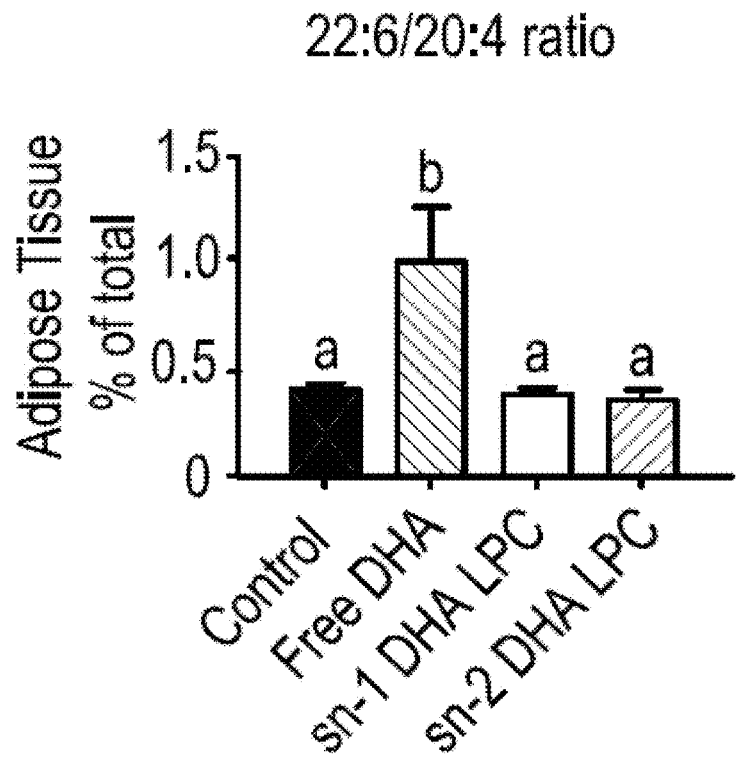

Docosahexaenoic acid (DHA), an essential omega 3 fatty acid, is uniquely concentrated in the brain, nervous tissues and retina, and is essential for the normal neurological development and function. The deficiency of DHA is associated with several neurological disorders, including Alzheimer's, Parkinson's, schizophrenia, and depression [1-5]. Unlike liver, the brain cannot efficiently convert dietary alpha linolenic acid (18:3, n-3) to DHA [6-7], and is almost completely dependent upon the uptake of preformed DHA from the plasma. However, dietary supplementation with the currently available preparations of DHA such as fish or krill oil [8], algal DHA [9], DHA-enriched egg phospholipids [10] ethyl esters [11] and sardines [12] does not appreciably increase brain DHA levels in adult mammals, although peripheral tissues are enriched with DHA under the same conditions. One possible explanation for this is that DHA from the above supplements is hydrolyzed to free DHA by the pancreatic enzymes and absorbed as triacylglycerol (TAG) in chylomicrons (FIG. 10), whereas the brain uniquely takes up DHA in the form of lysophosphatidylcholine (LPC) [13-15]. The recent demonstration of a transporter at the blood brain barrier (Mfsd2a), which specifically transports LPC-DHA, but not free DHA [16], further supports this mechanism. It is therefore necessary to increase the levels of LPC-DHA in plasma for an efficient enrichment of brain DHA. Without being bound by theory, dietary DHA can be provided in the sn-1 position of phosphatidylcholine (PC) or in the form of LPC in the diet, it should escape the hydrolysis by pancreatic $PLA_2$, and will be absorbed as PC-DHA (FIG. 10). The PC-DHA is more likely to be taken up by the brain after conversion to LPC-DHA in plasma or liver by the phospholipases, compared to TAG-DHA, which requires extensive metabolic transformations in the liver in order to form LPC-DHA. We have recently demonstrated in lymph fistula rats, that the amount of DHA that is absorbed in the form of phospholipid can indeed be increased by up to 5-fold by providing the DHA in the form of LPC, relative to free DHA, a surrogate for the currently used dietary supplements [17]. It was also observed that the incorporation of DHA into intestine-derived HDL is increased 2-fold during the absorption of LPC-DHA, compared to the absorption of free DHA. In this study, we tested the hypothesis that increasing DHA absorption in the phospholipid form not only increases brain DHA levels but also improves cognition and memory in normal adult mice. The incorporation of dietary free DHA and LPC-DHA into the brain and other tissues was compared, following daily gavage of the compounds in a corn oil vehicle for 30 days. The presence of DHA at sn-2 position of LPC can influence brain uptake and accumulation [14]. In this Example, the absorption and brain uptake of the two positional isomers of LPC-DHA (sn-1 DHA LPC and sn-2 DHA LPC) was compared. The results show that the DHA content of most regions of the brain is more than doubled by feeding either sn-1 or sn-2 DHA LPC, but not by feeding free DHA, which however enriched other tissues. Furthermore, the mice treated with both LPC-DHA isomers showed a remarkable enhancement of spatial learning and memory in the Morris water maze test. These studies are the first to demonstrate a targeted enrichment of brain DHA through diet leading to a functional improvement in memory in normal adult mice. If confirmed in humans, these studies have the potential to lead to novel nutraceutical approaches for the prevention and treatment of neurological disorders associated with low cerebral DHA levels, such as Alzheimer's, Parkinson's, schizophrenia, and depression.

Materials and Methods.

Animals.

Male C57BL/6 mice (age 16 weeks) were purchased from Jackson laboratories (Bar Harbor, Me.). The mice were acclimated for 1 week before starting the daily gavage, and were provided rodent chow (Teklad LM 485, Envigo, Indianapolis, Ind.) throughout the experiment, in addition to the daily gavage of corn oil containing the various DHA preparations.

Chemicals.

Free fatty acids (15:0, 17:0, 22:3, 22:6) were purchased from Nu-Chek Prep Inc (Elysian, Minn.). Synthetic phospholipids (16:0-22:6 PC, 17:0-17:0 PC, 17:0 LPC, and 17:0-17:0 PE) were purchased from Avanti Polar Lipids (Alabaster, Ala.). All solvents, which were of LC/MS grade, as well as Mucor lipase (Lipozyme) were obtained from Sigma/Aldrich (St. Louis, Mo.).

Preparation of Sn 2-DHA LPC and Sn 1-DHA LPC.

sn-2 DHA LPC was prepared by the hydrolysis of 16:0-22:6 PC with immobilized Mucor lipase (Lipozyme) by a modification of the published procedure[44]. Briefly, 200 mg of Lipozyme was added to 100 mg of 16:0-22:6 PC, dissolved in 2 ml of 95:5 (v/v) ethanol: water, and was incubated in the dark at 37° C. for 24 h under nitrogen, in a metabolic shaker. The reaction mixture was dried under nitrogen and extracted with 8 ml of ethanol: water: hexane (2:1:1, by v/v) mixture to remove the free fatty acid in the hexane layer. The lower layer was concentrated under nitrogen and extracted by the Bligh and Dyer procedure [45]. The preparation contained >95% of lipid phosphorus in LPC DHA and the rest in unhydrolyzed PC, as determined by TLC, and was used for feeding studies without further purification. The sn-2 DHA LPC was stored in chloroform: methanol (9:1) at −20° C. Over 90% of the LPC remained as sn-2 isomer for at least 4 weeks under these conditions. The sn-1-DHA LPC was prepared by exposing the sn-2-DHA LPC DHA to ammonia vapors at room temperature for 48 h in the dark under nitrogen. More than 95% of the 2-acyl LPC DHA was converted to 1-acyl isomer under these conditions, as determined by LC/MS.

Feeding Studies.

Male C57BL/6 mice (16 week old) from Jackson labs, weighing about 19-22 g were housed in rooms with a 12 h light/dark cycle and controlled temperature (22±2° C.). The mice were allowed free access to standard rodent chow and water throughout the study. After a 1 week acclimation, the mice were divided randomly into 4 groups of 8 animals each, and the diet was supplemented with a daily gavage of 80 µl corn oil alone (control), or the corn oil containing 1 mg DHA in the form of free (unesterified) DHA, sn-1 DHA LPC, or sn-2 DHA LPC. This supplement provided a daily dose of approximately 45 mg DHA/kg body weight. The rodent chow did not contain any DHA, but contained 17.4 mg 18:3 (n-3)/g. After 30 days of feeding (and following the cognitive tests, see below), mice were fasted overnight and were anesthetized with ketamine (90 mg/ml) and xylazine (10 mg/ml). Blood was drawn by cardiac puncture into heparinized syringe, and plasma was separated by centrifugation at 1500×g for 15 min at 4° C. The mice were then perfused transcardially with ice-cold 100 mM phosphate-buffered saline (PBS), pH 7.4, and the liver, heart, gonadal adipose tissue, and brain were harvested. The brain was dissected into five regions: cortex, cerebellum, hippocampus, striatum, and amygdala. All samples were flash frozen in liquid nitrogen, and stored at −80° C., until analysis.

A second group of mice was studied to confirm the behavioral effects of DHA, comparing only the effects of free DHA and sn-1 DHA LPC. The treatment protocol for this cohort was exactly same as the first cohort, excepting that only 5 animals were used for each group.

Lipid Extraction and Analysis.

Total lipids were extracted from plasma and various tissues by a modification of published procedure [46]. The tissue (up to 200 mg) was homogenized at 4° C. in a glass homogenizer three times with 800 µl each of 50% methanol in water containing 0.01 N HCl. A mixture of internal standards of tri-15:0 TAG, di-17:0 PC, di-15:0 PE, and 17:0 LPC (10 µg each) was included in the methanolic HCl. Chloroform (2 ml) was added and the sample vortexed for 30 s, followed by 1 ml water and vortexing for 30 s. The sample was centrifuged, and the chloroform layer was transferred to another glass tube, and the lipids were concentrated under nitrogen and re-dissolved in chloroform before further analysis.

Analysis of Fatty Acids by GS/MS.

The fatty acid composition of lipids in all tissues was analyzed by GC/MS after conversion to methyl esters [17]. Briefly, the lipids were evaporated under $N_2$ and dissolved in 0.5 ml toluene containing 25 µg of 22:3 free fatty acid and 250 µg butylated hydroxytoluene. Methanolic HCl (0.3 ml of 8% HCl in methanol) was then added, and the reaction mixture was heated under nitrogen at 100° C. for 1 h. The acid was neutralized by adding 1.0 ml of 0.33 N NaOH, and the fatty acid methyl esters were extracted twice with 3 ml of hexane. The pooled hexane extracts were evaporated under nitrogen and re-dissolved in 30 µl of hexane and 1 µl was injected into GC/MS. The analysis was carried out using a Shimadzu QP2010SE GC/MS equipped with a Supelco Omegawax column (30 m×0.25 mm×0.25µ) as described previously [17]. Total ion current in the range of 50-400 m/z was used to quantify the fatty acids, using 17:0 as the internal standard.

LC/MS Analysis of DHA Molecular Species of PC, PE, and TAG.

LC/MS analysis of molecular species was performed on an ABSciex 6500 QTRAP mass spectrometer coupled with Agilent 2600 UPLC system, as described previously [17]. Quantitation of DHA-containing molecular species PC, LPC, PE and TAG was performed from the relative intensities of the various species and corresponding internal standards (17:0-17:0 PC, 17:0 LPC, 15:0-15:0 PE, and 15:0-15:0-15:0 TAG respectively). The data processing was carried out using Analyst 1.6.2 (ABSciex, USA).

Morris Water Maze (MWM).

MWM was conducted as described in ref. [47] with slight modifications. All behavior was tracked in real time by an overhead camera and the videos analyzed using the ANY-Maze software (Stoelting). A circular pool (diameter, 120 cm; Height, 50 cm) was filled with water containing non-toxic tempera paint (maintained at 25° C.) and divided into equal-sized quadrants. Extramaze cues were placed in the four corners for spatial orientation. In the acquisition phase, mice were trained for 5 days (60 second trial time, 4 trials each day with a 20 minute inter-trial interval) to locate the hidden platform (diameter, 10 cm). The entry quadrant varied but the platform location remained constant. Latency to find the platform (s) was measured. One hour after the final acquisition trial a single 60 second probe trial was conducted with the platform removed. The latency to the target area (the previous platform location), time spent in the target quadrant, average speed and distance traveled were calculated.

Statistical Analyses.

Results are expressed as mean±SD for each experimental group. The data were analyzed by one way ANOVA followed by a post hoc Tukey test to compare the various groups. In some cases a two-way ANOVA followed by Fisher's LSD test was used. p-values less than 0.05 were considered as statistically significant. All statistical analysis was performed using GraphPad Prism 7.03 and SPSS statistical software package version 17.0.

Results.

Incorporation of Dietary DHA into Plasma and Other Tissues.

Wild type C57BL/6 mice, maintained on normal rodent chow, were gavaged daily with 80 µl of corn oil alone (control), or the corn oil containing 1 mg DHA in the form of free fatty acid, sn-1 DHA LPC, or sn-2 DHA LPC for 30 days. The food intake, and the body weights were not significantly different between the 4 groups of mice. Following the cognitive tests (see below), the mice were sacrificed and the fatty acid composition of various tissues was analyzed by GC/MS. The effect of dietary supplementation with different DHA preparations on the DHA content (% of total fatty acids) of plasma, liver, heart, and adipose tissue is shown in FIGS. 11A-11D and 12A-12I. In addition to DHA, the percentages of arachidonic acid (ARA, 20:4) are shown, since DHA has been reported to replace predominantly ARA in most tissues, and since the 22:6/20:4 ratio provides one measure of the anti-inflammatory potential in the tissues [18]. In the plasma, there was a significant increase in the percentage of DHA by all three preparations of DHA, although the increase was greater in the groups treated with LPC DHA than the mice treated with free DHA (FIGS. 11A-11D). However, there was also an increase in the percentage of 20:4 with all three DHA preparations, resulting in no significant change in the ratio of 22:6/20:4. The reason for the increase in plasma ARA is not clear, although it is decreased in most tissues where DHA is increased (see below). One possible explanation is that the tissue ARA replaced by DHA is released as free ARA into the plasma. The concentration of LPC DHA in plasma was also determined by LC/MS/MS. As shown in FIGS. 11A-11D, the LPC DHA concentration of plasma increased significantly in mice treated with either isomer of LPC DHA, but not in mice treated with free DHA. Although we did not analyze the isomer composition of plasma LPC DHA because of insufficient material, the increase was 28% higher after the feeding of sn-1 DHA LPC compared to sn-2 DHA LPC.

Figure 17:
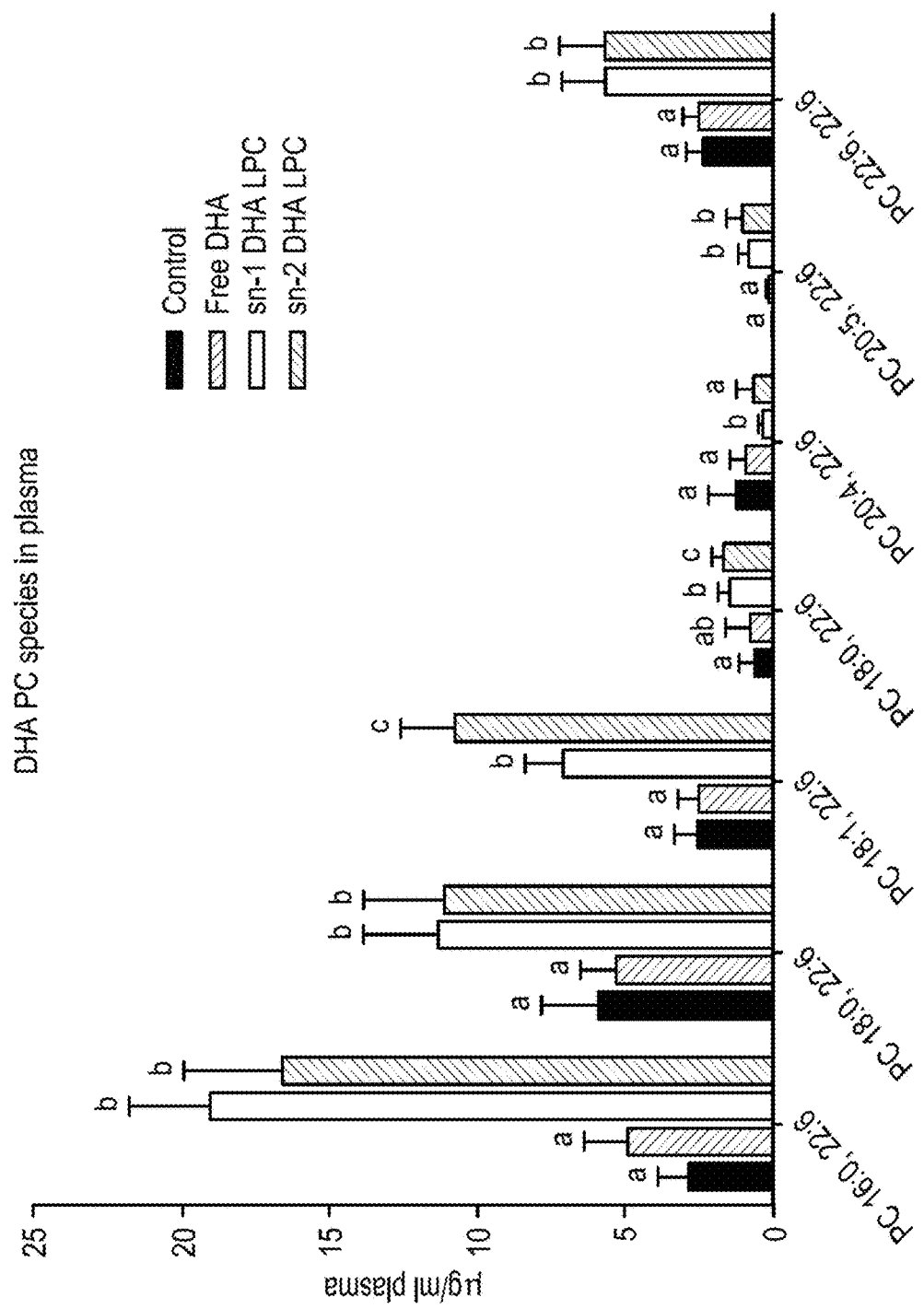
FIG. 17 shows a graph that can demonstrate the molecular species of PC containing DHA in plasma of mice treated with various molecular carriers of dietary DHA. The PC species were determined by LC/MS/MS in MRM mode, using 17:0-17:0 PC as internal standard. Bars containing non-identical letters for each PC species are significantly from each other by one way ANOVA and post-hoc Tukey test.
Figure 18:
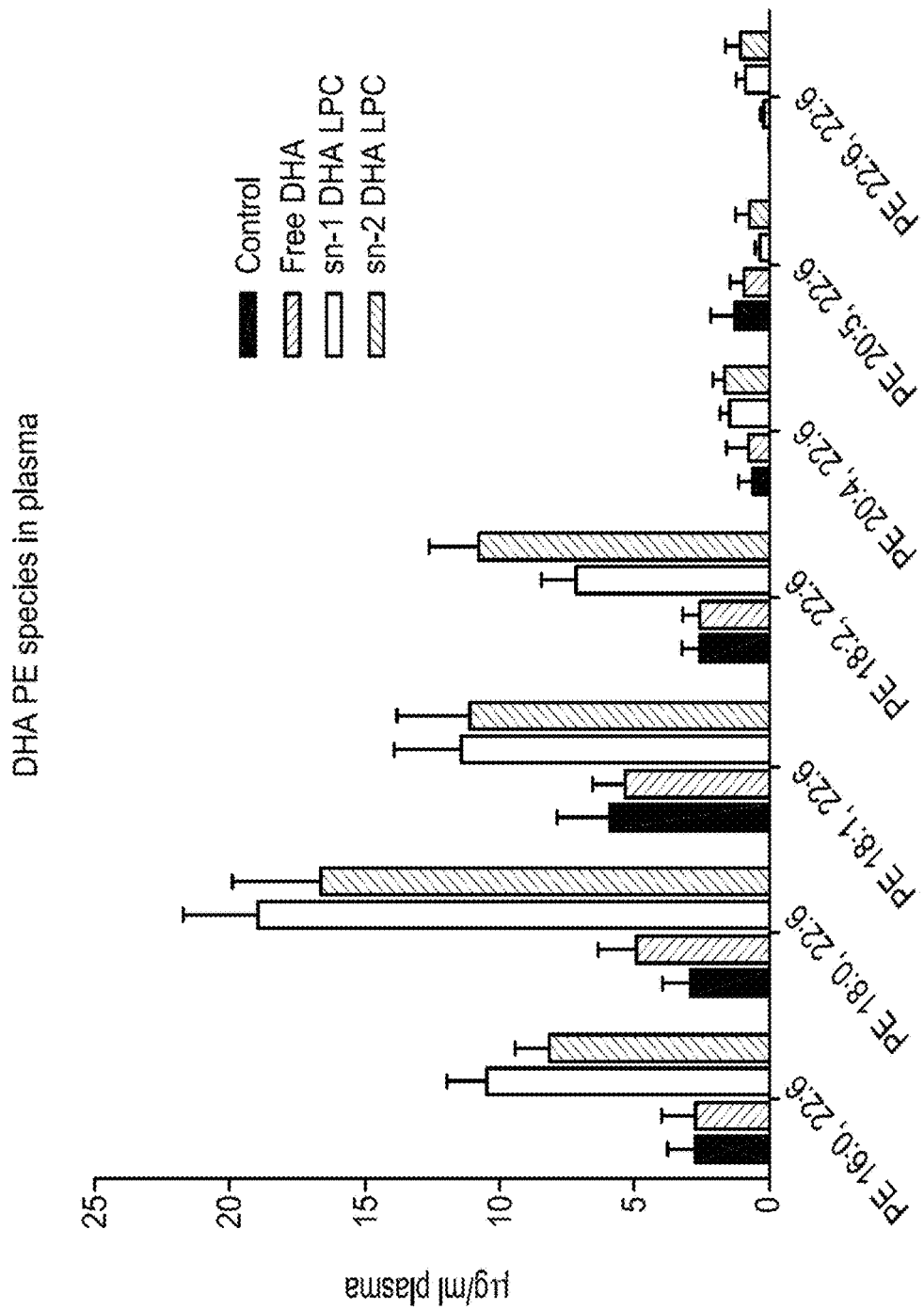
FIG. 18 shows a graph that can demonstrate the molecular species of DHA-containing PE in plasma of mice treated with different molecular carriers of dietary DHA. The PE species were determined by LC/MS/MS in MRM mode, using 15:0-15:0 PE as internal standard. Values shown are mean±SD (n=8), and the bars for each PE species not sharing common letters are significantly different from each other by one way ANOVA and post-hoc Tukey test.
Figure 19:
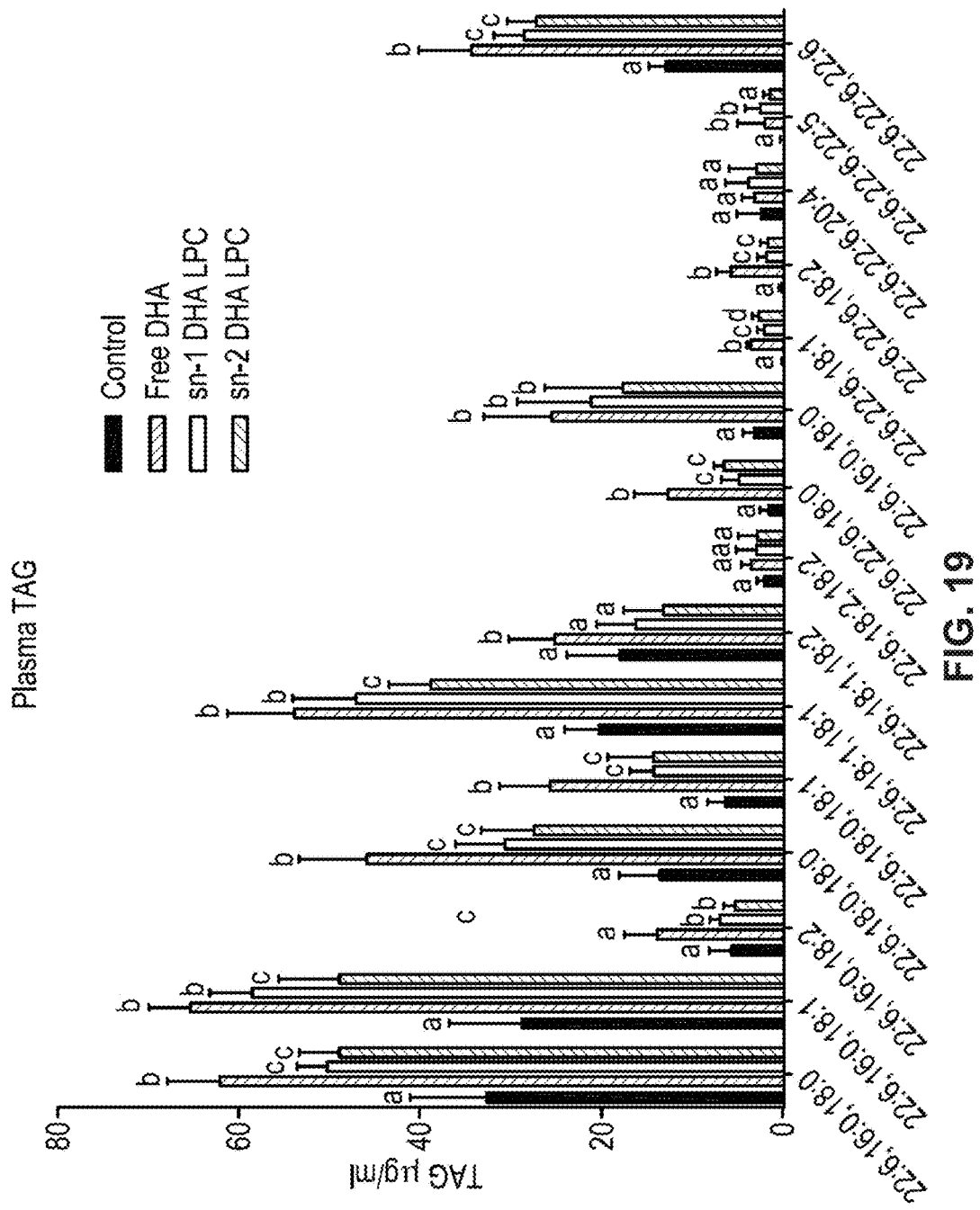
FIG. 19 shows a graph that can demonstrate the molecular species of DHA-containing TAG in plasma after treatment with different molecular carriers of dietary DHA. The TAG species were analyzed by LC/MS/MS in MRM mode, using 15:0-15:0-15:0 as internal standard. Values shown are mean±SD (n=8), and the bars for each TAG species not sharing common letters are significantly different from each other by one way ANOVA and post-hoc Tukey test.

The molecular species of DHA-containing lipids (PC, PE. TAG) in plasma were analyzed by LC/MS/MS, to determine the metabolic fates of the absorbed DHA. Most of the DHA-PC species were increased by treatment with both the LPC isomers, but not with free DHA (FIG. 17). There was no significant difference between the two LPC isomers, except for a greater increase in 18:1-22:6 PC in the sn-1 DHA LPC group. The molecular species of DHA-PE were also increased by the two LPC DHAs, but not by free DHA (FIG. 18). In contrast to the plasma phospholipids, the plasma TAG species containing DHA were increased more by free DHA than by the LPC DHA (FIG. 19).

The DHA concentration in liver was significantly increased only in the mice fed sn-2 DHA LPC, with a parallel decrease in the concentration of 20:4 and an increase in the 22:6/20:4 ratio (FIGS. 12A-12I). Although the increase in DHA after feeding sn-1 DHA LPC did not reach statistical significance, the ratio of 22:6/20:4 was significantly increased. All three preparations of DHA increased the percentage of DHA in the heart, at the expense of 20:4, resulting in a significant increase in the ratio of 22:6/20:4 in all three groups of animals, compared to the controls. In contrast to the liver and heart, the adipose tissue showed an increase in DHA concentration, as well as in the 22:6/20:4 ratio after the feeding of free DHA, but not after feeding of either isomer of LPC-DHA. These results show that the dietary free DHA is predominantly directed to adipose tissue and heart in the form of TAG, whereas dietary LPC-DHA was directed to the brain in the form of phospholipid (see below).

Incorporation of DHA into Various Regions of the Brain.

Figure 13A:
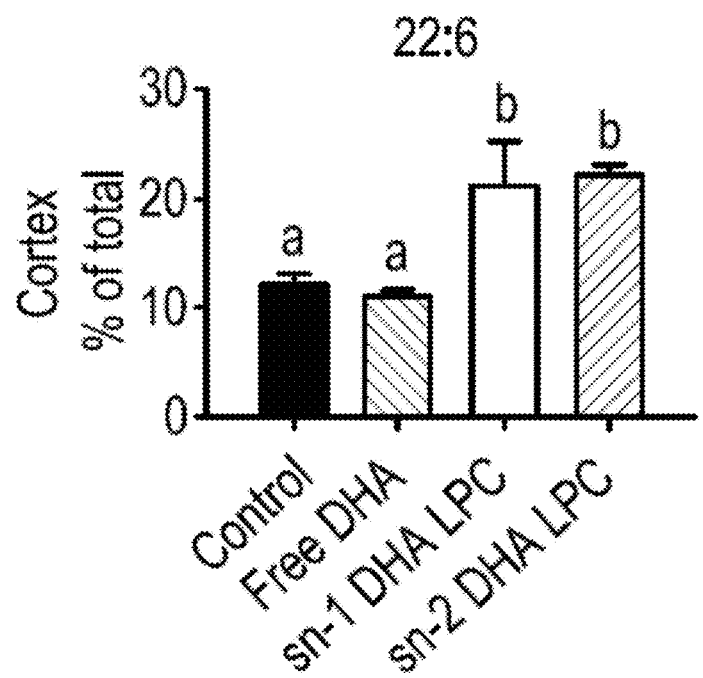
FIGS. 13A-13O show graphs that can demonstrate the effect of dietary treatment with free DHA, sn-1 DHA LPC, and sn-2 DHA LPC on the levels (percentages of total fatty acids) of 22:6 and 20:4 and on the 22:6/20:4 ratios in various regions of the brain: the cortex (FIGS. 13A-13C), the cerebellum (FIGS. 13D-13F), the hippocampus (FIGS. 13G-13I), the striatum (FIGS. 13J-13L), the amygdala (FIGS. 13M-13O). The values shown are mean±SD (n=8, for all regions, except for Amygdala, where n=6). The bars in each figure not sharing common letter are significantly different from each other (p<0.05, one way ANOVA, and post-hoc Tukey test).
Figure 13B:
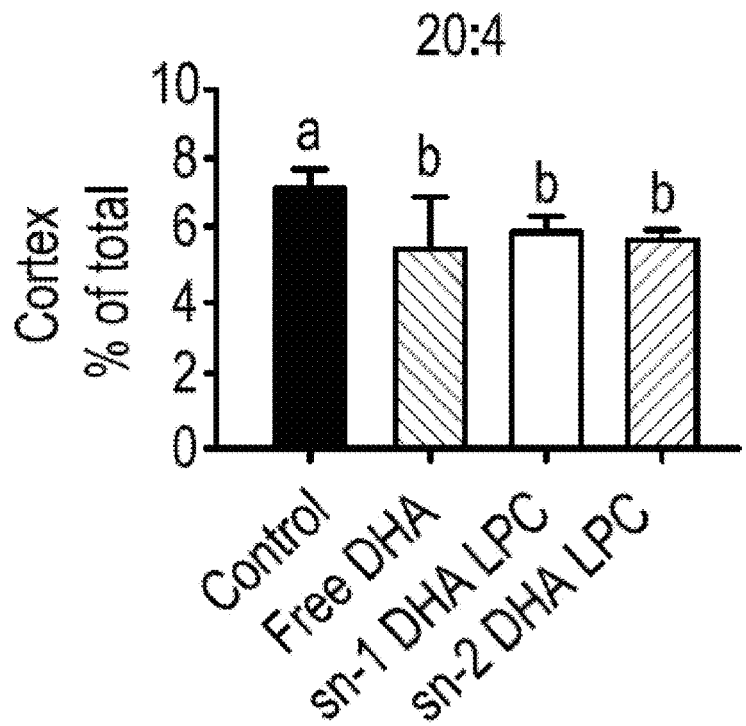
Figure 13C:
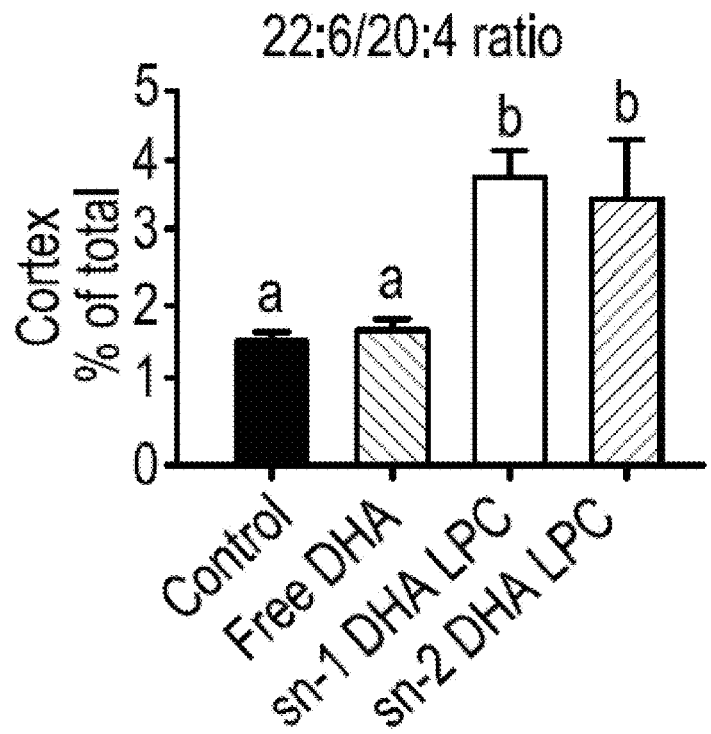
Figure 13D:
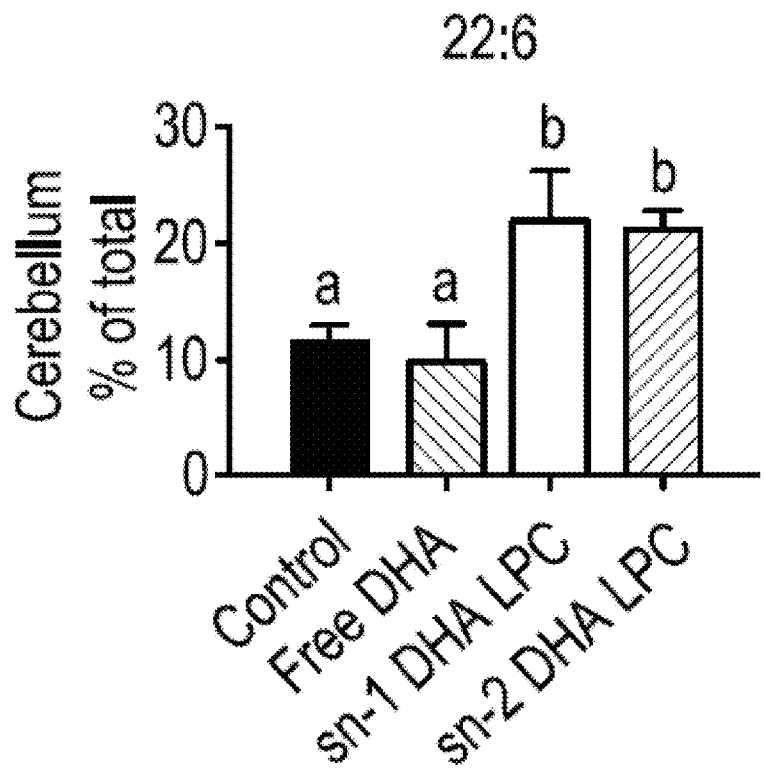
Figure 13E:
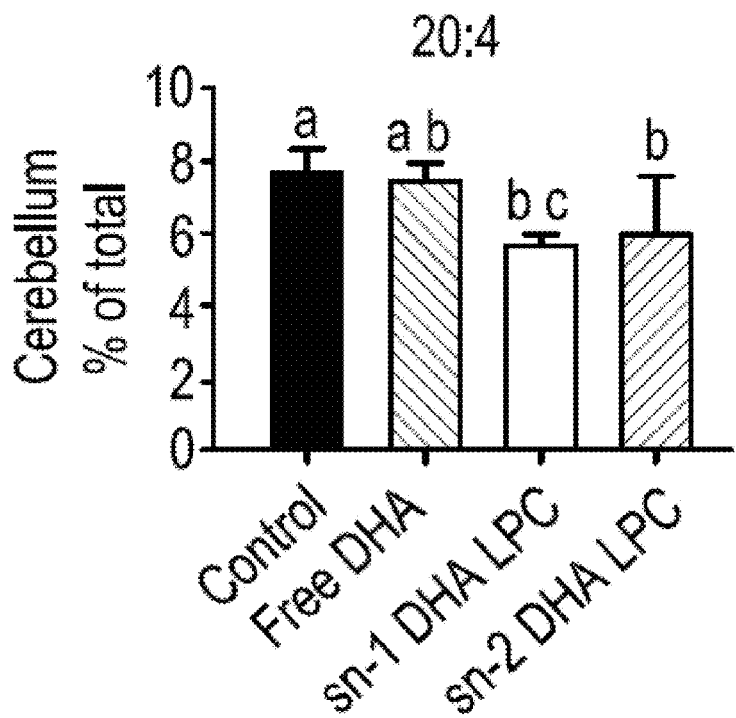
Figure 13F:
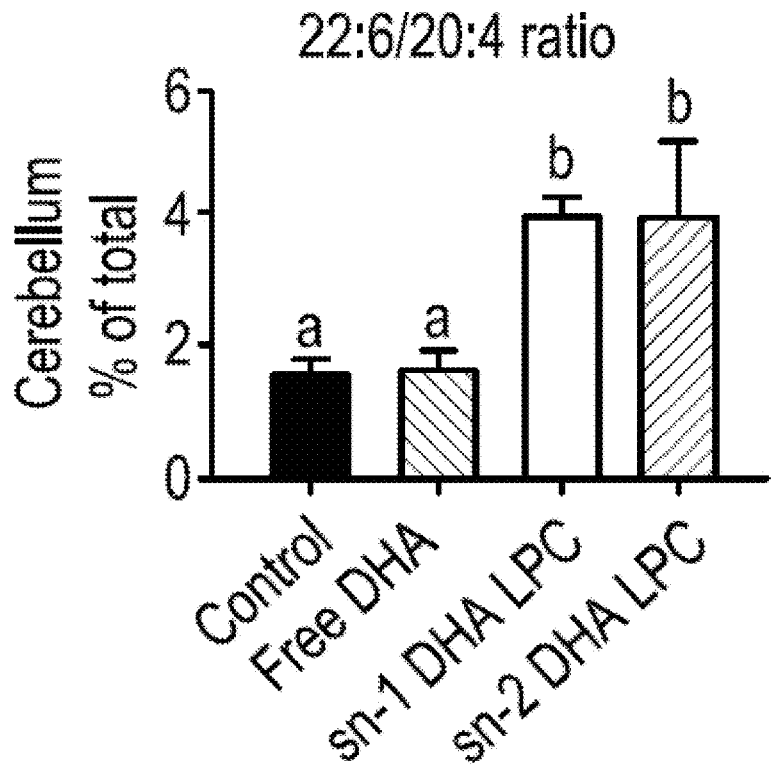
Figure 13G:
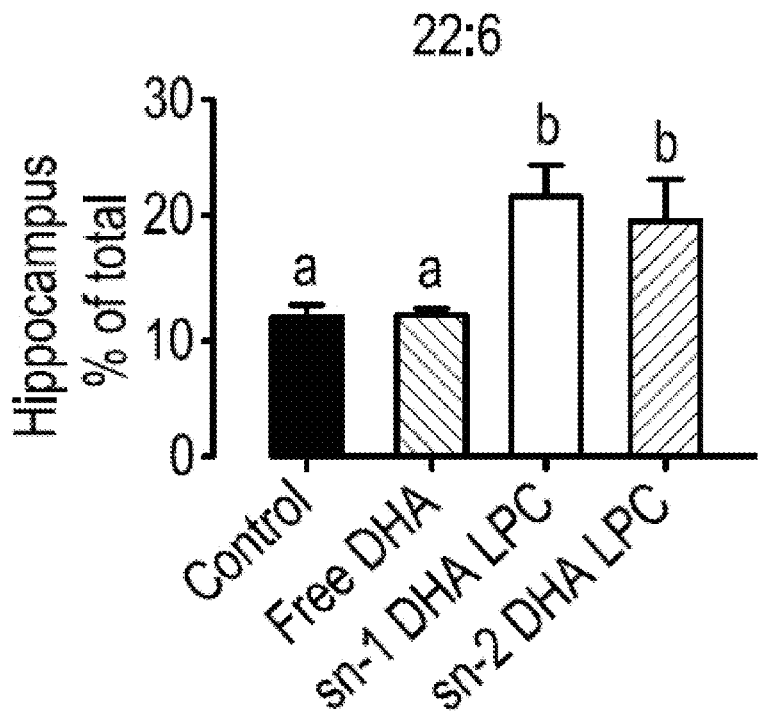
Figure 13H:
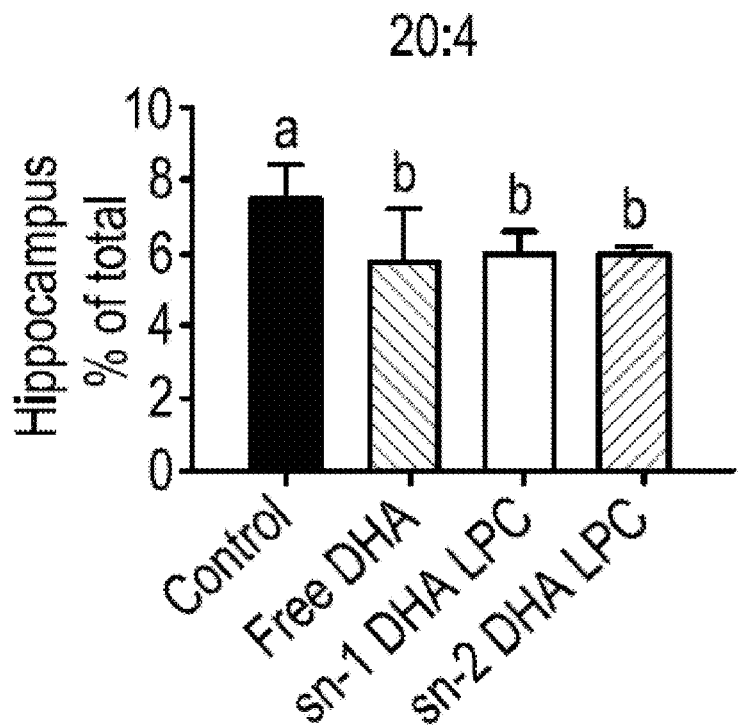
Figure 13I:
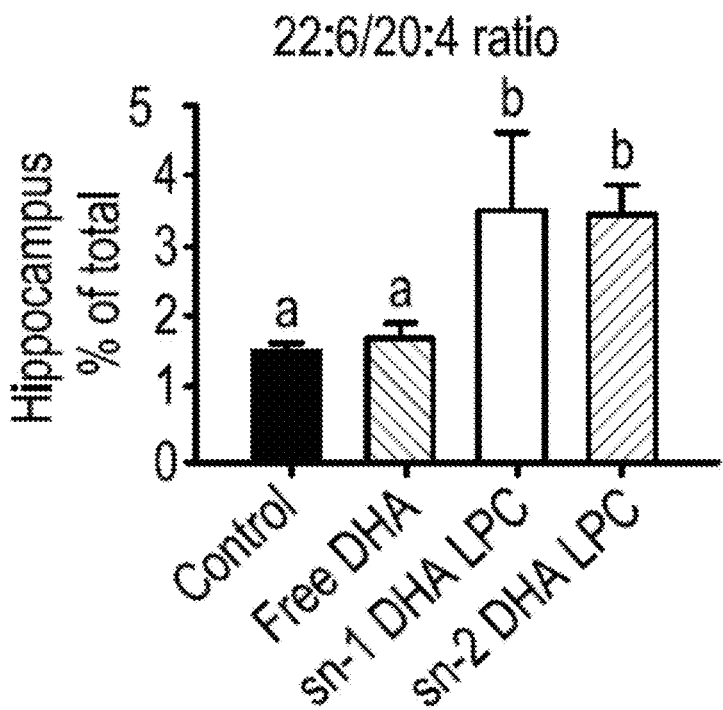
Figure 13J:
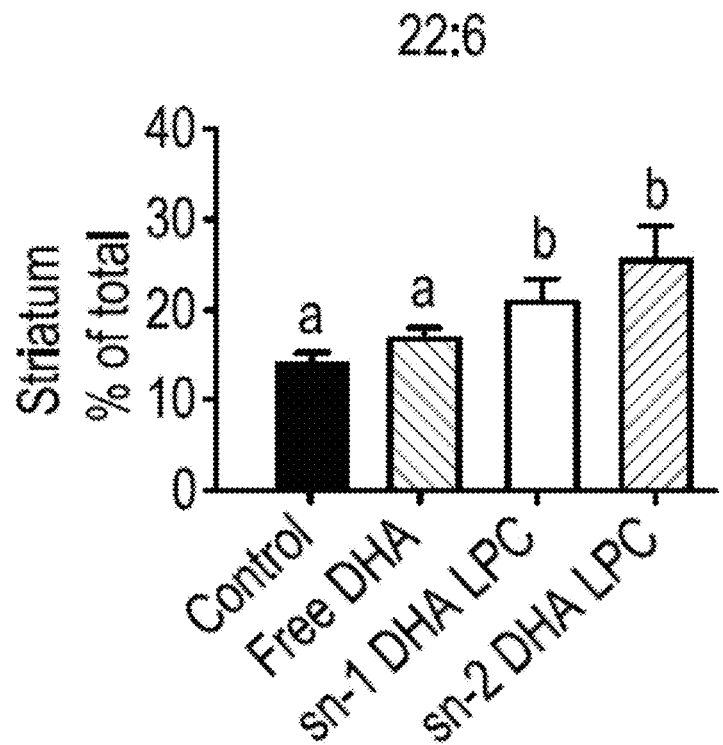
Figure 13K:
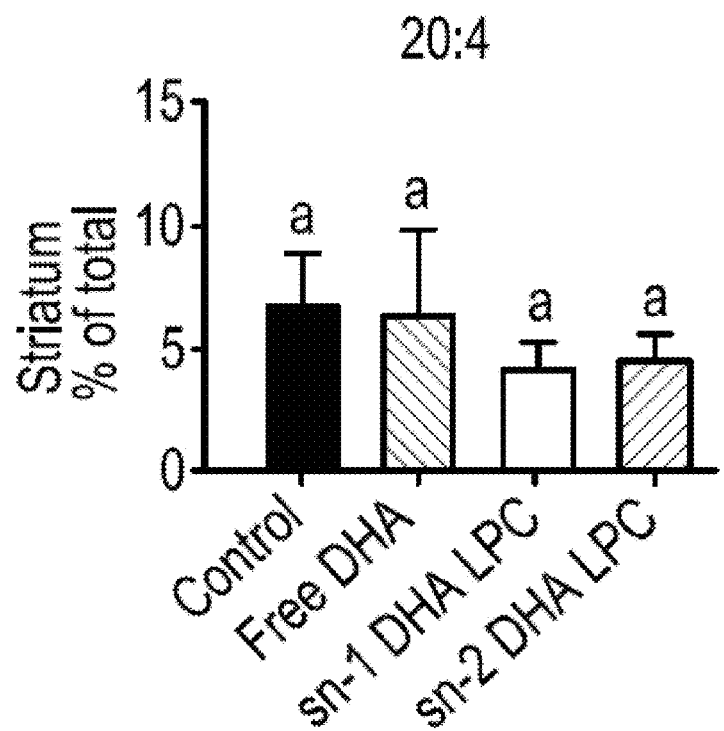
Figure 13L:
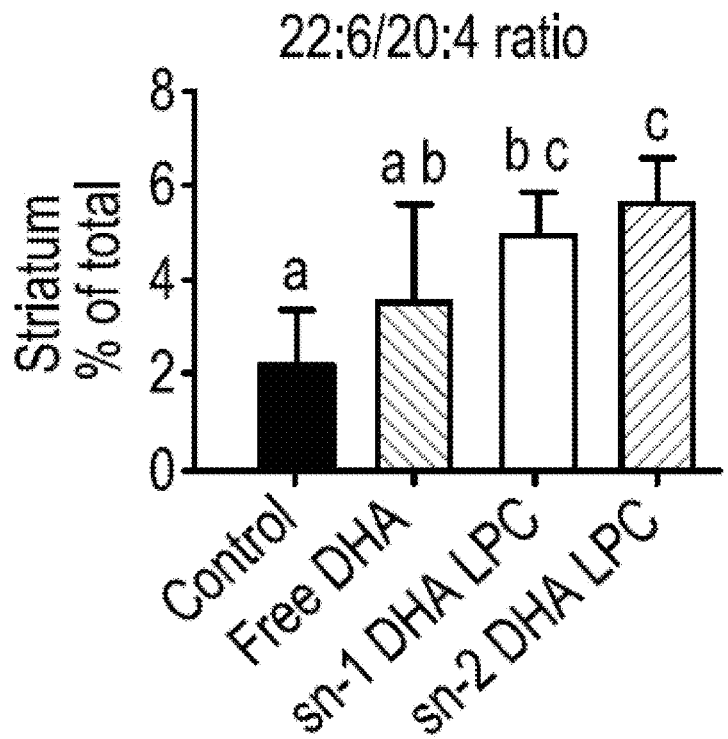
Figure 13M:
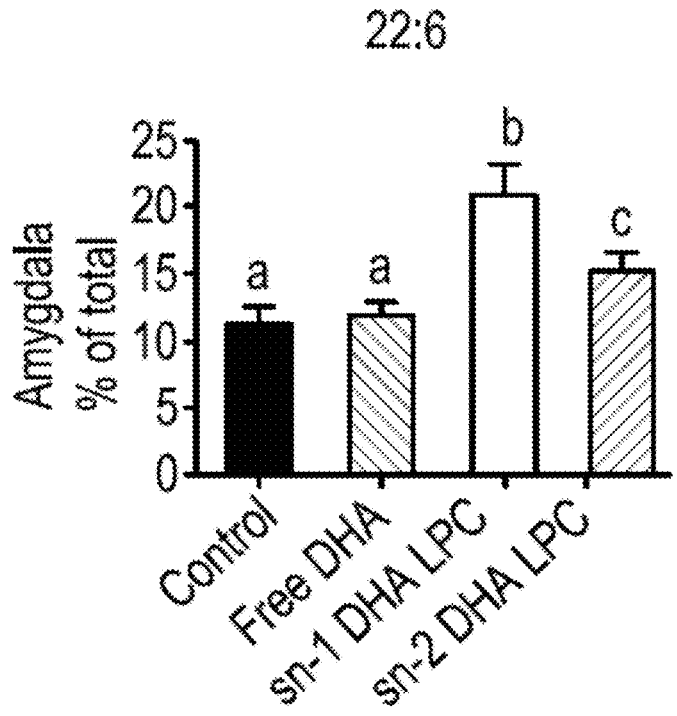
Figure 13N:
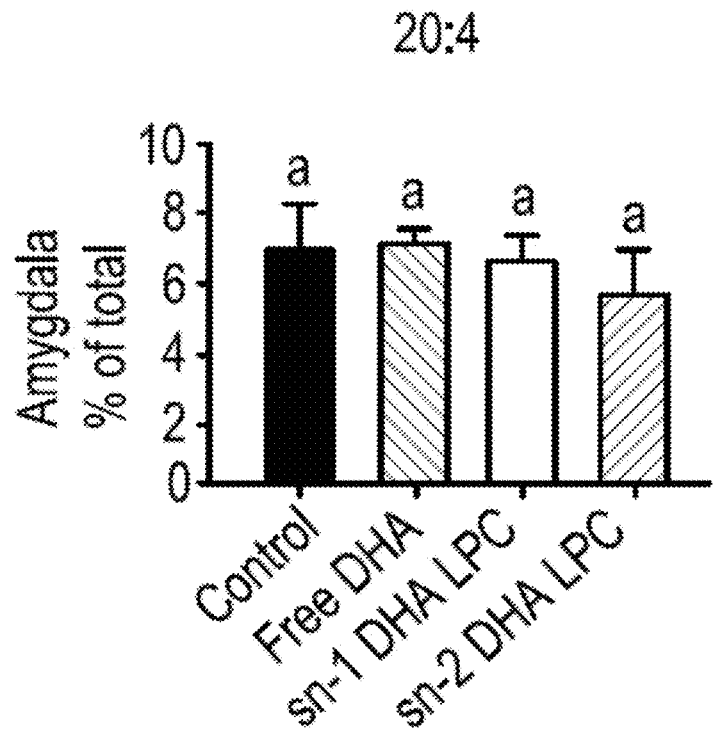
Figure 13O:
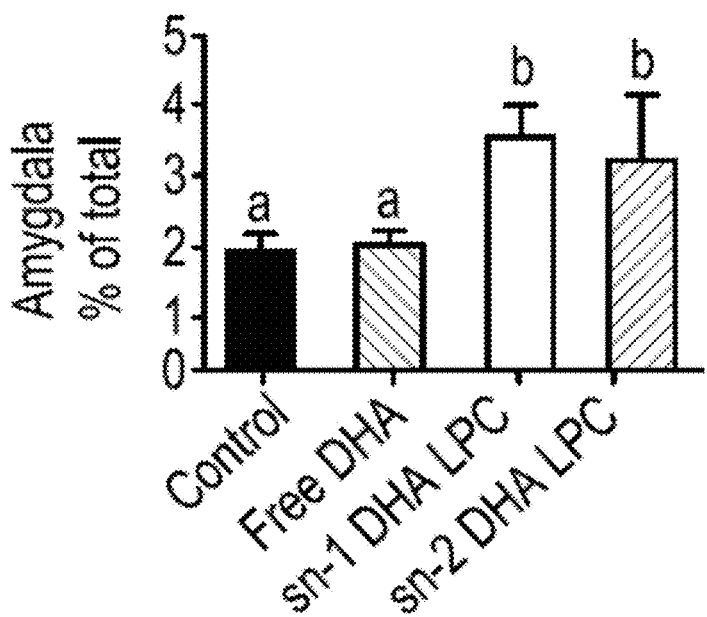
Figure 14A:
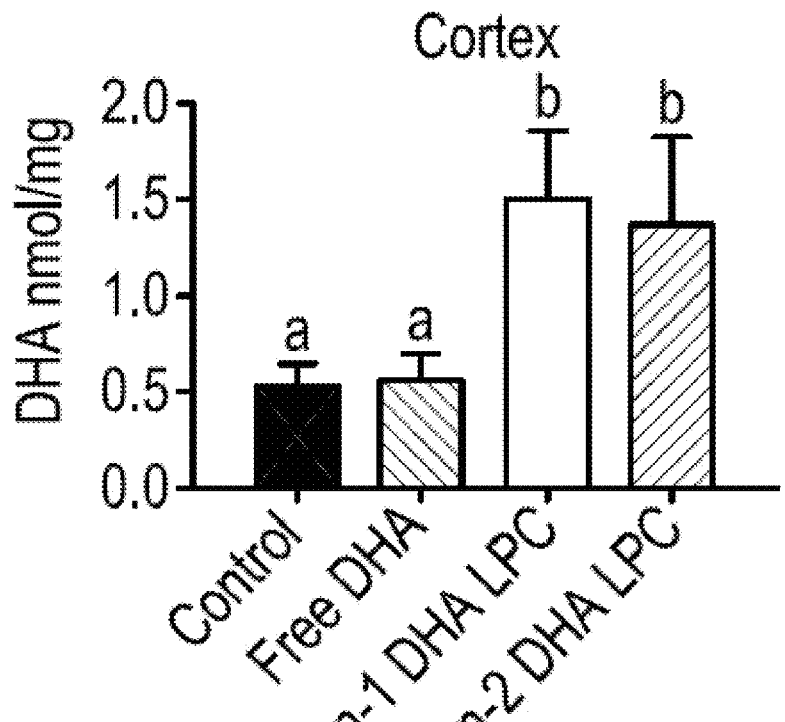
FIGS. 14A-14E show graphs that can demonstrate the effect of dietary free DHA, sn-1 DHA LPC, and sn-2 DHA LPC on the DHA concentration in various regions of brain: the cortex (FIG. 14A), the Hippocampus (FIG. 14B), the cerebellum (FIG. 14C); the striatum (FIG. 14D), and amygdala (FIG. 14E), expressed as nmol/mg tissue. The values shown are n=8, for all regions, except for Amygdala, where n=6. Bars with non-identical letters on top are significantly different from each other (p<0.05, one way ANOVA, and post-hoc Tukey test).
Figure 14B:
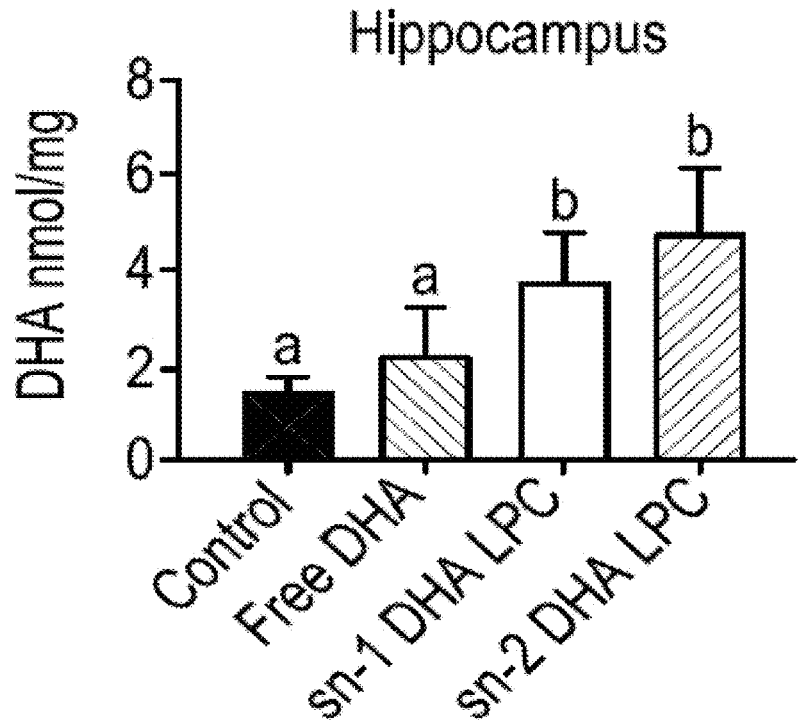
Figure 14C:
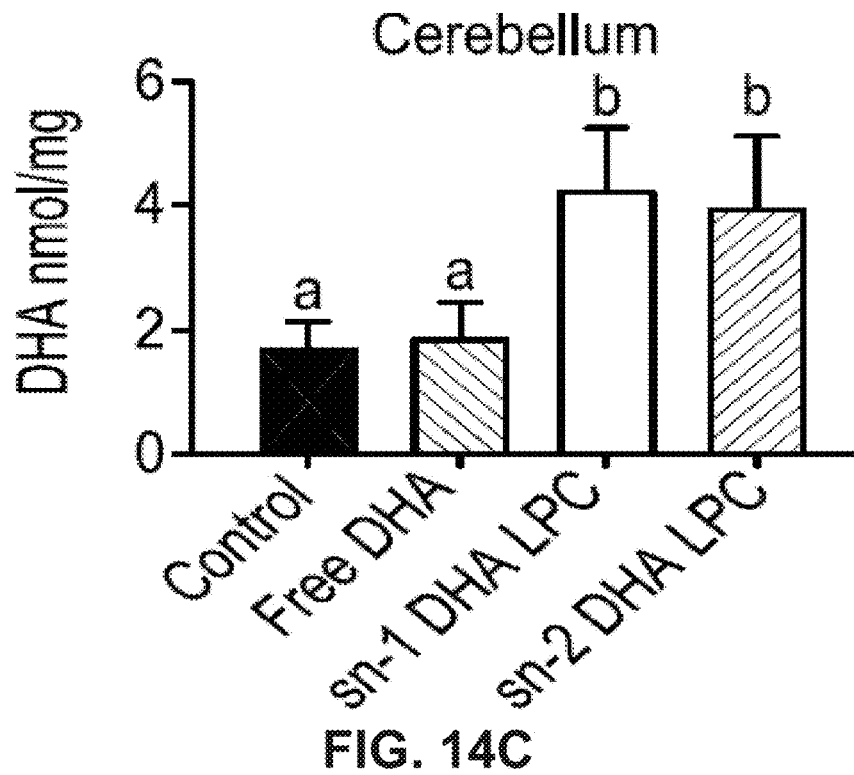
Figure 14D:
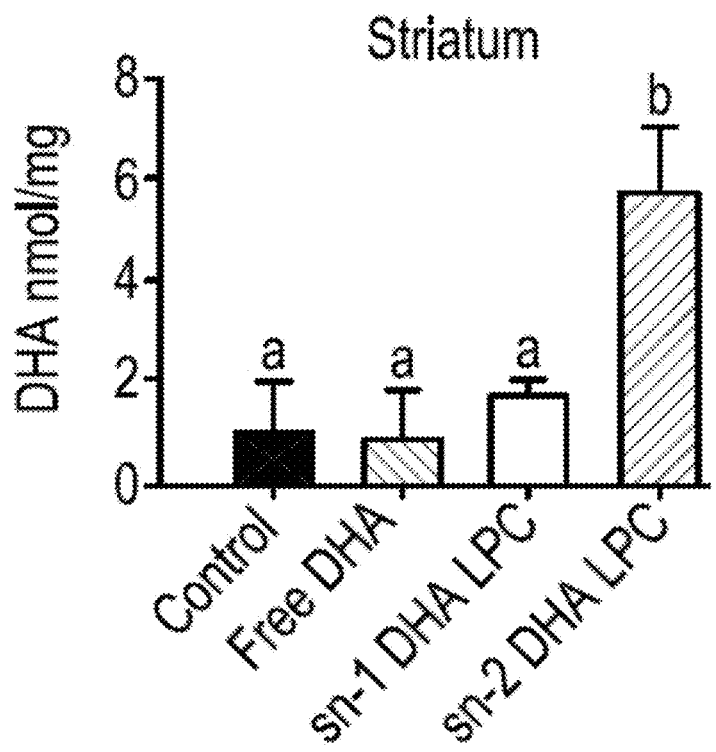
Figure 14E:
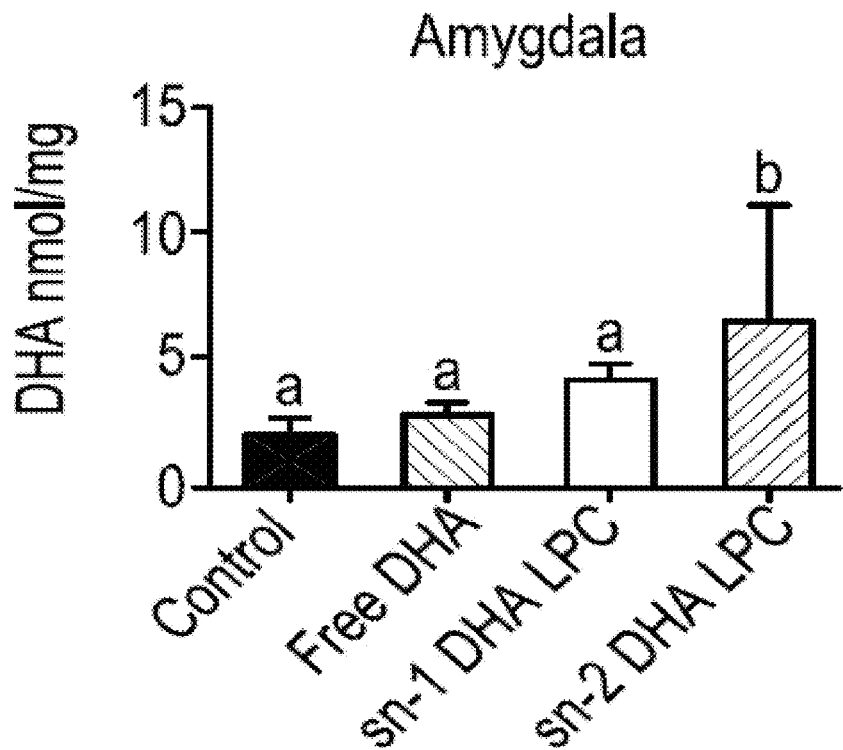

The DHA and ARA concentrations of five brain regions are shown in FIGS. 13A-13O. In contrast to the other tissues, all the brain regions were significantly enriched with DHA after the feeding either sn-1 DHA LPC or sn-2 DHA LPC, but not free DHA. The concentration of ARA was correspondingly decreased after feeding either isomer of LPC, and the 22:6/20:4 ratio more than doubled in all regions of brain. On the other hand, there was no significant increase in this ratio in any brain region after the feeding free DHA. These results show that the brain DHA responds specifically to treatment with dietary LPC-DHA. No difference between the two isomers of LPC-DHA in their ability to enrich brain DHA was observed, although previous studies suggested that the sn-2 DHA LPC can be preferentially taken up by the brain.

Figure 20:
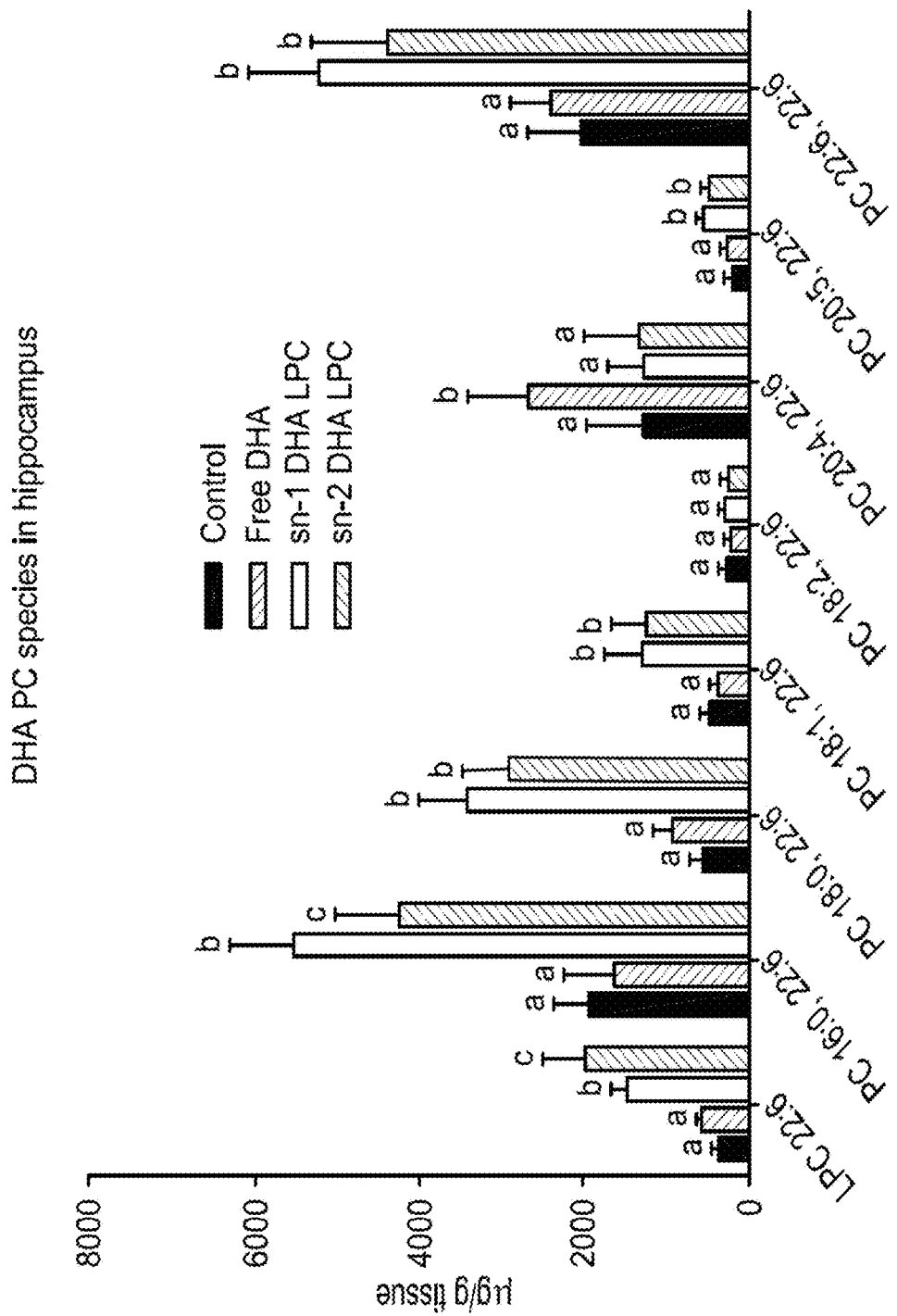
FIG. 20 shows a graph that can demonstrate the molecular species of DHA-containing PC species in hippocampus of mice treated with different molecular carriers of dietary DHA. Values shown are mean±SD (n=8), and the bars for each PC species without common letters on top are significantly different from each other by one way ANOVA and posthoc Tukey test.
Figure 21:
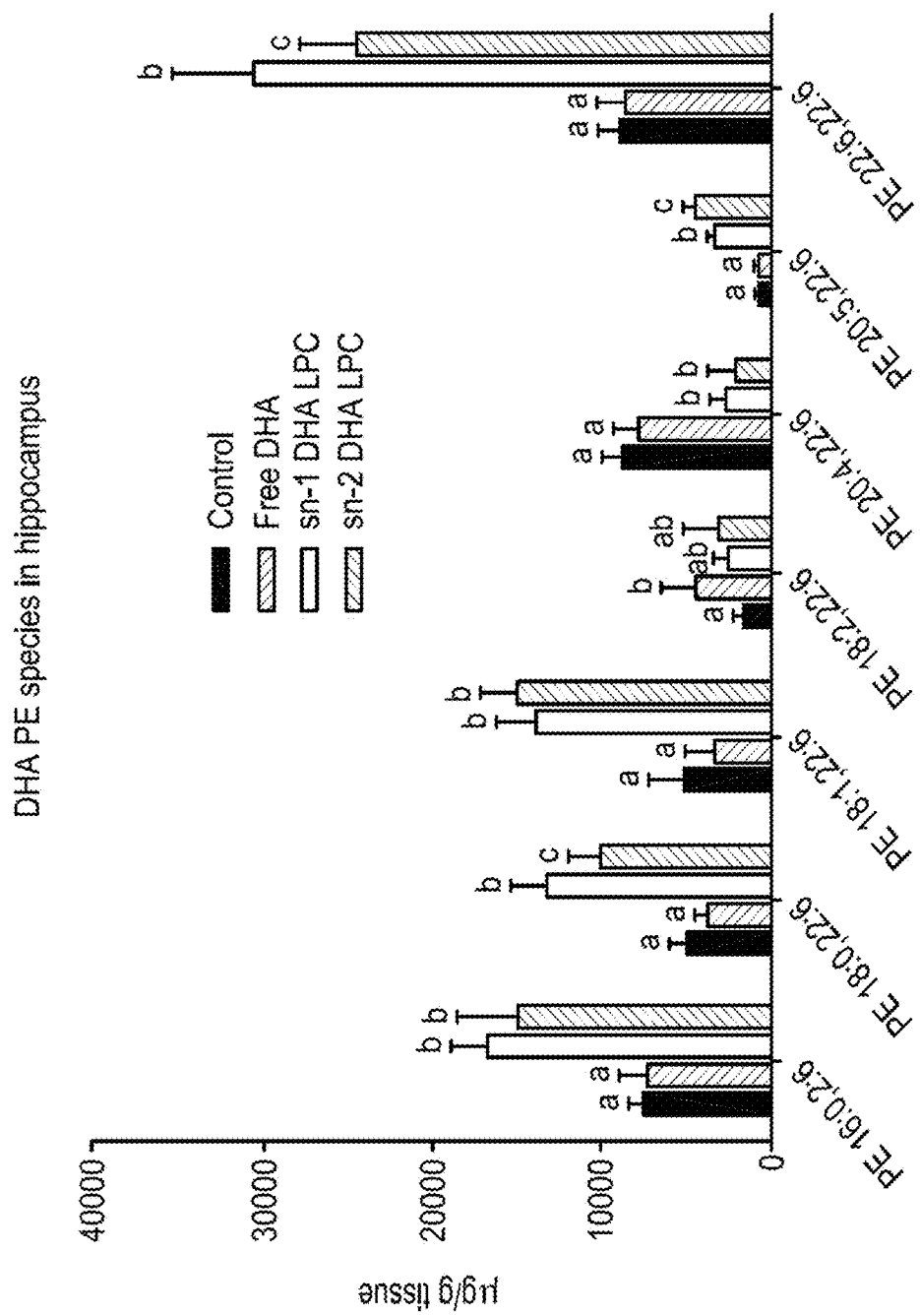
FIG. 21 shows a graph that can demonstrate the molecular species of DHA-containing PE species in hippocampus of mice treated with different molecular carriers of dietary DHA. Values shown are mean±SD (n=8), and the bars for each PE species not sharing common superscript are significantly different from each other by one way ANOVA and posthoc Tukey test.

The increase in brain DHA content by dietary LPC-DHA, but not free DHA, was also evident when the results are expressed as nmol of DHA per mg wet weight of the tissue. By this measure, the DHA content increased by 2-3 fold in most regions of the brain after LPC-DHA treatment, except in the case of striatum and amygdala where the increase in the sn-1 DHA group did not reach statistical significance (FIGS. 14A-14E). The molecular species of DHA-containing PC and PE in the hippocampus by LC/MS/MS was also determined, to investigate the incorporation profiles of DHA derived from dietary free DHA and LPC-DHA (FIG. 20). The amount of LPC-DHA, as well as most species of DHA-PC were increased by both isomers of dietary LPC-DHA, but not by free DHA. One exception was 20:4-22:6 PC, which was increased by free DHA, but not by the two LPC-DHAs. The major species of DHA-PE were also increased by the dietary LPC-DHAs, but not by free DHA (FIG. 21). Interestingly, the net increase in the amount of hippocampal PE-DHA was 4-fold higher than the net increase in PC-DHA by both isomers of dietary LPC-DHA, showing that the majority of DHA derived from dietary LPC-DHA was ultimately incorporated into brain PE.

Effect of Dietary DHA on Brain Function.

Figure 15A:
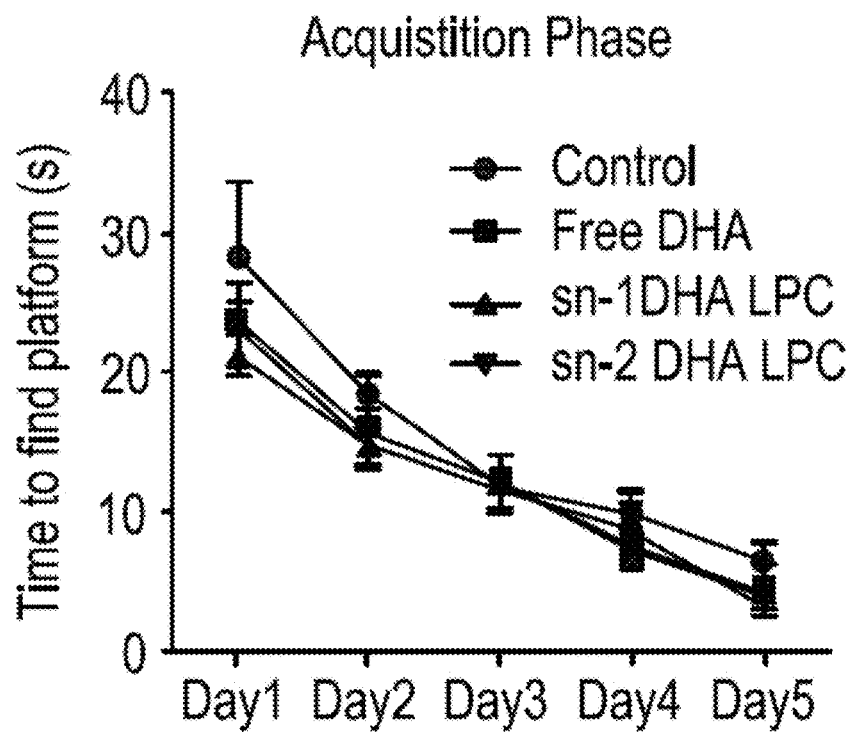
FIGS. 15A-15F show graphs that can demonstrate that memory is improved in mice treated with LPC DHA compared to control or free DHA treated mice. In study 1 (FIGS. 15A-15C), Morris water maze tests of mice treated with vehicle (control), free DHA, sn-1 DHA LPC, and sn-2 DHA LPC for 1 month are shown. LPC DHA-treated mice did not differ from control or free DHA mice in the acquisition phase (FIG. 15A). In the probe trial (FIGS. 15B-15C) both sn-1 DHA LPC and sn-2 DHA treated mice reached the previous platform area with shorter latency time, and spent longer in the target quadrant. Data expressed as mean±S.D (n=8). Bars with non-identical letters are significant from each other (p<0.05), by two-way ANOVA followed by Tukey's post hoc comparisons. In a second study (FIGS. 16D and 16e-16F) to validate the above results, only 2 groups were used and were treated either with free DHA or sn-1 DHA LPC for 1 month. As in the first study, sn-1 DHA LPC treated mice reached the previous platform area with a lower latency time, and spent longer in the target quadrant compared to free DHA group n=5 each. Data expressed as mean±S.D. p<0.05 by two-way ANOVA followed by Sidak's post hoc comparisons.
Figure 15B:
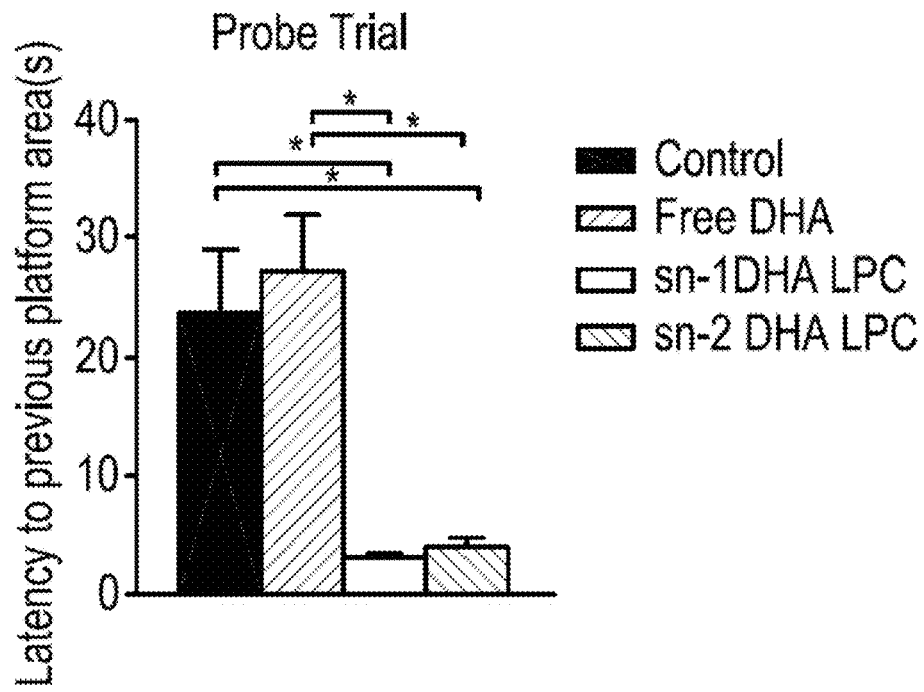
Figure 15C:
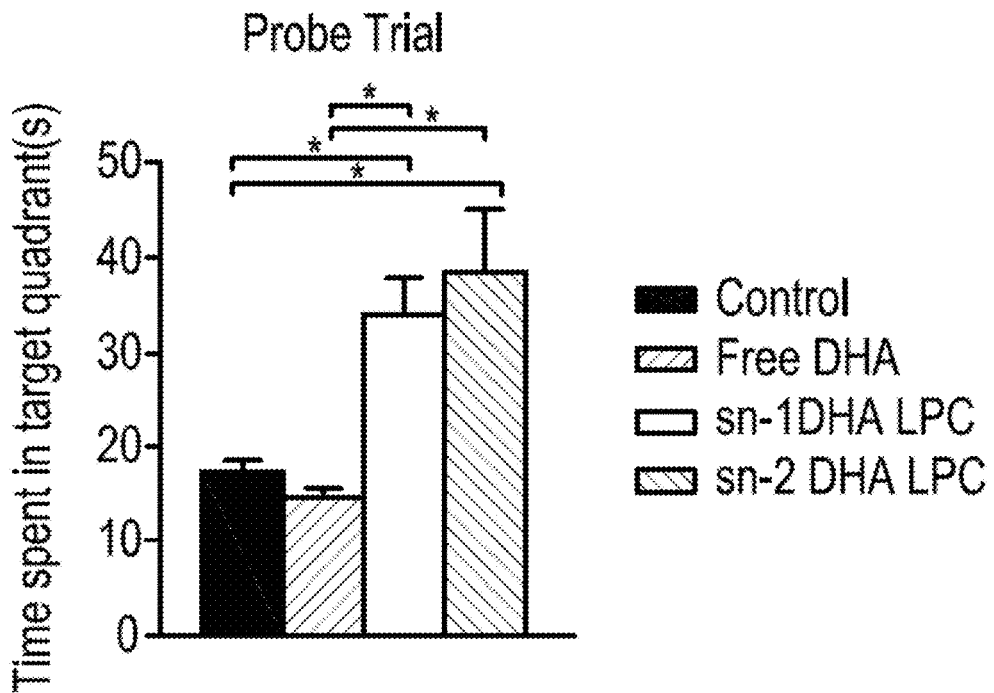

Although DHA has been reported to improve markers of cognition in DHA-deficient animals [19] or in the disease states [20], very few reports show a positive effects of dietary DHA on the cognitive functions of normal adult mice and rats. Even when the effects were demonstrated, the doses used were very high, in the range of 0.6 g to 2.4 g/kg body weight [20-23], relative to what is practical in humans. Since we could more than double the brain DHA levels at very low amounts of LPC DHA (about 40 mg/kg body weight), we assessed whether LPC-DHA also modulated spatial learning and memory, as determined by the Morris water maze test. In the acquisition phase, all groups learned the location of the platform with no significant group differences (FIG. 15A). Notably, however in the probe trial (FIGS. 15B-15D), mice treated with either sn-1 DHA LPC or sn-2 DHA LPC located the previous platform area with a shorter latency time and spent longer time in the target quadrant compared to free DHA-treated or control mice (two-way ANOVA followed by Tukey's post hoc comparisons). For example, both sn-1 and sn-2 DHA LPC treated mice found the previous platform area 7 times faster than the control and free DHA groups, and spent twice as long in the target quadrant.

Figure 15D:
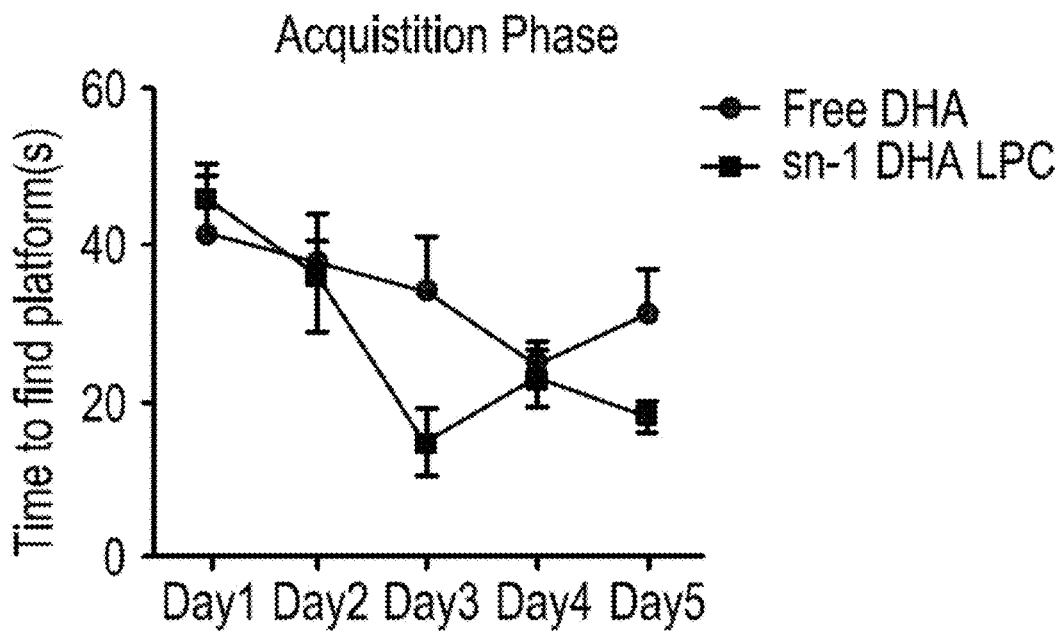
Figure 15E:
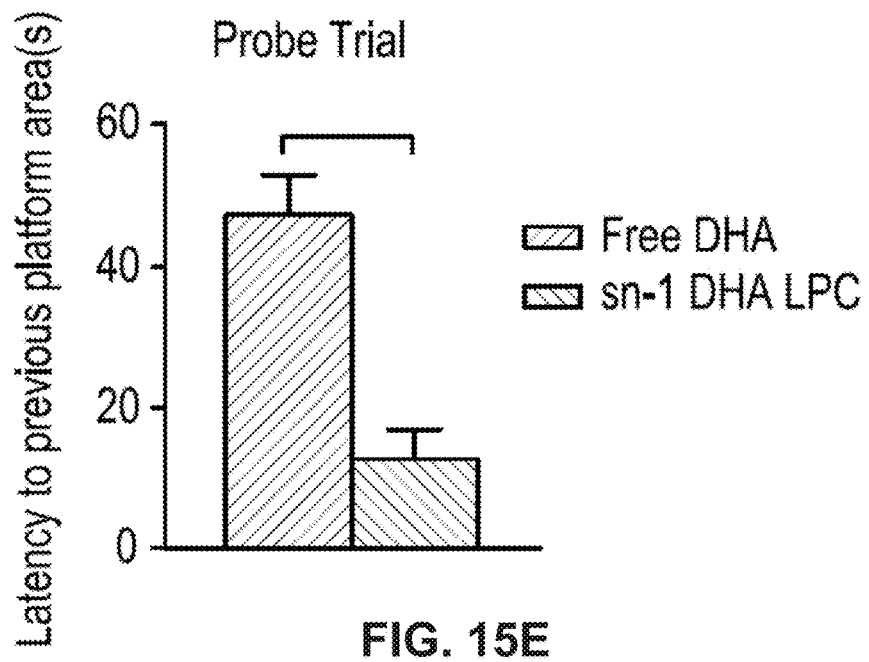
Figure 15F:
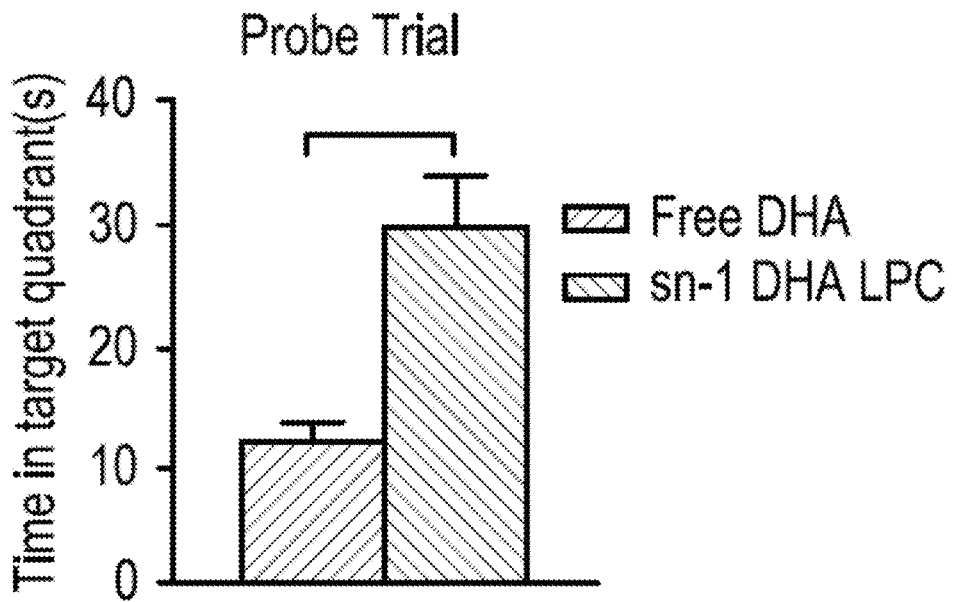
Figure 16A:
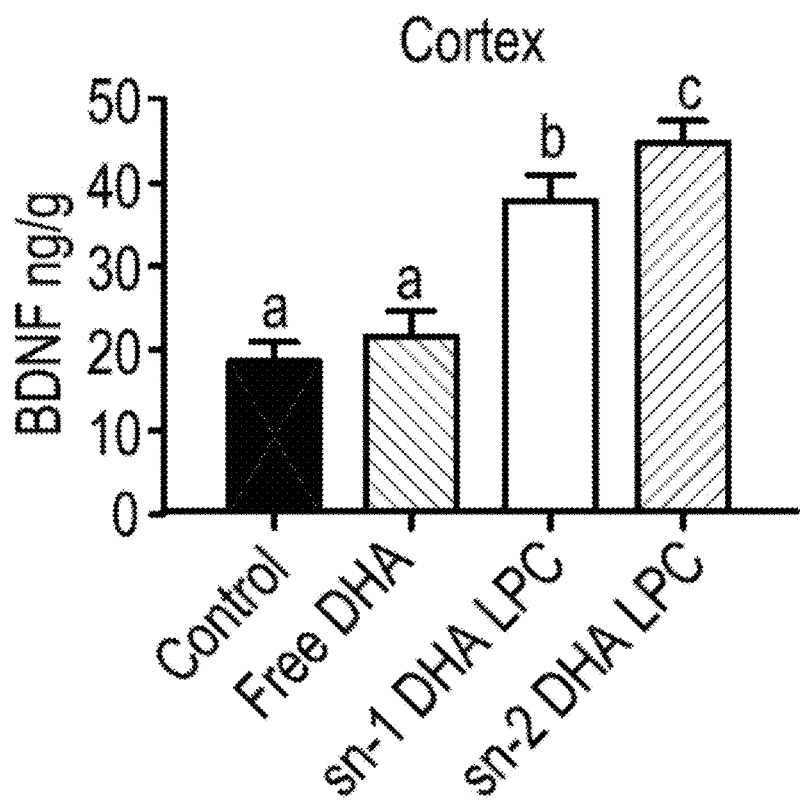
FIGS. 16A-16E show graphs that can demonstrate that BDNF levels in the brain regions of mice treated with various molecular carriers of dietary DHA. Values shown are mean±SD (n=6). Bars with non-identical letters are significant from each other by one way ANOVA, and post-hoc Tukey test.
Figure 16B:
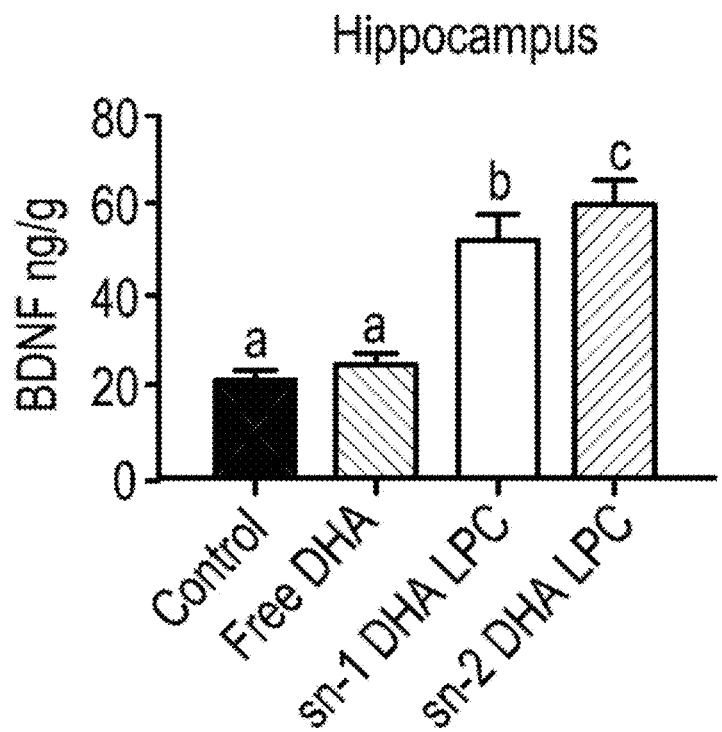
Figure 16C:
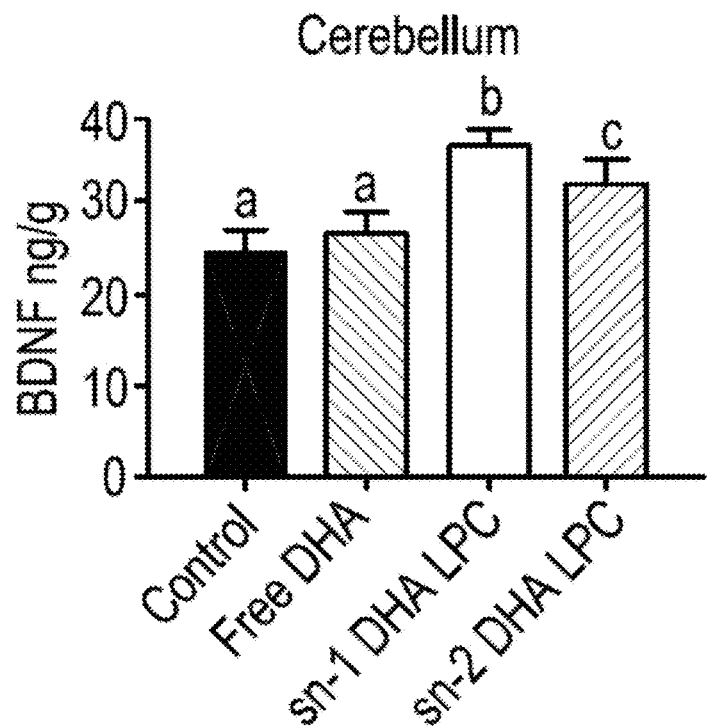
Figure 16D:
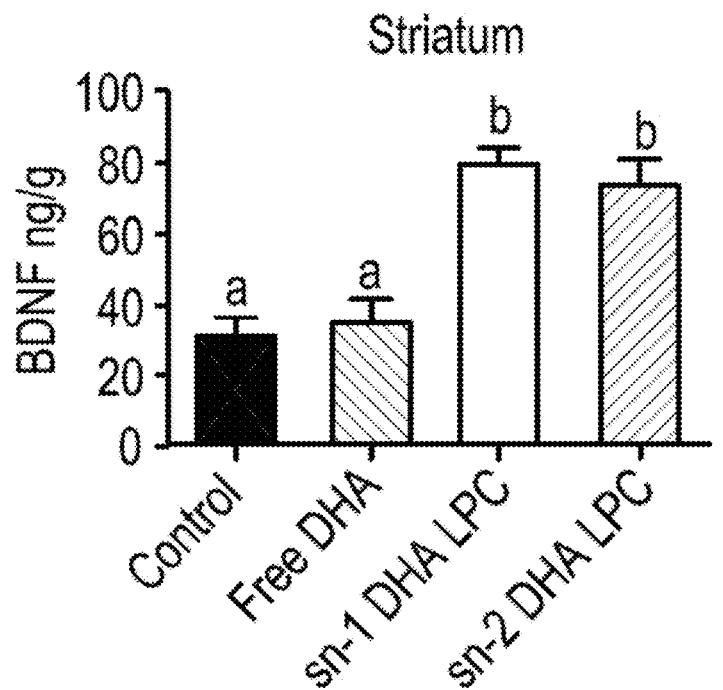
Figure 16E:
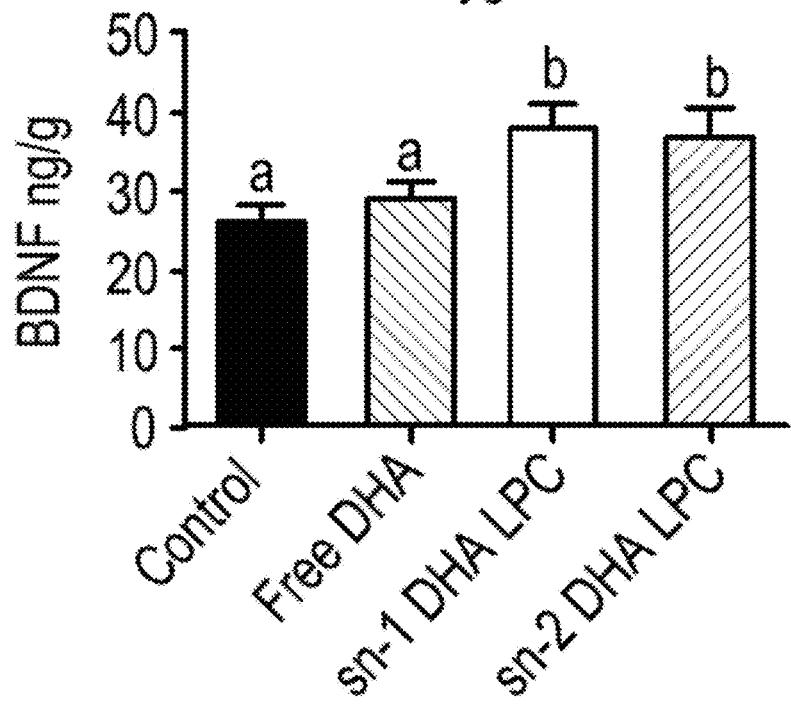

To account for cohort effects and for validation, a second study in a smaller cohort of mice was conducted comparing only the free-DHA treated group with sn-1 DHA LPC treated group (FIGS. 15D-15F). Since no difference was observed between vehicle control and free DHA groups in the above study, we did not include the vehicle control in the second study. Similarly, since there was no significant difference between the two isomers of LPC-DHA, we used only sn-1 DHA LPC. Although the data were more varied in the free-DHA group in this study, they were still consistent with the first study. In the acquisition phase, sn-1 DHA LPC mice learned the location of the platform faster by Day 5 (Day 1 vs days 2, 3, 4, 5 and day 2 vs 5, two-way ANOVA followed by Tukey's post hoc comparisons). However, the only significant difference for Free DHA mice was for day 1 vs 4 by two-way ANOVA followed by Fisher's LSD test i.e. no multi-group comparisons. As for the first treatment study, in the probe trial sn-1 DHA LPC mice located the previous platform area with a lower latency time (free DHA—47.1 seconds, sn-1 DHA LPC—12.7 seconds) and spent longer time in the target quadrant compared to free DHA (free DHA—12 seconds, sn-1 DHA LPC—29.9 seconds).

In both MWM tests there were no group differences in average swim speed or total distance swam in the probe trial, and open field test showed that there was no significant change from the control mice in any of the treatment groups (not shown). Therefore, the beneficial effects of LPC DHA on memory were not related to general changes in locomotion.

Effect of DHA on Brain Derived Neurotrophic Factor (BDNF) Levels.

BDNF plays an important role in learning and memory, and is a potential downstream target of DHA [24-26]. Therefore, we determined BDNF concentration in the brain regions by ELISA to complement our MWM data. As shown in FIGS. 16A-16E, while there was no change in BDNF content in any region of the brain after free DHA treatment, its levels were significantly increased by either sn-1 DHA or sn-2 DHA LPC. These results suggest that one of the mechanisms for the augmented memory in the mice treated with LPC-DHA is the increase in the BDNF levels.

Discussion

Although it is well accepted that low brain DHA levels are associated with impaired brain function and memory, as well as several neurological disorders, attempts to increase DHA levels and improve brain function through the diet have been largely unsuccessful, especially in adult animals and humans [27-29]. Without being bound by theory, this failure can be due to the presence of an intestinal barrier, which in conjunction with the blood brain barrier, prevents the DHA from the currently used supplements to enrich the brain. The proposed intestinal barrier is essentially the pancreatic enzymes, which release DHA from the dietary supplements in the form of free (unesterified) acid, which is then incorporated predominantly into chylomicron TAG (FIG. 10), whereas the blood brain barrier requires the DHA to be in lysophospholipid form for efficient enrichment of the brain [13-16]. In this study, we tested the hypothesis that if we can increase the absorption of DHA in the form of phospholipid, it is more likely to enrich the brain DHA and improve brain function. For this purpose, we compared dietary free DHA which is a surrogate for TAG-DHA (ex; fish oil, algal oil), as well as for the natural phospholipid-DHA (ex: krill oil), and which is absorbed as TAG, with dietary LPC-DHA, which is absorbed as PC [17], with respect to the enrichment of brain DHA.

The results presented here show that the brain DHA levels can be increased by >2-fold in the normal adult mice by feeding either sn-1 DHA LPC or sn-2 DHA LPC, whereas treatment with an equal amount of free DHA did not appreciably increase the brain DHA levels. Although previous studies suggested that the sn-2 DHA LPC can be preferred over the sn-1 isomer for uptake by the brain [14-15] we did not find significant differences between the two isomers when administered orally. Furthermore, the increase in brain DHA by the two LPC isomers resulted in similar increases in BDNF levels, and a striking but similar improvement in spatial memory, as measured by Morris water maze test. One possible explanation for this is that the sn-2 DHA LPC is rapidly isomerized to the sn-1 isomer, and therefore the differences between the isomers is abolished. However, our recent studies show that unlike sn-2 16:0 LPC, the isomerization of sn-2 22:6 LPC is much slower even at physiological pH and temperature (Sugasini and Subbaiah, unpublished results). Therefore, the lack of differential uptake is not due to the isomerization of the sn-2 DHA LPC.

It should also be pointed out that regardless of the LPC isomer used, the majority of the brain DHA was present in PE rather than in PC (FIGS. 20-21), suggesting that the DHA is released from LPC after its uptake, and reincorporated into membrane lipids of the brain.

The differential incorporation of free DHA and LPC DHA into the brain is not due to a difference in the amounts absorbed [17], but apparently due to dissimilar metabolic fates after absorption. Thus the free DHA, which is absorbed predominantly as TAG in the chylomicrons, was incorporated significantly into adipose tissue and the heart, but did not accumulate in the brain. On the other hand, LPC DHA, which is absorbed in phospholipid form to a greater extent [17] increased brain DHA levels, but had no effect on the adipose tissue DHA. In the liver, only the sn-2 DHA LPC increased the DHA concentration, whereas in the heart, all three preparations increased the DHA. It is known that chylomicrons, which have a very short half-life in the circulation (less that about 30 min), pass through the heart, adipose tissue and skeletal muscle before reaching the liver as remnants, and it is therefore likely that DHA from the absorbed TAG is largely picked up by these tissues. In fact previous studies showed that there is a preferential channeling of fatty acids derived from chylomicron TAG into adipose tissue [30]. In contrast, the DHA incorporated into phospholipids remains in the circulation much longer, because the chylomicron phospholipids are rapidly transferred to the HDL [31-32], which have a longer half-life of 12-24 h [33]. In addition, a significant fraction of dietary LPC-DHA is incorporated directly into intestinal HDL, mainly as phospholipids [17]. HDL phospholipids are the preferred substrates for three different enzymes in the plasma, namely lecithin-cholesterol acyltransferase [34], hepatic lipase [35], and endothelial lipase [36], all of which can generate LPC-DHA, the preferred carrier of DHA into brain [13-15].

The nature of the molecular carrier of DHA into the brain has been a matter of contention. Although it has been reported [13-15] that LPC-DHA is the preferred carrier of DHA through the blood brain barrier, the recent kinetic studies of Chen et al. [37] concluded that free DHA is the major source of brain DHA, and that LPC DHA is only a minor contributor. The latter authors further suggested that there is no net increase in the DHA content of adult brain from either free DHA or LPC DHA of plasma. However, our results clearly show a net increase in brain DHA by dietary LPC DHA in the adult mice. Furthermore, this increase is accompanied by a marked increase in spatial learning and memory. Thus, a 7-fold decrease in the latency to previous platform area, and 2-fold increase in the time spent in the target quadrant by the LPC DHA treatment was observed, compared to the control or free DHA treated animals.

One possible reason for the improved brain function is the increased levels of BDNF, which is known to play a critical role in learning and memory [38]. We found a significant increase in the BDNF levels after LPC-DHA treatment but not after free DHA treatment, thus showing a positive correlation of biochemical measurements with physiologic changes. The exact mechanism by which increases in brain DHA through LPC DHA leads to increase in BDNF levels is not clear. It is unlikely to be a direct effect of intact LPC DHA, since most of the brain DHA was present in PC and PE and only a small percentage was in LPC (FIGS. 20-21). It is more likely that free DHA released from membrane phospholipids not only acts as a precursor for various bioactive docosanoids [39], but also modulates BDNF transcription. It has been shown that DHA increases BDNF synthesis through activation of CREB (cAMP response element binding protein) phosphorylation [25-26]. DHA is also proposed to increase the transcription of BDNF by inhibiting hypermethylation of the promoter region of BDNF gene, which represses BDNF transcription [25]. Another possible mechanism is that since BDNF levels are negatively correlated with oxidative stress [40], and since DHA is known to induce anti-oxidant enzymes [41], the BDNF increase is a consequence of the induction of anti-oxidant enzymes which decrease the oxidative stress. A collateral benefit of delivering DHA to the brain in the form of LPC is that for each molecule of DHA entering the brain, a molecule of choline, an essential component of acetylcholine and of membrane lipids, is also delivered through the specific high affinity Mfsd2a transporter [16]. It is also possible that the free choline released from LPC hydrolysis contributes to the increase in BDNF, since previous studies showed that choline up-regulates BDNF, and down regulates its receptor TrkB (tropomyosin receptor kinase B), in cultured rat cortical cells [42]. An alternative explanation for the higher BDNF levels is that the DHA enrichment results in increased intracellular storage of BDNF, due to its decreased release. Although we cannot rule out this possibility at present, the improvement in memory by LPC-DHA suggests an increase in functionally active BDNF.

A previous study, in which female rats were fed DHA-enriched egg LPC of unknown composition, showed that the pups derived from these animals had increased DHA levels in some brain regions, and exhibited improved operant learning ability [43], indicating increased passage of DHA through the placenta. However, the brain DHA levels of the mothers were not measured in this study. The present studies demonstrated, for the first time, the feasibility of increasing the net concentration of DHA in the adult brain through diet. These results therefore have the potential to provide cognitive benefits for adult mammals due to the increases in brain DHA and BDNF. The observations of this Example can support a nutraceutical approach for the prevention and/or treatment of neurological diseases such as Alzheimer's, Parkinson's, traumatic brain injury, and depression, all of which can be benefited by DHA enrichment of the brain.

REFERENCES FOR EXAMPLE 2

1. Cunnane, S. C., Chouinard-Watkins, R., Castellano, C. A. & Barberger-Gateau, P. Docosahexaenoic acid homeostasis, brain aging and Alzheimer's disease: Can we reconcile the evidence? *Prostaglandins Leukot. Essent. Fatty Acids* 88, 61-70 (2013).
2. Sethom, M. M. et al. Polyunsaturated fatty acids deficits are associated with psychotic state and negative symptoms in patients with schizophrenia. *Prostaglandins, Leukotrienes and Essential Fatty Acids* 83, 131-136 (2010).
3. Bazan, N. G., Molina, M. F. & Gordon, W. C. Docosahexaenoic acid signalolipidomics in nutrition: significance in aging, neuroinflammation, macular degeneration, Alzheimer's, and other neurodegenerative diseases. *Annu. Rev. Nutr.* 31, 321-351 (2011).
4. Grosso, G. et al. Dietary n-3 PUFA, fish consumption and depression: A systematic review and meta-analysis of observational studies. *J Affect. Disord.* 205, 269-281 (2016).
5. McNamara, R. K. et al. Selective deficits in erythrocyte docosahexaenoic acid composition in adult patients with bipolar disorder and major depressive disorder. *J. Affect. Disord.* 126, 303-311 (2010).
6. DeMar, J. C. Jr., Ma, K., Chang, L., Bell, J. M. & Rapoport, S. I. Alpha linolenic acid does not contribute appreciably to docosahexaenoic acid within brain phospholipids of adult rats fed a diet enriched in docosahexaenoic acid. *J. Neurochem.* 94, 1063-1076 (2005).
7. Smink, W., Gerrits, W. J. J., Gloaguen, M., Ruiter, A. & van Baal, J. Linoleic and α-linolenic acid as precursor and inhibitor for the synthesis of long-chain polyunsaturated fatty acids in liver and brain of growing pigs. *Animal* 6, 262-270 (2012).
8. Tou, J. C., Altman, S. N., Gigliotti, J. C., Benedito, V. A. & Cordonier, E. L. Different sources of omega-3 polyunsaturated fatty acids affects apparent digestibility, tissue deposition, and tissue oxidative stability in growing female rats. *Lipids in Health and Disease* 10, 179 (2011).
9. Lin, Y. H., Shah, S. & Salem, J. Altered essential fatty acid metabolism and composition in rat liver, plasma, heart and brain after microalgal DHA addition to the diet. *The Journal of Nutritional Biochemistry* 22, 758-765 (2011).
10. Gazquez, A., Hernandez-Albaladejo, I. & Larque, E. Docosahexaenoic acid supplementation during pregnancy as phospholipids did not improve the incorporation of this fatty acid into rat fetal brain compared with the triglyceride form. *Nutrition Research* 37, 78-86 (2017).
11. Saito, M., Ueno, M., Kubo, K. & Yamaguchi, M. Dose-Response Effect of Dietary Docosahexaenoic Acid on Fatty Acid Profiles of Serum and Tissue Lipids in Rats. *J. Agr. Food Chem.* 46, 184-193 (1998).
12. Rodrigues, P. O. et al. Influence of feeding graded levels of canned sardines on the inflammatory markers and tissue fatty acid composition of Wistar rats. *British Journal of Nutrition* 112, 309-319 (2014).
13. Lagarde, M. et al. Lysophosphatidylcholine as a preferred carrier form of docosahexaenoic acid to the brain. *J. Mol. Neurosci.* 16, 201-204 (2001).
14. Thies, F., Delachambre, M. C., Bentejac, M., Lagarde, M. & Lecerf, J. Unsaturated fatty acids esterified in 2-acyl-1-lysophosphatidylcholine bound to albumin are more efficiently taken up by the young rat brain than the unesterified form. *J. Neurochem.* 59, 1110-1116 (1992).
15. Thies, F., Pillon, C., Moliere, P., Lagarde, M. & Lecerf, J. Preferential incorporation of sn-2 lysoPC DHA over unesterified DHA in the young rat brain. *Amer. J. Physiol-Regul. Integr. C.* 36, R1273-R1279 (1994).
16. Nguyen, L. N. et al. Mfsd2a is a transporter for the essential omega-3 fatty acid docosahexaenoic acid. *Nature* 509, 503-506 (2014).
17. Subbaiah, P. V., Dammanahalli, K. J., Yang, P., Bi, J. & O'Donnell, J. M. Enhanced incorporation of dietary DHA into lymph phospholipids by altering its molecular carrier. *Biochim Biophys Acta* 1861, 723-729 (2016).
18. Calder, P. C. Omega-3 Fatty Acids and Inflammatory Processes. *Nutrients* 2, 355-374 (2010).
19. Hiratsuka, S., Ishihara, K., Kitagawa, T., Wada, S. & Yokogoshi, H. Effect of Dietary Docosahexaenoic Acid Connecting Phospholipids on the Lipid Peroxidation of the Brain in Mice. *J. Nutr. Sci. Vitaminol. (Tokyo).* 54, 501-506 (2008).
20. Arsenault, D., Julien, C., Tremblay, C. & Calon, F. DHA Improves Cognition and Prevents Dysfunction of Entorhinal Cortex Neurons in 3×Tg-AD Mice. *PLoS ONE* 6, e17397 (2011).
21. Perez, S. E. et al. DHA diet reduces AD pathology in young APPswe/PS1delta E9 transgenic mice: Possible Gender Effects. *J Neurosci Res* 88, 1026-1040 (2010).

22. Lim, S. Y. & Suzuki, H. Changes in Maze Behavior of Mice Occur after Sufficient Accumulation of Docosahexaenoic Acid in Brain. *The Journal of Nutrition* 131, 319-324 (2001).
23. Petursdottir, A. L., Farr, S. A., Morley, J. E., Banks, W. A. & Skuladottir, G. V. Effect of Dietary n-3 Polyunsaturated Fatty Acids on Brain Lipid Fatty Acid Composition, Learning Ability, and Memory of Senescence-Accelerated Mouse. *The Journals of Gerontology Series A: Biological Sciences and Medical Sciences* 63, 1153-1160 (2008).
24. Wu, A., Ying, Z. & Gomez-Pinilla, F. The Salutary Effects of DHA Dietary Supplementation on Cognition, Neuroplasticity, and Membrane Homeostasis after Brain Trauma. *J Neurotrauma* 28, 2113-2122 (2011).
25. Tyagi, E., Zhuang, Y., Agrawal, R., Ying, Z. & Gomez-Pinilla, F. Interactive actions of Bdnf methylation and cell metabolism for building neural resilience under the influence of diet. *Neurobiol. Dis.* 73, 307-318 (2015).
26. Rao, J. S. et al. n-3 Polyunsaturated fatty acid deprivation in rats decreases frontal cortex BDNF via a p38 MAPK-dependent mechanism. *Mol Psychiatry* 12, 36-46 (2006).
27. Arendash, G. W. et al. A diet high in omega-3 fatty acids does not improve or protect cognitive performance in Alzheimer's transgenic mice. *Neuroscience* 149, 286-302 (2007).
28. Quinn, J. F., Raman, R. & Thomas, R. G. Docosahexaenoic acid supplementation and cognitive decline in alzheimer disease: A randomized trial. *JAMA* 304, 1903-1911 (2010).
29. Freund-Levi, Y., Eriksdotter-Jonhagen, M. & Cederholm, T. Omega-3 fatty acid treatment in 174 patients with mild to moderate alzheimer disease: OmegAD study: a randomized double-blind trial. *Arch. Neurol.* 63, 1402-1408 (2006).
30. Bickerton, A. S. T. et al. Preferential Uptake of Dietary Fatty Acids in Adipose Tissue and Muscle in the Postprandial Period. *Diabetes* 56, 168 (2006).
31. Tall, A. R., Green, P. H. R., Glickman, R. M. & Riley, J. W. Metabolic Fate of Chylomicron Phospholipids and Apoproteins in the Rat. *J. Clin. Invest.* 64, 977-989 (1979).
32. Redgrave, T. G. & Small, D. M. Quantitation of the Transfer of Surface Phospholipid of Chylomicrons to the High Density Lipoprotein Fraction during the Catabolism of Chylomicrons in the Rat. *The Journal of Clinical Investigation* 64, 162-171 (1979).
33. Kuai, R., Li, D., Chen, Y. E., Moon, J. J. & Schwendeman, A. High-Density Lipoproteins: Nature's Multifunctional Nanoparticles. *ACS Nano* 10, 3015-3041 (2016).
34. Subbaiah, P. V., Sowa, J. M. & Davidson, M. H. Evidence for altered positional specificity of LCAT in vivo: studies with docosahexaenoic acid feeding in humans. *J. Lipid Res.* 45, 2245-2251 (2004).
35. Yang, P. & Subbaiah, P. V. Regulation of hepatic lipase activity by sphingomyelin in plasma lipoproteins. *Biochim Biophys Acta* 1851, 1327-1336 (2015).
36. Chen, S. & Subbaiah, P. V. Phospholipid and fatty acid specificity of endothelial lipase: Potential role of the enzyme in the delivery of docosahexaenoic acid (DHA) to tissues. *Biochim. Biophys. Acta* 1771, 1319-1328 (2007).
37. Chen, C. T. et al. Plasma non-esterified docosahexaenoic acid is the major pool supplying the brain. *Sci Rep* 5, 15791 (2015).
38. Bekinschtein, P., Cammarota, M. & Medina, J. H. BDNF and memory processing. *Neuropharmacology* 76, Part C, 677-683 (2014).
39. Kuda, O. Bioactive metabolites of docosahexaenoic acid. *Biochimie* 136, 12-20 (2017).
40. Jain, S., Banerjee, B. D., Ahmed, R. S., Arora, V. K. & Mediratta, P. K. Possible Role of Oxidative Stress and Brain Derived Neurotrophic Factor in Triazophos Induced Cognitive Impairment in Rats. *Neurochemical Research* 38, 2136-2147 (2013).
41. Hashimoto, M., Hossain, S., Al Mamun, A., Matsuzaki, K. & Arai, H. Docosahexaenoic acid: one molecule diverse functions. *Crit. Rev. Biotechnol.* 1-19 (2016).
42. Johansson, J., Formaggio, E., Fumagalli, G. & Chiamulera, C. Choline up-regulates BDNF and down-regulates TrkB neurotrophin receptor in rat cortical cell culture. *NEUROREPORT* 20 (2009).
43. Valenzuela, A. et al. Supplementing female rats with DHA-lysophosphatidylcholine increases docosahexaenoic acid and acetylcholine in the brain and improves the memory and learning capabilities of the pups. *Grasas & Aceites* 61, 16-23 (2010).
44. Sarney, D., Fregapane, G. & Vulfson, E. Lipase-catalyzed synthesis of lysophospholipids in a continuous bioreactor. *J Am Oil Chem Soc* 71, 93-96 (1994).
45. Bligh, E. G. & Dyer, W. J. A rapid method of total lipid extraction and purification. *Can. J. Biochem. Physiol.* 37, 911-917 (1959).
46. Ivanova, P. T., Milne, S. B., Byrne, M. O., Xiang, Y. & Brown, H. A. Glycerophospholipid identification and quantitation by electrospray ionization mass spectrometry. *Methods Enzymol.* 432, 21-57 (2007).
47. Thomas, R. et al. Epidermal growth factor prevents APOE4 and amyloid-beta-induced cognitive and cerebrovascular deficits in female mice. *Acta Neuropathol. Commun.* 4, 111 (2016).

Example 3

Figure 22:
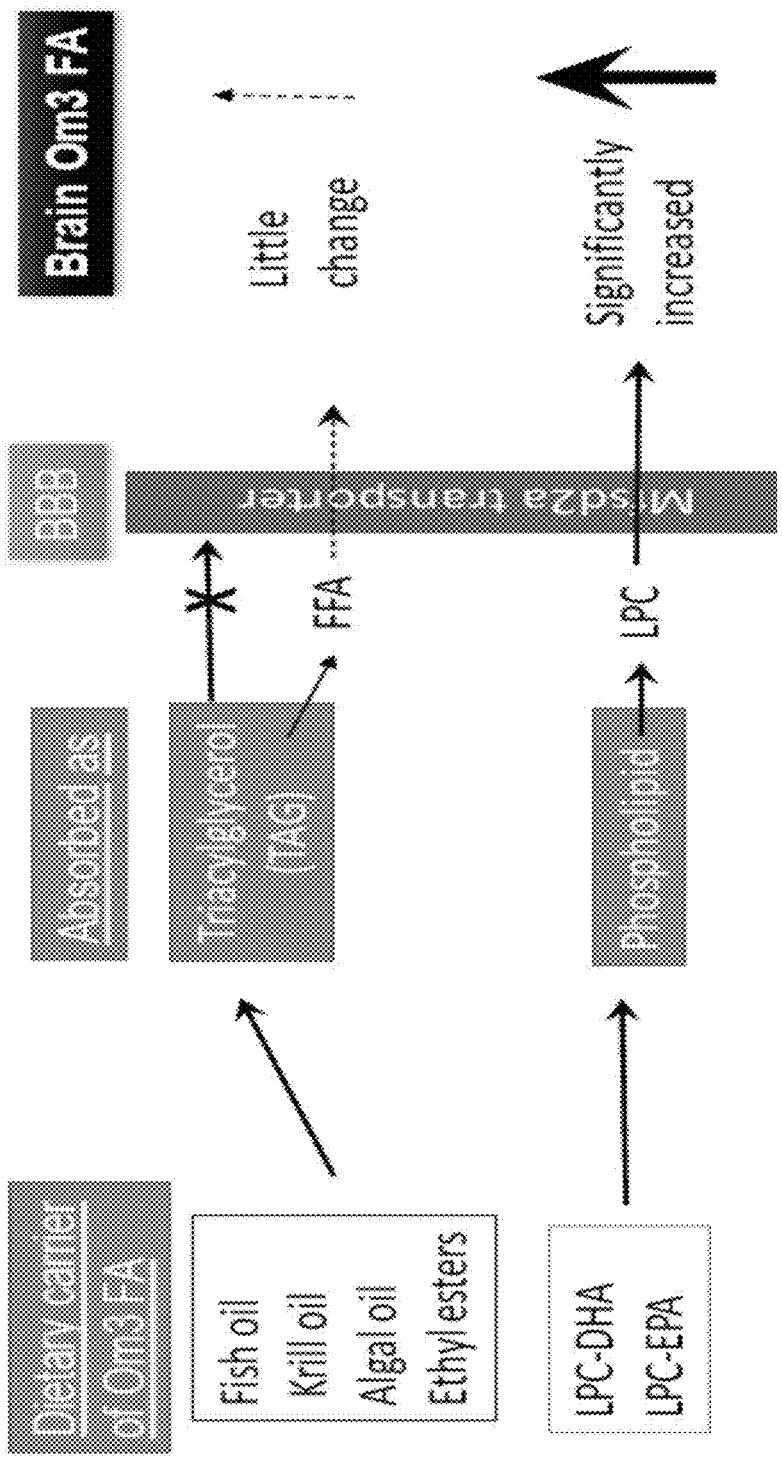
FIG. 22 shows a schematic that can show the absorption path for different DHA and EPA carriers and/or precursors. Whereas fish oil and other supplements are absorbed as TAG, LPC-EPA an dLPC-DHA are absorbed as phospholipids. TAG cannot cross the blood brain barrier, although some free Omega 3 fatty acids can be transported into the brain through diffusion. On the other hand, the phospholipid forms of DHA or EPA are transported efficiently through Mfsd2a transporter and increase the brain levels of at least DHA and/or EPA.

Major depressive disorder (MDD) affects 350 million people worldwide, with a lifetime prevalence of 5-15% in the Western countries. In addition to being the leading cause of suicides, MDD is a risk factor for cardiovascular, metabolic, and neuropsychiatric diseases, and imposes an enormous burden on the quality of life, productivity, and socioeconomic resources. The total economic burden of MDD in the US was about $210 billion in 2010, and is steadily increasing. Although there are numerous risk factors for depression, a common but under-appreciated mechanism for many risk factors is the chronic unresolved inflammation. Two major omega 3 fatty acids (Om3 FA) eicosapentaenoic acid (EPA), and docosahexaenoic acid (DHA) are anti-inflammatory, since they inhibit the production of pro-inflammatory eicosanoids and cytokines, regulate the function of membrane receptors and transporters, and generate several pro-resolving metabolites such as resolvins, protectins, and maresins. There is a negative correlation between the consumption of Om3 FA and the prevalence of depression among various populations. Therefore, increasing the brain Om3 FA levels through diet has great potential in the prevention and/or treatment of depressive disorders; however, studies in experimental animals as well as clinical trials in patients with depression employing dietary supplements of Om3FA have yielded varying results. Thus while some studies showed positive results with EPA, but not DHA, others showed positive effects with DHA alone or showed no effect. On balance, EPA appears to be more effective than DHA, but its levels in the brain are greater than 200-fold lower than DHA, and do not increase significantly by fish oil supplementation, even when the latter contains more EPA than DHA. The lack of EPA enrichment in brain can be due to its rapid oxidation and/or less efficient transport across the BBB. A specific transporter at the blood brain barrier (MFSD2a) requires the LPC form of Om3FA, and therefore fish oil and other currently available supplements do not enrich the brain Om3 FA since they are absorbed in the form of triacylglycerol (TAG) (FIG. 22).

Figure 23A:
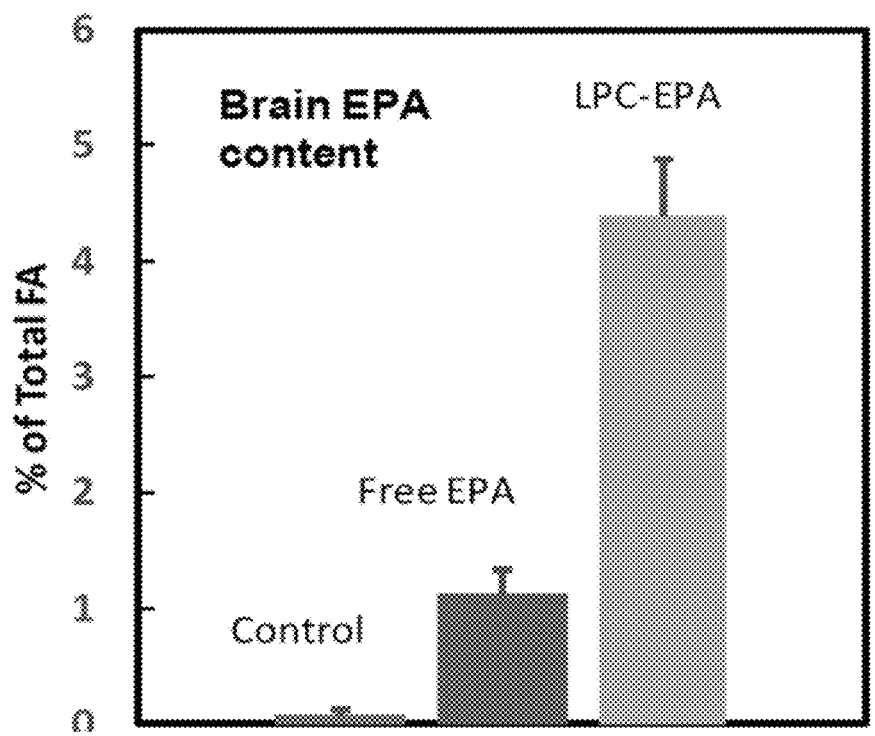
FIGS. 23A-23C show graphs that can demonstrate that oral LPC-EPA (1 mg/day for 15 days) can significantly increase both EPA and DHA in the brain, whereas free EPA increased only EPA to a small extent.
Figure 23B:
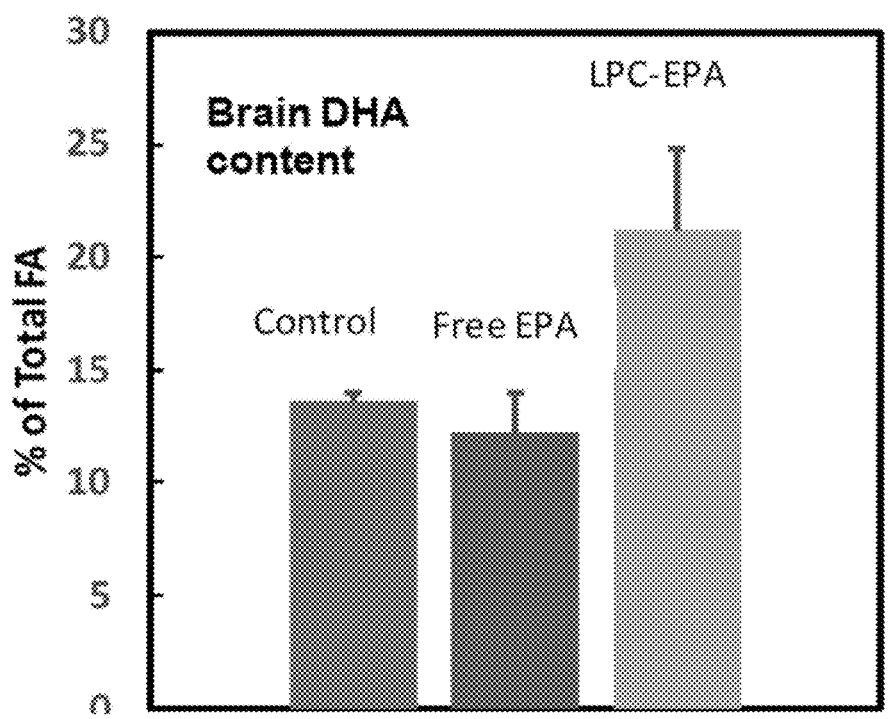
Figure 23C:
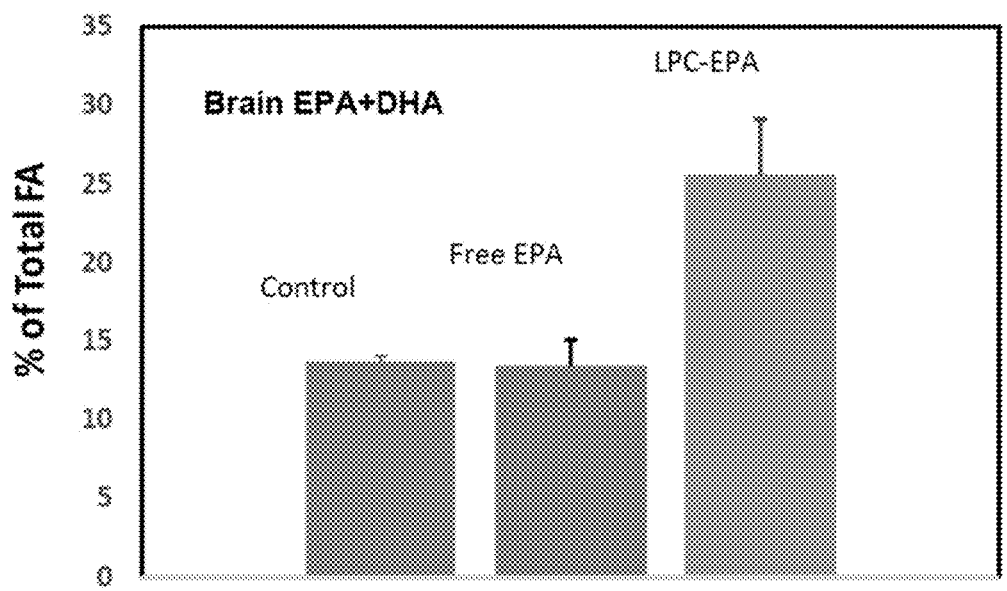

As previously described (see e.g. Examples 1 and 2), brain DHA can be increased by employing dietary LPC-DHA, which is absorbed in the phospholipid form and is transported efficiently through the BBB. This Example can demonstrate the use of this strategy to increase brain EPA by over 70-fold (see e.g. FIGS. 23A-23C).

Figure 24:
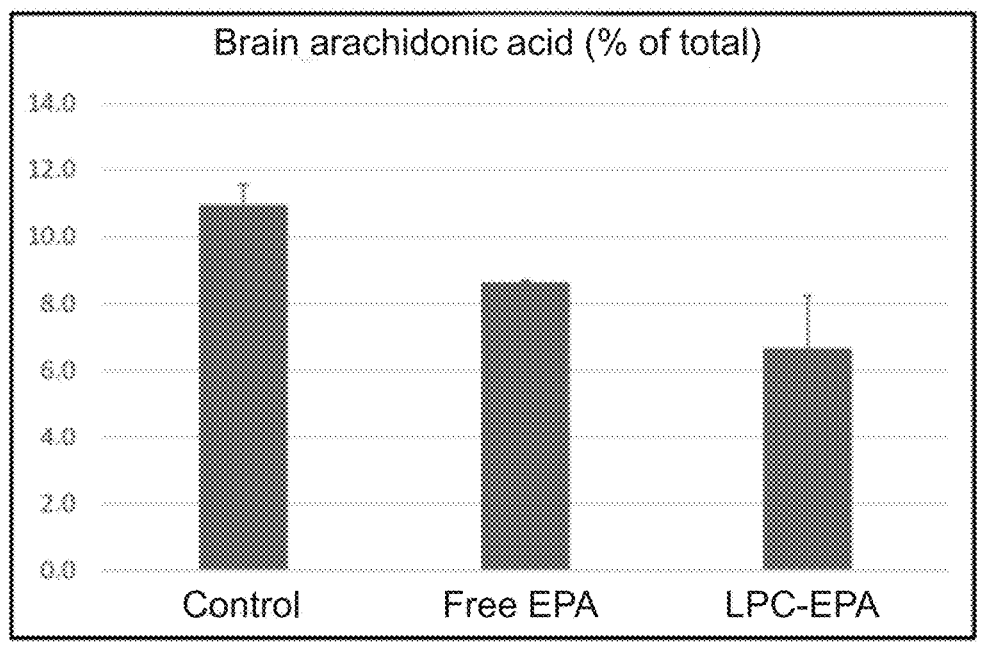
FIG. 24 shows a graph that can demonstrate the brain content of arachidonic acid, a pro-inflammatory fatty acid, decreases more by LPC-EPA (about a 40% decrease) then by free EPA (which produced only about a 12% decrease).

Mice were fed oral preparations of free EPA or LPC-EPA at about 1 mg/kg per day for 15 days. The compounds were dispersed in corn oil (80 µl) and fed daily by gavge. Results are shown in e.g. FIGS. 23A-34. Oral LPC-EPA increased brain DHA content by 60%, whereas free EPA had no effect on brain DHA, although it increased brain EPA to a small extent. The total amount of brain Omega 3 fatty acids FA (EPA+DPA+DHA) increased by about 90% after feeding LPC-EPA, but showed no change after feeding free EPA. See e.g. FIGS. 23A-23C. FIG. 24 shows a graph that can demonstrate the brain content of arachidonic acid, a pro-inflammatory fatty acid, decreases more by LPC-EPA (about a 40% decrease) than by free EPA (which produced only about a 12% decrease).

Figure 25:
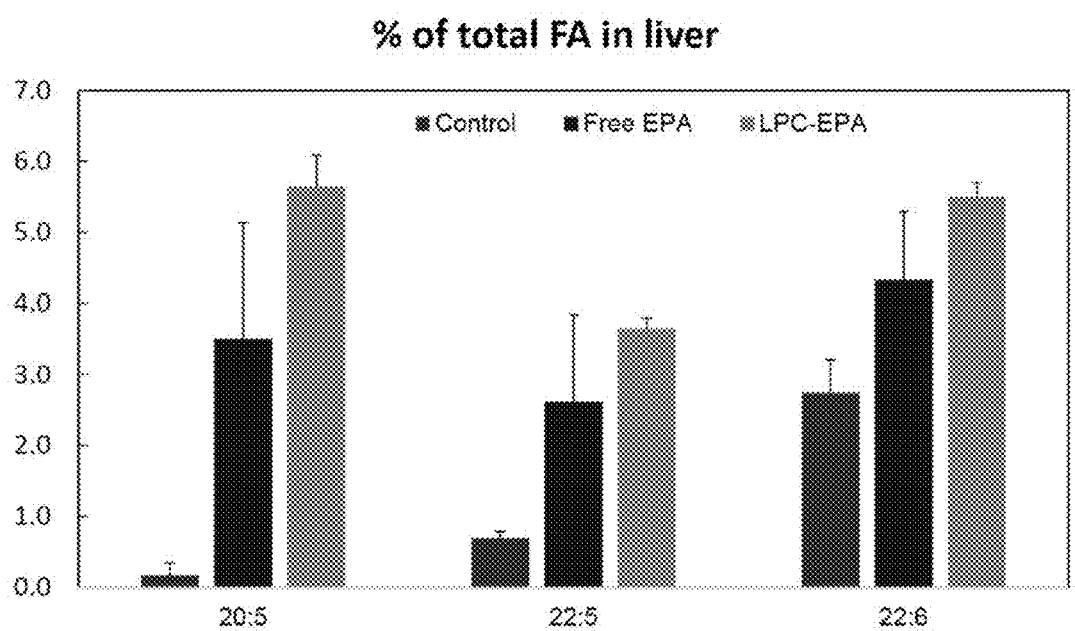
FIG. 25 shows a graph that can demonstrate that both free EPA and LPC-EPA increased all three n-3 fatty acids in the liver, although the increase was greater with LPC-EPA. Unlike the brain, the liver accumulated 22:5 (n-3) an intermediate in the conversion of EPA to DHA.

FIG. 25 shows a graph that can demonstrate that both free EPA and LPC-EPA increased all three n-3 fatty acids in the liver, although the increase was greater with LPC-EPA. Unlike the brain, the liver accumulated 22:5 (n-3) (DPA) an intermediate in the conversion of EPA to DHA.

Figure 26:
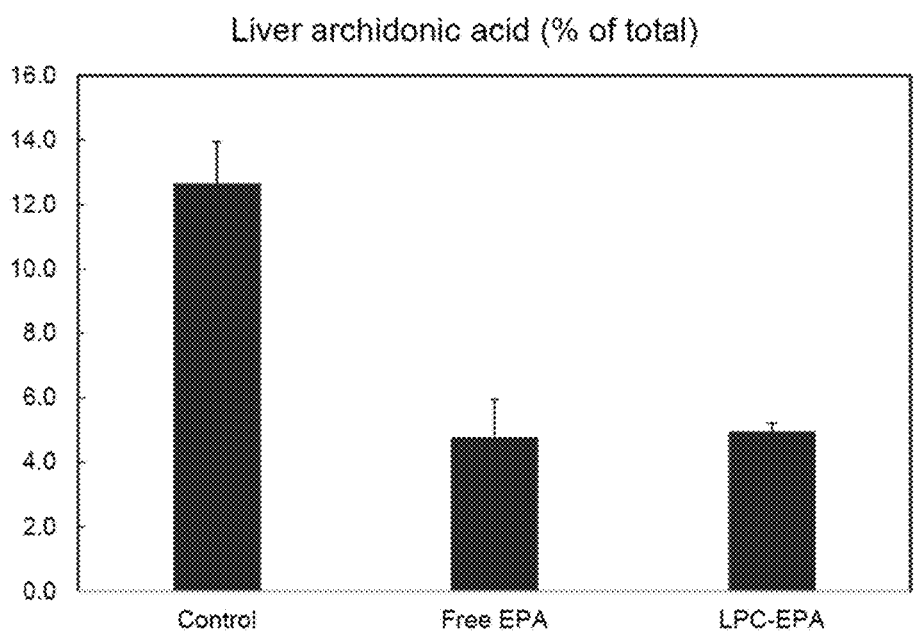
FIG. 26 shows a graph that can demonstrate that unlike in the brain, the decrease in liver arachidonic acid level was more severe and equal with the feeding of free EPA and LPC-EPA (about a 60% decrease).
Figure 27B:
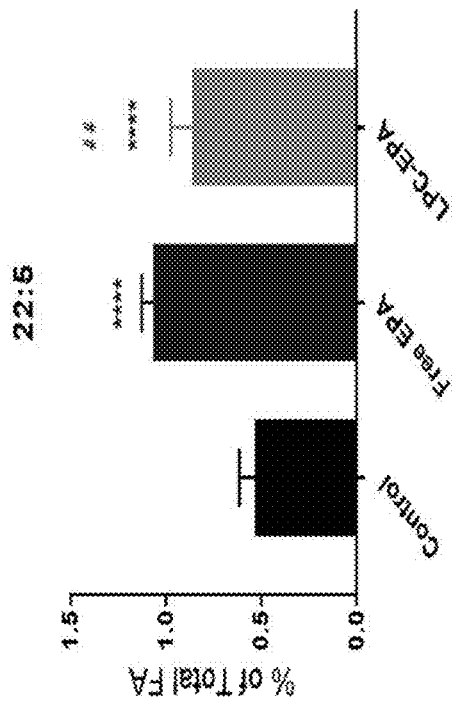
FIGS. 27A-27D show graphs that can demonstrate the omega 3 fatty acids in plasma after feeding free EPA or LPC-EPA at 1 mg EPA/day for 15 days. In plasma, free EPA increased the total omega 3 fatty acids more than LPC-EPA. In addition to EPA, DPA (22:5) and DHA (22:6) were increased by both preparations. * Different from control; # different from free EPA.
Figure 27D:
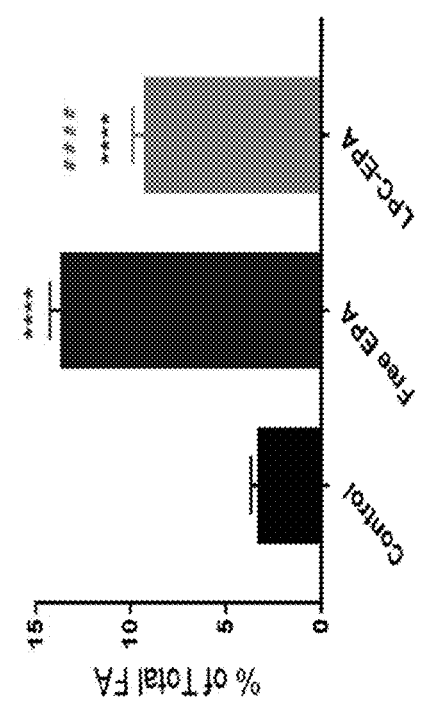
Figure 27A:
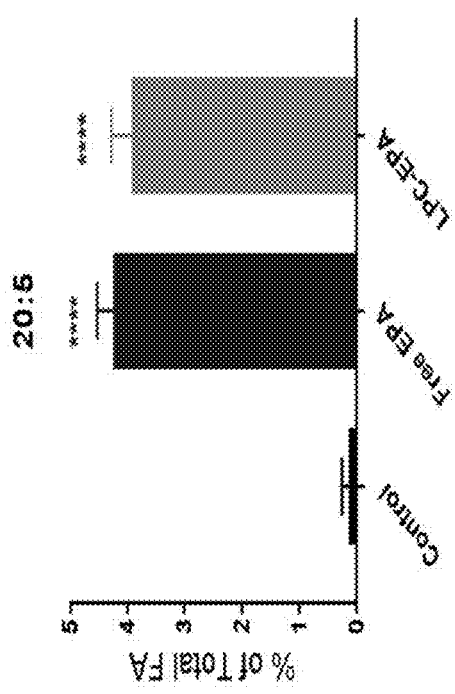
Figure 27C:
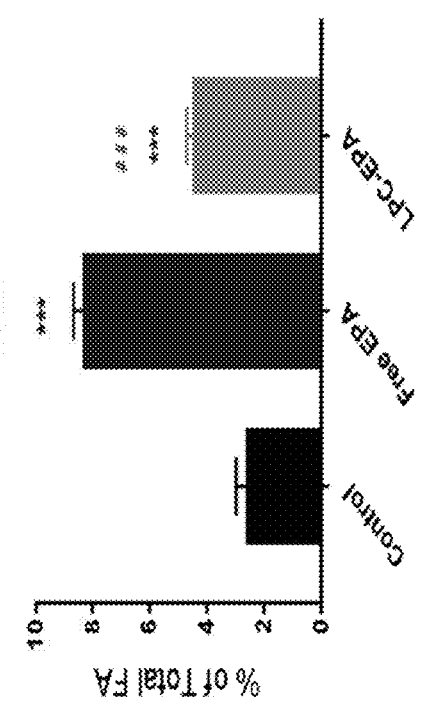
Figures 28A, 28B, 28C, 28D:
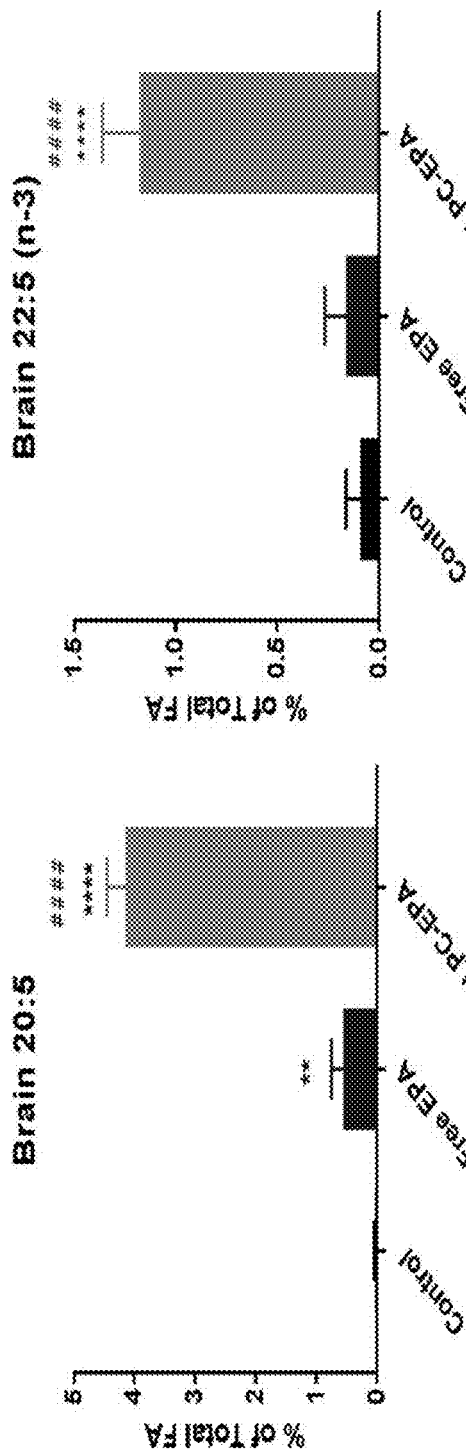
FIGS. 28A-28D show graphs that can demonstrate the omega 3 fatty acids in brain after feeding free EPA or LPC-EPA at 1 mg EPA/day for 15 days. The total omega 3 fatty acid content of the brain was increased by LPC-EPA, but not by free EPA. Most of the increase appeared to be due to an increase in the elongation products 22:5 and 22:6, rather than EPA itself. * Different from control; # different from free EPA.

FIG. 26 shows a graph that can demonstrate that unlike in the brain, the decrease in liver arachidonic acid level was more severe and equal with the feeding of free EPA and LPC-EPA (about a 60% decrease).

FIGS. 27A-27D shows graphs that can demonstrate the omega 3 fatty acids in plasma after feeding free EPA or LPC-EPA at 1 mg EPA/day for 15 days. In plasma, free EPA increased the total omega 3 fatty acids more than LPC-EPA. In addition to EPA, DPA (22:5) and DHA (22:6) were increased by both preparations. * Different from control; # different from free EPA.

FIGS. 28A-28D show graphs that can demonstrate the omega 3 fatty acids in brain after feeding free EPA or LPC-EPA at 1 mg EPA/day for 15 days. The total omega 3 fatty acid content of the brain was increased by LPC-EPA, but not by free EPA. Most of the increased appeared to be due to an increase in the elongation products 22:5 and 22:6, rather than EPA itself. * Different from control; # different from free EPA.

FIGS. 29A-29D shows graphs that can demonstrate the omega 3 fatty acids in liver after feeding free EPA or LPC-EPA at 1 mg EPA/day for 15 days. Both free EPA and LPC-EPA increased liver omega 3 fatty acids, although LPC-EPA was more efficient. In contrast to the brain, there was significant accumulation of EPA and DPA, in addition to DHA, suggesting that the conversion of EPA to DHA is more efficient in the brain, compared to the liver. These results are in contrast to the previous assumption that brain cannot efficiently convert EPA to DHA. * Different from control; # different from free EPA.

FIGS. 30A-30D show graphs that can demonstrate the omega 3 fatty acids in heart after feeding free EPA or LPC-EPA at 1 mg EPA/day for 15 days. In the heart, free EPA and LPC-EPA were equally efficient in enriching the total omega 3 fatty acids. The accumulation of EPA was greater than in other tissues, suggesting a lower conversion to DPA and DHA. * Different from control; # different from free EPA.

FIGS. 31A-31D show graphs that can demonstrate the omega 3 fatty acids in adipose tissue after feeding free EPA or LPC-EPA at 1 mg EPA/day for 15 days. The omega 3 fatty acid content of adipose tissue was enriched more with free EPA than with LPC-EPA. There was, however, no conversion of EPA into DPA or DHA in this tissue, since all the increase was due to EPA. * Different from control; # different from free EPA.

FIGS. 32A-32D show graphs that can demonstrate the omega 3 fatty acids in erythrocytes after feeding free EPA or LPC-EPA at 1 mg EPA/day for 15 days. Only free EPA increased the omega 3 fatty acids and no conversion to DPA or DHA was observed. * Different from control; # different from free EPA.

FIGS. 33A-34F show graphs that can demonstrate arachidonic acid (20:4) in various tissues after feeding free EPA or LPC-EPA at 1 mg EPA/day for 15 days. In all tissues, the concentration of arachidonic acid was decreased after feeding either free EPA or LPC-EPA. The decrease was similar with LPC-EPA and free EPA except in the brain where LPC-EPA decreased it more. * Different from control; # different from free EPA.

Figure 34:
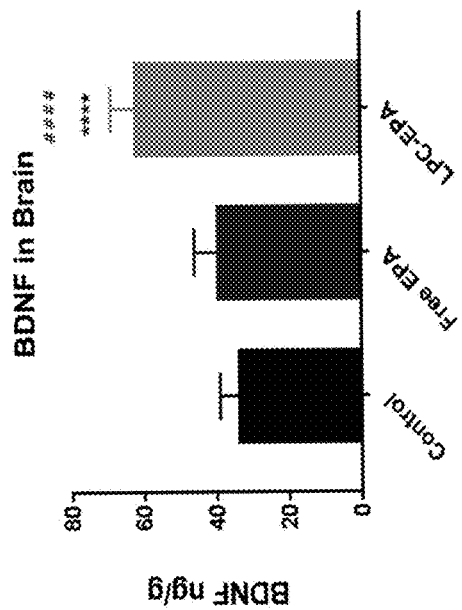
FIG. 34 shows a graph that can demonstrate BDNF levels in the brain after feeding free EPA or LPC-EPA at 1 mg EPA/day for 15 days. BDNF levels in the brain were observed to be increased by LPC-EPA but not by free EPA. * Different from control; # different from free EPA.
Figure 33E:
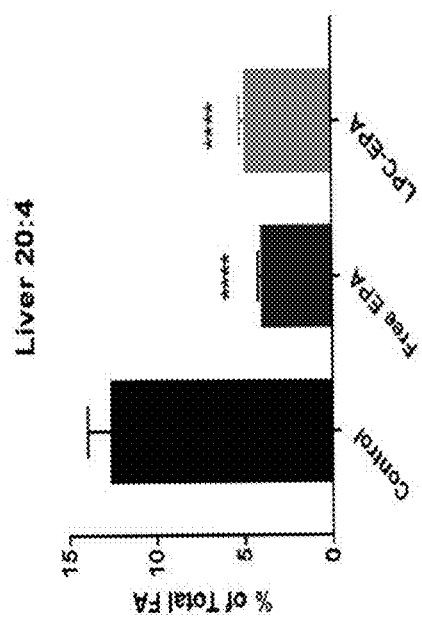
Figure 33F:
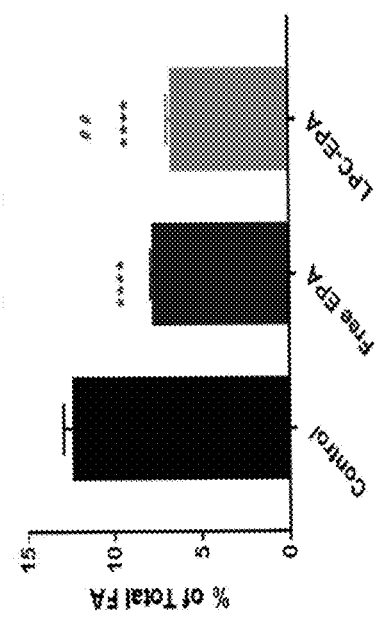
Figure 35D:
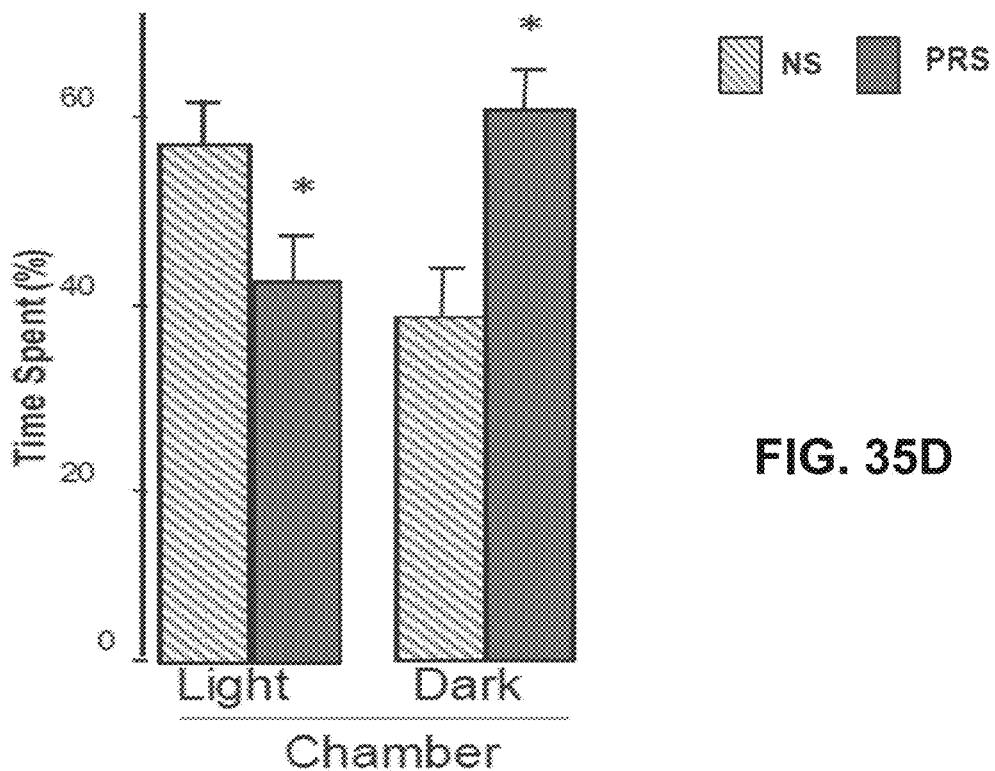
Figure 35E:
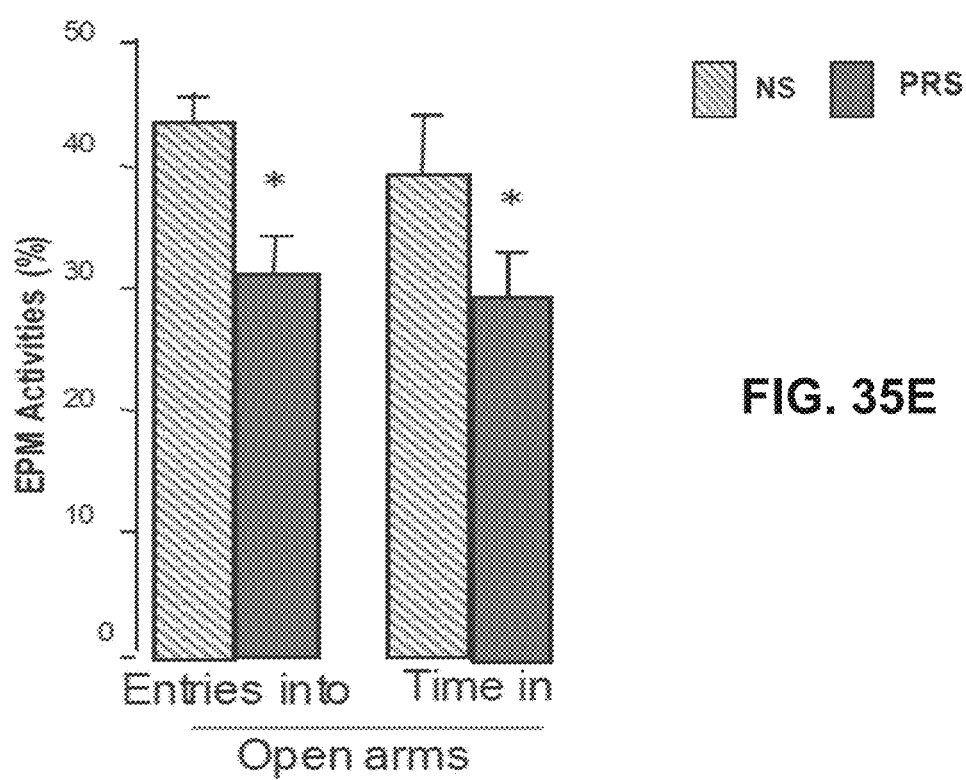

FIG. 34 shows a graph that can demonstrate BDNF levels in the brain after feeding free EPA or LPC-EPA at 1 mg EPA/day for 15 days. BDNF levels in the brain were observed to be increased by LPC-EPA but not by free EPA. * Different from control; # different from free EPA.

Figure 36:
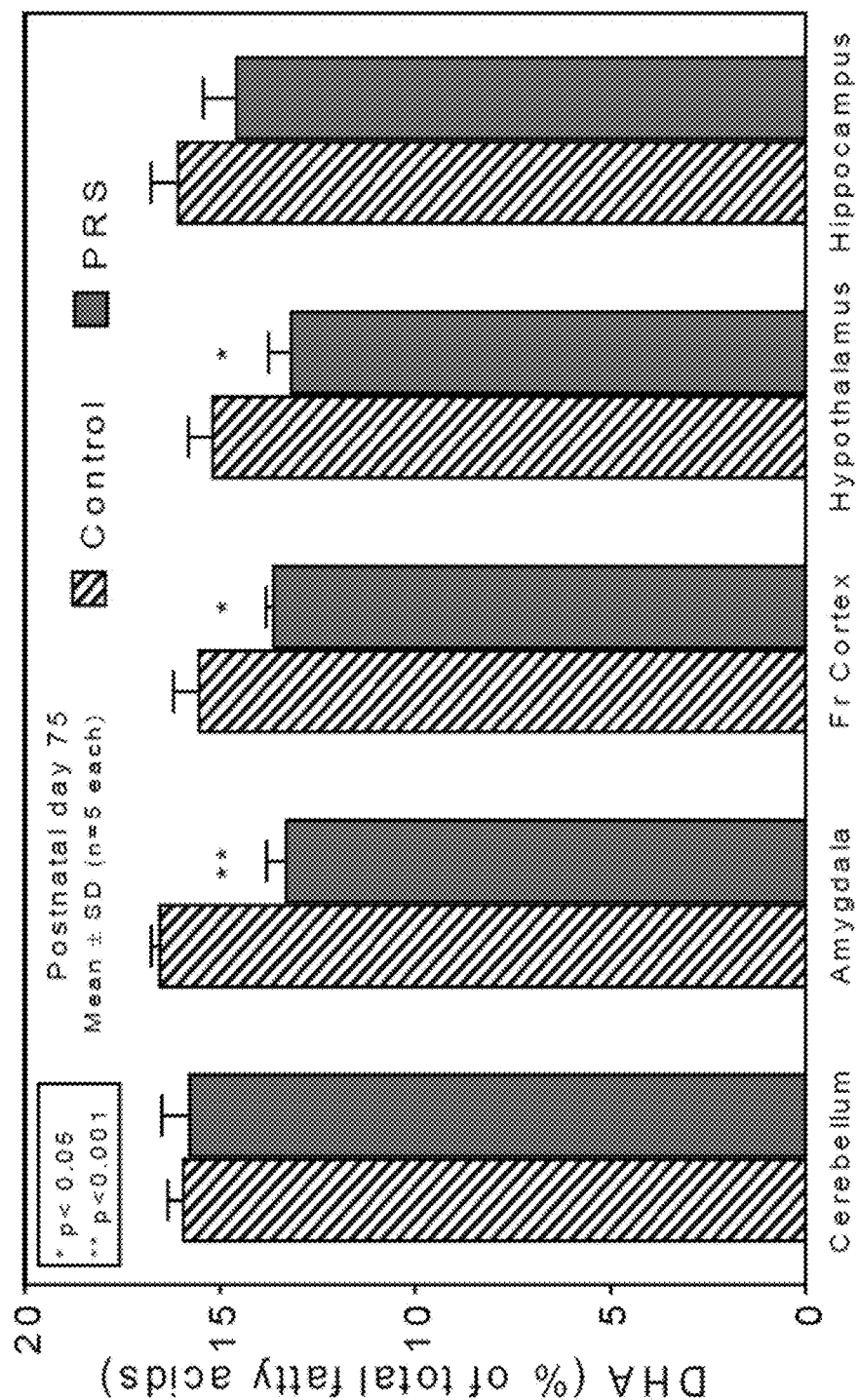
FIG. 36 shows a graph that can demonstrate DHA content of most regions of the brain can be significantly reduced in the offspring of dams subjected to pre-natal restraint stress (PRS).

As described herein, this strategy can be used to determine the efficacy the prevention and/or treatment of depression in a mouse model (pre-natal restraint stress, or PRS) previously established. (FIGS. 35A-35E). This mouse model of depression exhibits depression-like behavior, characterized by increased immobility in forced swim test and tail suspension test, reduced social interaction and anxiety (light/dark box, elevated plus maze) in adulthood, as compared to the non-stressed (NS) controls. It resembles the depression occurring in children and young adults whose mothers experienced stress during pregnancy. At the molecular level, the PRS mice in the model system show altered DNA methylation profiles characterized by overexpression of DNMT1 and disrupted chromatin structures including decreased acetyl histone 3 (acH3K14) due to increased Hdacs (Hdac1 and 2) at genes associated with synaptic plasticity and mental disorders, including Bdnf and Gad1. Additionally, as described herein, these mice were observed to have a significant loss of brain DHA levels in the adult offspring of dams subjected to PRS (FIG. 36), increasing their brain DHA and EPA in the womb and during lactation is a promising approach for the prevention of depression later in their life. It is of interest to note that the transporter responsible for the brain accretion of DHA (MFSD2a) is also important for the transport of DHA through the placenta.

PRS-mice can be generated according to an established prenatal stress paradigm. Pregnant mice (Swiss albino ND4, (from Harlan, Indianapolis) can be individually housed under a 12-hour light-dark cycle with access to food, and water ad libitum. Control dams (non-PRS) can be left undisturbed throughout gestation, whereas stressed dams will be subjected to repeated episodes of restraint stress, as described previously. Briefly, the stress procedure is composed of restraining the pregnant dam in a transparent tube (12×3 cm) under a bright light for 30 min, three times per day from the seventh day of pregnancy until delivery. Control dams (unstressed) can be fed normal chow throughout gestation and lactation. The stressed dams can be divided into four groups and fed the following diets during gestation and lactation periods: (1) control diet, supplemented AIN 93G; (2) LPC-EPA-supplemented AIN 93G; (3) LPC-DHA-supplemented AIN 93G; (4) Fish oil (or other source of omega or other fatty acids)-supplemented AIN 93G. Here, the LPC-EPA or LPC DHA can pass to the fetus through the placenta or newborn through the mother's milk.

Diets and Treatment:

Di-DHA PC, and Di-EPA PC can be synthesized chemically by an established procedure in our laboratory. This procedure involves binding glycerophosphorylcholine (GPC) to celite, followed by reaction with free DHA or free EPA in the presence of dicyclohexylcarbodiimide (DCC) and 4-dimethylaminopyridine (DMAP) for 24 h at 30° C. The PC synthesized is purified on a silicic acid column and then treated with snake venom PLA2 in presence of diethyl ether to generate the corresponding sn-1 acyl LPC. The sn-2 acyl LPC can also be produced from this PC by treating it with Mucor lipase (insread of snake venom phospholipase). The LPCs can then be purified by silic acid chromatography. Fish (Menhaden) oil can be purchased from Omega Protein Inc. (Houston, Tex.) and supplemented with synthetic TAG-DHA from NuChek (44 mg/g), to equalize the EPA and DHA levels. All diets can contain 150 IU of vitamin E/kg, and can be prepared by blending the supplements with normal chow (AIN 93G, which contains no EPA or DHA), pelleted, vacuum sealed in small portions (200 g) and stored at $-20°$ C. until use, to prevent any oxidation of the fatty acids. The LPC-Om3FA diets can contain either EPA or DHA at a concentration of 0.35 g/kg diet, whereas the fish oil diet can contain both EPA and DHA at 0.35 g each/kg (2.6 g oil/kg). Assuming a 25 g mouse consumes 3 g of diet/day, this can provide about 40 mg DHA or EPA/kg body weight/day in the form of LPC, or 40 mg each of EPA and DHA as TAG in the case of fish oil. This amount of LPC-Om3 FA was chosen, based other data presented herein (e.g. Example 2) in normal mice that showed significant increase in brain DHA. The DHA-enriched fish oil concentration is chosen to match the content of EPA and DHA, but in the form of TAG.

Stressed and unstressed dams can be fed ad libitum, the diets described above from Day 7 of gestation until the end of lactation period. Following the weaning period, the mothers can be sacrificed and their blood, livers and brain collected for fatty acid analyses. If the EPA and DHA levels are lower in the plasma and liver of stressed mothers, it can indicate that the decrease in the brain DHA of offspring is due to the decreased supply from the maternal blood. Otherwise, it can be assumed that the decrease is due to the effect of stress on the fetus.

After weaning, male and female offspring mice can be housed separately (five per cage). The offspring from both stressed and non-stressed mothers can be fed the normal chow until post-natal day (PND) 75.

The weaned offspring (10 females, 10 males per group) can be fed the control diet until the end of the study. The food can be changed daily, and consumption of the food determined by weighing the leftover food. Body weights will be recorded weekly. At PND75, behavioral tests can be carried out as described below. PND 75 can be used for these studies because the performance of the offspring was previously more reproducible than at earlier time points With that said, other time points can be used as well. After the completion of the behavioral tests, blood can be collected by cardiac puncture under anesthesia, and following cardiac perfusion to clear the blood from tissues, the liver can be harvested and flash frozen for lipid analysis. The brain regions can be dissected (including hippocampus, frontal cortex, cerebellum, hypothalamus, amygdala) and portions flash frozen and stored at $-80°$ C. until the lipid and Western blot and epigenetic analyses. Portions of each brain region will also be treated with RNAlater (Invitrogen) according to the manufacturer's instructions, and stored at $-80°$ C. for the analysis of gene expression.

Behavioral Tests:

The behavioral tests can be carried out as previously established (see e.g. Example 2).

1. Forced Swimming Test (FST) (depression): In the pre-test session, the mouse can be placed in a clear container (20 cm diameter, 50-cm height) that contains water ($25\pm1°$ C.) to a depth of 25 cm, and forced to swim for 5 minutes. The water can be replaced for each mouse. In the test-session, the mouse will be placed back into the container for 5 minutes. Immobility (floating without climbing), struggling (making vigorous movements), and swimming (horizontal movement throughout the container) will be measured. The length of the immobility time is an index of depressive behavior.

2. Tail Suspension Test (TST) (depression): This test is believed to be more sensitive to anti-depressant agents compared to other tests. The mice can be individually suspended by the tail taped on a stand above the floor. The duration of the test can be 6 minutes. Immobility is defined as the mouse remaining completely motionless. The length of immobility time correlates with the severity of depression.

3. Elevated Plus Maze test (EPM) (anxiety): A computer controlled EPM apparatus, consisting of two open and two closed arms (all arms made of Plexiglass, 30 cm×5 cm) connected by a central platform will be used [32]. The open arms are surrounded by 4 mm high edges, whereas the closed arms have transparent Plexiglass walls (14.5 cm high) at the sides and end. The bottom, made of black Plexiglass is elevated 50 cm above the floor. At the start of each test, mice can be placed individually on the central platform and their behavior can be automatically monitored for 5 minutes. The number of entries into each arm and the time spent in each arm can be recorded and analyzed. The percentage of open arm entries and percentage of time spent in the open arm can be used as negative indices of anxiety.

4. Light/Dark Box Exploration test (LDB) (anxiety): The LDB consists of a dark compartment without illumination and a light compartment with illumination (0.25 Amp; LED light). Both compartments are connected through an opening. On the day of testing, each mouse can be allowed a 5 min pretest habituation period in the room before testing. Then, the mouse can be gently placed in the dark compartment with its head facing away from the opening. The mouse will be observed for a 5 min test period, and the time spent in each compartment will be monitored and recorded by computer. The percentage of time spent in the dark and light compartments can be calculated for each animal. The time spent in the dark box is an index of anxiety.

DHA and EPA Content of Various Brain Regions and Liver:

Total lipids of plasma, the brain regions and liver can be extracted by Bligh and Dyer procedure [46] after adding the internal standards of tri-15:0 TAG, 17:0 LPC, di-17:0 PC, di-15:0 PE, 14:1-17:0 PI, and di-17:0 PS (all from Avanti).

The total lipid extract can be methylated with methanolic HCl, and analyzed by GC/MS (Shimadzu QP2010E, equipped with a Supelco Omegawax column) by the established procedures. The percentage of DHA in the total fatty acids, as well as the amount (μg) of DHA per mg tissue will be calculated from comparison with internal standards.

Distribution of DHA and EPA Among Lipid Classes in Brain and Other Tissues:

The total DHA and EPA content of TAG, PC, PE, PS, and PI, as well as the molecular species composition of various EPA- and DHA-containing lipids can be determined by LC/MS/MS by established procedures. Briefly, the total lipid extract containing the internal standards is injected into a normal phase UPLC column, the lipids separated by a gradient elution, and the molecular species of all the lipids containing EPA and DHA will be analyzed in a QTRAP 6500 equipment in the MRM mode, as described previously.

Bioactive Metabolic Products of Arachidonate, EPA and DHA:

In addition to their direct effects, EPA and DHA can antagonize the pro-inflammatory effects of arachidonate, and are converted to several specialized bioactive and pro-resolving mediators (SPM) including Protectins, Resolvins, and Maresins, which play a major role in their anti-inflammatory functions. The bioactive compounds derived from arachidonic acid, EPA, and DHA can be determined in a separate aliquot of lipid extract by LC/MS/MS as previously described.

Gene Expression:

Total RNA and genomic DNA can be isolated from brain regions using standard procedures. The expression of Bdnf, Dnmt1, Dnmt3a, Hdac1 and Hdac2 can be examined by RT-qPCR. The PCR results can be validated at the protein level by Western blots with specific antibodies. Primers can be designed to span at least one intron-exon boundary. Housekeeping genes, (Gapdh and β-Actin) can be used as internal controls.

Western Blot Analysis:

Twenty micrograms of protein from each sample can be separated on 4-12% tris-glycine gels. The blots can be probed with the validated primary antibodies to BDNF (Santa Cruz), DNMT1, DNMT3a and HDAC1-2 (Imagenex). The levels of these proteins in the samples can be normalized to β-actin levels.

Promoter Methylations:

DNA methylation status can be measured on promoter regions of BDNF by measuring enrichment of 5 methyl Cytosine (5mC) using MeDIP as previously described. Genomic DNA isolated can be sonicated to 200 bp fragments and subjected to immunoprecipitation using specific anti-5mC antibody, followed by qPCR quantification. Primers can be designed to be specific to the CpG enriched regions on the gene promoters. Input genomic DNA that is not subjected to the methylation enrichment procedure will be used as a control and the fold change will be calculated using the $2^{-\Delta\Delta ct}$ method. These techniques have been established and routinely used in the art.

ChIP (Chromatin Immunoprecipitation) Assay:

To examine histone modification status at BDNF, a ChIP technique can be used. Briefly, tissue can be treated with formaldehyde to crosslink histones with the genomic DNAs. After washing with cold PBS containing protease inhibitors, tissues can be homogenized in SDS lysis buffer. To obtain consistent chromatin fragmentation, the lysates can be sonicated. An aliquot (1-2%) of the sonicated lysate without antibody (Input) can be used to quantitate the total amount of DNA present in different sample extracts before immunoprecipitation. Immunoprecipitation can be carried out using ChIP grade acetyl-H3K9/14 antibody. At the end of the ChIP procedure, the protein/DNA cross-linked nucleosomal chromatin complex that was immunoprecipitated by antibody can be reverse cross-linked. Samples can then be treated with proteinase-K. Protein-free DNA can be extracted for detection and quantification of Bdnf, Dnmt1, Dnmt3a, Hdac1 and Hdac2 using qPCR.

Additionally, offspring from the cohort of stressed mothers (described above) on control diet can be used for further performance studies to determine treatment and/or prevention efficacy. This cohort can be further divided and direct feeding of LPC-EPA or LPC-DHA can take place in at least one group, while at least one other group can be fed an unsupplemented diet. Thus, in some cases, offspring from stressed dams can be randomly assigned to one of four dietary groups: (1) unsupplemented rodent chow (AIN 93G, control diet); (2) LPC-EPA supplemented diet; (3) LPC-DHA supplemented diet; (4) Fish oil (or other source of omega or other fatty acids) supplemented diet. Diets can be fed ad-libitum, starting immediately after weaning until PND 74. The food can be changed daily and the amount of food consumed can be calculated based on the remaining food each day. Body weight of the animals can be measured and gain can be determined. At PND 75 or later behavioral tests can be performed. Further, brain, liver, and other tissues can be harvested and lipid analysis, Western blotting analysis, promoter methylation analysis, gene expression analysis, and ChIP assays can be performed.

We claim:

1. A compound according to Formula 1

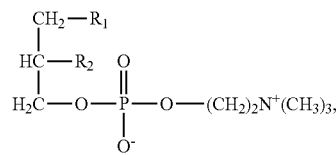

Formula 1 wherein $R_1$ is —OH, and wherein $R_2$ is EPA, or
wherein $R_1$ is eicosapentaenoic acid (EPA), and wherein $R_2$ is —OH.

2. The compound according to claim 1, wherein $R_2$ is OH.

3. The compound according to claim 1, wherein $R_1$ is OH and $R_2$ is EPA.

4. A formulation comprising:
a compound according to Formula 1

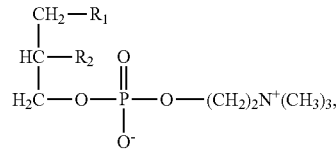

Formula 1 wherein $R_1$ is —OH, and wherein $R_2$ is EPA, or
wherein $R_1$ is eicosapentaenoic acid (EPA), and wherein $R_2$ is —OH; and
a pharmaceutically acceptable carrier.

5. The formulation of claim 4, wherein the compound according to Formula 1 is encapsulated by a micelle, forms a micelle, or is incorporated into the membrane of a vesicle.

6. The formulation of claim 5, wherein the micelle or vesicle further comprises a cholesterol, phosphatidylcholine, a fatty acid, a monoolein, or any combination thereof.

7. The formulation of claim 4, wherein the amount of the compound according to Formula 1 is an effective amount.

8. The formulation of claim 7, wherein the amount of the compound according to Formula 1 is an amount effective to treat depression.

9. The formulation of claim 7, wherein the amount of the compound according to Formula 1 is an amount effective to treat a neurological disease or disorder.

10. The formulation of claim 9, wherein the neurological disease or disorder is Alzheimer's disease, Parkinson's, or a traumatic brain injury.

11. The formulation of claim 7, wherein the amount of the compound according to Formula 1 is an amount effective to enhance the cognitive function in a subject.

12. The formulation of claim 7, wherein the amount of the compound according to Formula 1 is an amount effective to increase the levels of DHA, EPA, or DHA and EPA in the brain of a subject.

13. The formulation of claim 4, wherein the formulation is a dietary supplement.

14. The formulation of claim 4, wherein the formulation is a functional food item.

15. A method comprising:
    administering an amount of a compound according to Formula 1

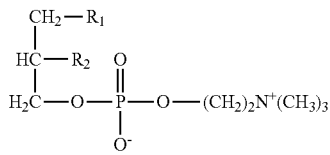

Formula 1 to a subject, wherein $R_1$ is —OH, and wherein $R_2$ is EPA, or wherein $R_1$ is eicosapentaenoic acid (EPA), and wherein $R_2$ is —OH.

16. The method of claim 15, wherein the subject has or is suspected of having a neurological disease or disorder.

17. The method of claim 16, wherein the neurological disease or disorder is depression, Alzheimer's, Parkinson's, or a traumatic brain injury.

18. The method of claim 15, wherein the amount of the compound according to Formula 1 is an amount effective to increase the amount of DHA, EPA, or DHA and EPA in the brain of the subject.

19. The method of claim 15, wherein the amount of the compound according to Formula 1 is an amount effective to treat a neurological disease or disorder.

20. The method of claim 19, wherein the neurological disease or disorder is depression, Alzheimer's, Parkinson's, or a traumatic brain injury.

* * * * *